US011407775B2

(12) United States Patent
Butler et al.

(10) Patent No.: US 11,407,775 B2
(45) Date of Patent: Aug. 9, 2022

(54) COMPOSITIONS AND METHODS FOR PHOSPHORAMIDITE AND OLIGONUCLEOTIDE SYNTHESIS

(71) Applicant: WAVE LIFE SCIENCES LTD., Singapore (SG)

(72) Inventors: David Charles Donnell Butler, Medford, MA (US); Subramanian Marappan, Acton, MA (US); Ik-Hyeon Paik, Needham, MA (US)

(73) Assignee: WAVE LIFE SCIENCES LTD., Singapore (SG)

( * ) Notice: Subject to any disclaimer, the term of this patent is extended or adjusted under 35 U.S.C. 154(b) by 0 days.

(21) Appl. No.: 16/084,556

(22) PCT Filed: Mar. 13, 2017

(86) PCT No.: PCT/US2017/022135
§ 371 (c)(1),
(2) Date: Sep. 12, 2018

(87) PCT Pub. No.: WO2017/160741
PCT Pub. Date: Sep. 21, 2017

(65) Prior Publication Data
US 2019/0077817 A1    Mar. 14, 2019

Related U.S. Application Data

(60) Provisional application No. 62/307,542, filed on Mar. 13, 2016.

(51) Int. Cl.
| | | |
|---|---|---|
| *C07F 9/6584* | (2006.01) | |
| *C07H 1/06* | (2006.01) | |
| *C07H 19/06* | (2006.01) | |
| *C07H 19/16* | (2006.01) | |

(52) U.S. Cl.
CPC ........... *C07F 9/65844* (2013.01); *C07H 1/06* (2013.01); *C07H 19/06* (2013.01); *C07H 19/16* (2013.01)

(58) Field of Classification Search
CPC ........... C07H 1/06; C07H 19/06; C07H 19/16
See application file for complete search history.

(56) References Cited

U.S. PATENT DOCUMENTS

| | | | |
|---|---|---|---|
| 5,846,466 A | 12/1998 | Abe et al. | |
| 5,869,696 A * | 2/1999 | Reddy .............. | C07H 21/00 536/25.3 |
| 6,133,438 A | 10/2000 | Cook et al. | |
| 6,867,294 B1 | 3/2005 | Sanghvi et al. | |
| 7,030,230 B2 * | 4/2006 | Ross .............. | C07H 19/04 536/16.1 |
| 7,057,062 B2 | 6/2006 | Song et al. | |
| 7,101,993 B1 | 9/2006 | Cook et al. | |
| 8,431,693 B2 | 4/2013 | Manoharan et al. | |
| 8,470,987 B2 | 6/2013 | Wada et al. | |
| 8,822,671 B2 | 9/2014 | Shimizu et al. | |
| 8,859,755 B2 | 10/2014 | Wada et al. | |
| 9,394,333 B2 | 7/2016 | Wada et al. | |
| 9,598,458 B2 | 3/2017 | Shimizu et al. | |
| 9,605,019 B2 | 3/2017 | Verdine et al. | |
| 9,617,547 B2 | 4/2017 | Gemba | |
| 9,695,211 B2 | 7/2017 | Wada et al. | |
| 9,744,183 B2 | 8/2017 | Verdine et al. | |
| 9,982,257 B2 | 5/2018 | Butler et al. | |
| 10,144,933 B2 | 12/2018 | Gemba et al. | |
| 10,149,905 B2 | 12/2018 | Gemba et al. | |
| 10,160,969 B2 | 12/2018 | Meena et al. | |
| 10,167,309 B2 | 1/2019 | Shimizu et al. | |
| 10,280,192 B2 | 5/2019 | Verdine et al. | |
| 10,307,434 B2 | 6/2019 | Verdine et al. | |
| 10,322,173 B2 | 6/2019 | Gemba et al. | |
| 10,329,318 B2 | 6/2019 | Wada et al. | |
| 10,428,019 B2 | 10/2019 | Wada et al. | |
| 10,450,568 B2 | 10/2019 | Butler et al. | |
| 10,479,995 B2 | 11/2019 | Vargeese et al. | |
| 10,590,413 B2 | 3/2020 | Butler et al. | |
| 10,696,711 B2 | 6/2020 | Shimizu et al. | |
| 10,724,035 B2 | 7/2020 | Vargeese et al. | |
| 10,815,482 B2 | 10/2020 | Meena et al. | |
| 11,013,757 B2 | 5/2021 | Zhang et al. | |
| 11,136,346 B2 | 10/2021 | Shimizu et al. | |
| 2003/0232978 A1 | 12/2003 | Seeberger et al. | |
| 2011/0178284 A1 | 7/2011 | Wada et al. | |
| 2011/0294124 A1 | 12/2011 | Wada et al. | |
| 2012/0316224 A1 | 12/2012 | Verdine et al. | |

(Continued)

FOREIGN PATENT DOCUMENTS

| | | |
|---|---|---|
| CN | 102675386 A | 9/2012 |
| JP | H10-504022 A | 4/1998 |

(Continued)

OTHER PUBLICATIONS

Almer, et al. A New Approach to Stereospecific Synthesis of P-chiral Phosphorothioates. Preparation of Diastereomeric Dithymidyl-(3'-5') Phosphorothioates, Chem. Commun., (3): 290-1 (2004).
Arai, K. et al., Synthesis and properties of novel 2'-O-alkoxymethyl-modified nucleic acids, Bioorganic & Medicinal Chemistry Letters, 21(21): 6285-6287 (2011).
Bobkov, G.V. et al., Phosphoramidite building blocks for efficient incorporation of 2'-O-aminoethoxy(and propoxy)methyl nucleosides into oligonucleotides, Tetrahedron, 64: 6238-6251 (2008).
Cramer, H., Different Approaches to Oligonucleotide Synthesis, WAVE Life Sciences, Presented at the 7th Annual Oligo Networking Event, Roche Basel, Switzerland, 31 pages (Mar. 26, 2019).
Current Protocols in Nucleic Acid Chemistry, Edited by Beaucage, S.L. et al., Chapter 2: Protection of Nucleosides for Oligonucleotide Synthesis, 2.0.1.-2.16.31 (2012).

(Continued)

*Primary Examiner* — Bahar Craigo
(74) *Attorney, Agent, or Firm* — Choate, Hall & Stewart LLP; Brenda Herschbach Jarrell; Xiaodong Li

(57) ABSTRACT

The present disclosure, among other things, provides technologies for preparing and purifying phosphoramidites for oligonucleotide synthesis.

26 Claims, 2 Drawing Sheets

(56) References Cited

U.S. PATENT DOCUMENTS

| | | |
|---|---|---|
| 2013/0178612 A1 | 7/2013 | Wada et al. |
| 2013/0184450 A1 | 7/2013 | Wada et al. |
| 2013/0253178 A1 | 9/2013 | Shimizu et al. |
| 2014/0194610 A1 | 7/2014 | Verdine et al. |
| 2015/0166999 A1 | 6/2015 | Gemba |
| 2015/0197540 A1 | 7/2015 | Shimizu et al. |
| 2015/0211006 A1 | 7/2015 | Butler et al. |
| 2016/0331835 A1 | 11/2016 | Gemba et al. |
| 2016/0331836 A1 | 11/2016 | Gemba et al. |
| 2016/0333349 A1 | 11/2016 | Gemba et al. |
| 2016/0347780 A1 | 12/2016 | Wada et al. |
| 2016/0347784 A1 | 12/2016 | Verdine et al. |
| 2017/0029445 A1 | 2/2017 | Shimizu et al. |
| 2017/0029457 A1 | 2/2017 | Verdine et al. |
| 2017/0037399 A1 | 2/2017 | Meena et al. |
| 2017/0275621 A1 | 9/2017 | Butler et al. |
| 2018/0111958 A1 | 4/2018 | Wada et al. |
| 2018/0216107 A1 | 8/2018 | Frank-Kamenetsky et al. |
| 2018/0216108 A1 | 8/2018 | Vargeese et al. |
| 2018/0222936 A1 | 8/2018 | Verdine et al. |
| 2019/0008986 A1 | 1/2019 | Butler et al. |
| 2019/0106696 A1 | 4/2019 | Meena et al. |
| 2019/0127733 A1 | 5/2019 | Butler et al. |
| 2019/0177357 A1 | 6/2019 | Shimizu et al. |
| 2019/0209604 A1 | 7/2019 | Zhang et al. |
| 2019/0249173 A1 | 8/2019 | Vargeese et al. |
| 2019/0264267 A1 | 8/2019 | Yang et al. |
| 2019/0375774 A1 | 12/2019 | Butler et al. |
| 2019/0390197 A1 | 12/2019 | Butler et al. |
| 2020/0080083 A1 | 3/2020 | Vargeese et al. |
| 2020/0157545 A1 | 5/2020 | Vargeese et al. |
| 2020/0190515 A1 | 6/2020 | Vargeese et al. |
| 2020/0231620 A1 | 7/2020 | Bowman et al. |
| 2020/0299692 A1 | 9/2020 | Frank-Kamenetsky et al. |
| 2020/0362337 A1 | 11/2020 | Dodart et al. |
| 2020/0385420 A1 | 12/2020 | Shimizu et al. |
| 2021/0032620 A1 | 2/2021 | Vargeese et al. |
| 2021/0115444 A1 | 4/2021 | Meena et al. |
| 2021/0130821 A1 | 5/2021 | Butler et al. |
| 2021/0198305 A1 | 7/2021 | Vargeese et al. |
| 2021/0228615 A1 | 7/2021 | Zhang et al. |
| 2021/0254062 A1 | 8/2021 | Zhang et al. |

FOREIGN PATENT DOCUMENTS

| | | |
|---|---|---|
| JP | 2000-500158 A | 1/2000 |
| JP | 2003/238586 A | 8/2003 |
| JP | 2007-531794 A | 11/2007 |
| JP | 2009-067777 A | 4/2009 |
| JP | 2011-121881 A | 6/2011 |
| JP | 2011-184318 A | 9/2011 |
| JP | 2015-523316 A | 8/2015 |
| WO | WO-1995/15333 A1 | 6/1995 |
| WO | WO-1995/31434 A1 | 11/1995 |
| WO | WO-97/09443 A1 | 3/1997 |
| WO | WO-1997/40458 A2 | 10/1997 |
| WO | WO-2005/014609 A2 | 2/2005 |
| WO | WO-2005/023828 A1 | 3/2005 |
| WO | WO-2005/028494 A1 | 3/2005 |
| WO | WO-2005/070859 A1 | 8/2005 |
| WO | WO-2005/085272 A1 | 9/2005 |
| WO | WO-2005/092909 A1 | 10/2005 |
| WO | WO-2005/097817 A2 | 10/2005 |
| WO | WO-2009/143369 A2 | 11/2009 |
| WO | WO-2010/064146 A2 | 6/2010 |
| WO | WO-2011/005761 A1 | 1/2011 |
| WO | WO-2011/034072 A1 | 3/2011 |
| WO | WO-2011/108682 A1 | 9/2011 |
| WO | WO-2012/039448 A1 | 3/2012 |
| WO | WO-2012/073857 A1 | 6/2012 |
| WO | WO-2013/012758 A1 | 1/2013 |
| WO | WO-2014/010250 A1 | 1/2014 |
| WO | WO-2014/010718 A1 | 1/2014 |
| WO | WO-2014/012081 A2 | 1/2014 |
| WO | WO-2015/107425 A2 | 7/2015 |
| WO | WO-2015/108046 A1 | 7/2015 |
| WO | WO-2015/108047 A1 | 7/2015 |
| WO | WO-2015/108048 A1 | 7/2015 |
| WO | WO-2015/168461 A2 | 11/2015 |
| WO | WO-2017/015555 A1 | 1/2017 |
| WO | WO-2017/015575 A1 | 1/2017 |
| WO | WO-2017/062862 A2 | 4/2017 |
| WO | WO-2017/160741 A1 | 9/2017 |
| WO | WO-2017/192664 A1 | 11/2017 |
| WO | WO-2017/192679 A1 | 11/2017 |
| WO | WO-2017/210647 A1 | 12/2017 |
| WO | WO-2018/022473 A1 | 2/2018 |
| WO | WO-2018/067973 A1 | 4/2018 |
| WO | WO-2018/098264 A1 | 5/2018 |
| WO | WO-2018/223056 A1 | 12/2018 |
| WO | WO-2018/223073 A1 | 12/2018 |
| WO | WO-2018/223081 A1 | 12/2018 |
| WO | WO-2018/237194 A1 | 12/2018 |
| WO | WO-2019/002237 A1 | 1/2019 |
| WO | WO-2019/032607 A1 | 2/2019 |
| WO | WO-2019/032612 A1 | 2/2019 |
| WO | WO-2019/055951 A1 | 3/2019 |
| WO | WO-2019/075357 A1 | 4/2019 |
| WO | WO-2019/200185 A1 | 10/2019 |
| WO | WO-2019/217784 A1 | 11/2019 |
| WO | WO-2020/118246 A1 | 6/2020 |
| WO | WO-2020/160336 A1 | 8/2020 |
| WO | WO-2020/191252 A1 | 9/2020 |
| WO | WO-2020/196662 A1 | 10/2020 |
| WO | WO-2020/219981 A2 | 10/2020 |
| WO | WO-2020/219983 A2 | 10/2020 |
| WO | WO-2020/227691 A2 | 11/2020 |
| WO | WO-2021/071788 A2 | 4/2021 |
| WO | WO-2021/071858 A1 | 4/2021 |
| WO | WO-2021/178237 A2 | 9/2021 |

OTHER PUBLICATIONS

Deleavey, G.F. and Damha, M.J., Designing chemically modified oligonucleotides for targeted gene silencing. Chem. Biol., 19: 937-54 (2012).

Hargreaves, J.S. et al., The Degradation of dG Phosphoramidites in Solution, Nucleosides, Nucleotides and Nucleic Acids, 24(10): 691-707 (2015).

International Search Report for PCT/US2017/022135, 3 pages (dated Jun. 6, 2017).

Iwamoto et al., Stereocontrolled Synthesis of H-phosphonate DNA, Nucleic Acids Symposium Series, (50):159-60 (2006).

Iwamoto, N. et al., Control of phosphorothioate stereochemistry substantially increases the efficacy of antisense oligonucleotides, Nature Biotechnology, 1-7 pages (2017). All Supplemental Data, 8-53 pages (2017).

Iwamoto, N. et al., Optimization of Therapeutic Phosphorothioate Oligonucleotides by P-Chirality Control, WAVE Life Sciences, PSJ Congress: The Pharmaceutical Society of Japan, (Mar. 25, 2015-Mar. 28, 2016).

Iwamoto, N. et al., Stereocontrolled solid-phase synthesis of oligonucleoside H-phosphonates by an oxazaphospholidine approach, Angewandte Chemie International Edition, 48(3):496-499 (2009).

Koshkin, A.A. et al., LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition, Tetrahedron 54: 3607-3630 (1998).

Krotz, A.H. et al., Phosphorothioate Oligonucleotides with Low Phosphate Diester Content: Greater than 99.9% Sulfurization Efficiency with "Aged" Solutions of Phenylacetyl Disulfide (PADS), Organic Process Research & Development, 8: 852-858 (2004).

Krotz, A.H. et al., Solution Stability and Degradation Pathway of Deoxyriboncleoside Phosphoramidites in Acetonitrile, Nucleosides, Nucleotides and Nucleic Acids, 23(5): 767-775 (2004).

Leviten, M., Wave's Purity Progress, Biocentury, 1-6 (Sep. 28, 2017).

Meena, Control of Human RNase H Mediated Cleavage by Stereopure Phosphorothioate Oligonucleotides, WAVE Life Sciences, TIDES Meeting, 23 pages (May 3-6, 2015).

(56) References Cited

OTHER PUBLICATIONS

Meena, Development of Allele Specific Antisense Oligonucleotides, WAVE Life Sciences, ACS Central Regional Meeting (CERM), Covington, KY (May 19, 2016).

Meena, Development of Allele Specific Antisense Oligonucleotides, WAVE Life Sciences, TIDES Meeting (May 11, 2016).

Meena, et al., Discovery and Early Clinical Development of the First Allele-Specific Stereopure ASO Drug Candidate with Disease—Modifying Potential for the Treatment of Huntington's Disease, WAVE Life Sciences, Poster, 1 page (2016).

Meena, et al., Therapeutic Implications of Controlling P-Chirality in Phosphorothioate Oligonucleotides, TIDES Poster (May 12-15, 2014).

Nawrot et al., DNA Oligonucleotides Containing Stereodefined Phosphorothioate Linkages in Selected Positions, Current Protocols in Nucleic Acid Chemistry, UNIT 4.34: 4.34.1-4.34.15 (2009).

Nukaga, Y. et al., Stereocontrolled Solid-Phase Synthesis of Phosphate/Phosphorothioate (PO/PS) Chimeric Oligodeoxyribonucleotides on an Automated Synthesizer Using an Oxazaphospholidine-Phosphoramidite Method, J. Org. Chem., A-J, 10 pages (Publication Date (Web): Mar. 3, 2016).

Nukaga, Y. et al., Stereocontrolled Solid-Phase Synthesis of Phosphorothioate Oligoribonucleotides Using 2'-O-(2-Cyanoethoxymethyl)-nucleoside 3'-O-Oxazaphospholiidine Monomers, Journal of Organic Chemistry, 77(18):7913-7922 (2012).

Oka, N. and Wada, T., Stereocontrolled synthesis of oligonucleotide analogs containing chiral internucleotidic phosphorus atoms, Chemical Society Reviews, 40(12):5829-5843 (2011).

Oka, N. et al., Solid-Phase Synthesis of Stereoregular Oligodeoxyribonucleoside Phosphorothioates Using Bicyclic Oxazaphospholidine Derivatives as Monomer Units, Journal of the American Chemical Society, 130(47):16031-16037 (2008).

Oka, N. et al., Solid-Phase Synthesis of Stereoregular Oligodeoxyribonucleoside Phosphorothioates Using Bicyclic Oxazaphospholidine Derivatives as Monomer Units, Journal of the American Chemical Society, 130(47):16031-16037 (2008). Supporting Information, 57 pages.

PubChem, Substance Record for SID 174316404, Available Date: Mar. 31, 2014 (retrieved on Feb. 26, 2018). Retrieved from the Internet: <URL: https://pubchem.ncbi.nlm.nih.gov/substance/174316404>.

PubChem, Substance Record for SID 174316700, Available Date: Mar. 31, 2014 (retrieved on Feb. 26, 2018). Retrieved from the Internet: <URL: https://pubchem.ncbi.nlm.nih.gov/substance/174316700>.

PubChem, Substance Record for SID 174316999, Available Date: Mar. 31, 2014 {retrieved on Feb. 26, 2018). Retrieved from the Internet: <URL: https://pubchem.ncbi.nlm.nih.gov/substance/174316999>.

Schultz, R.G. and Gryaznov, S.M., Oligo-24-fluoro-24-deoxynucleotide N3'->P5' phosphoramidates: synthesis and properties, Nucleic Acids Res., 24(15): 2966-2973 (1996).

Singh, S.K. et al., Synthesis of Novel Bicyclo[2.2.1] Ribonucleosides: 2'-Amino- and 2'-Thio-LNA Monomeric Nucleosides, J. Org. Chem., 63: 6078-6079 (1998).

Sorensen, M.D., Functionalized LNA (locked nucleic acid): high-affinity hybridization of oligonucleotides containing N-acylated and N-alkylated 2'-amino-LNA monomers, Chem. Comm., 2130-2131 (2003).

Stec, W.J. et al., Deoxyribonucleoside 3'-O-(2-Thio- and 2-Oxo-"spiro"-4,4-pentamethylene-1,3,2-oxathiaphospholane)s: Monomers for Stereocontrolled Synthesis of Oligo(deoxyribonucleoside phosphorothioate)s and Chimeric PS/PO Oligonucleotides, J. Am. Chem. Soc., 120(29): 7156-7167 (1998).

Stevens, W.C. et al., General methods for flash chromatography using disposable columns, Molecular Diversity, Kluwer Academic Publishers, DO, 13(2): 247-252 (2009).

Swayze, E.E. and Bhat, B., The medicinal chemistry of oligonucleotides, Crooke, S.T. (ed) Antisense Drug Technology: Principles, Strategies, and Applications, CRC Press, Boca Raton, FL: 143-82 (2007).

Tian, J. et al., Advancing high-throughput gene synthesis technology, Mol. BioSyst., 5: 714-722 (2009).

U.S. Food and Drug Administration, Development of New Stereoisomeric Drugs, 8 pages (May 1, 1992). URL: http://www.fda.gov/Drugs/GuidanceComplianceRegulatoryInformation/Guidances/ucm122883.htm [Retrieved Jun. 15, 2016].

Verhagen et al., A Conformationally locked Aminomethyl C-Glycoside and Studies on Its N-Pyren-1-ylcarbonyl Derivative Inserted into Oligodeoxynucleotides, European Journal of Organic Chemistry, 2538-2548 (2006).

Verma, S. and Eckstein, F., Modified Oligonucleotides: Synthesis and Strategy for Users, Annu. Rev. Biochem., 67: 99-134 (1998).

Wan et al., Synthesis of Second Generation Antisense Oligonucleotides Containing Chiral Phosphorothioate Linkages and Evaluation of their Biophysical Properties and Biological Activity, 10th Annual Meeting of the Oligonucleotide Therapeutics Society, abstract received by Applicant Oct. 7, 2014, poster setup prior to presentation (first known to Applicant late Oct. 12, 2014, PST), poster presentation Oct. 13, 2014.

Wan, Q. et al., Thermal pretreatment of silica composite filler materials, Journal of Thermal Analysis and Calorimetry, Kluwer Academic Publishers, Dordrecht, NL, 99(1): 237-243 (2009).

Wan, W.B. and Seth, P.P., The Medicinal Chemistry of Therapeutic Oligonucleotides, J. Med. Chem., 59: 9645-9667 (2016).

Wan, W.B. et al., Synthesis, biophysical properties and biological activity of second generation antisense oligonucleotides containing chiral phosphorothioate linkages, Nucleic Acid Research, 42: 13456-13468 (2014). Supplementary Information, 14 pages.

Wilk, A. et al., Deoxyribonucleoside Cyclic N-Acylphosphoramidites as a New Class of Monomers for the Stereocontrolled Synthesis of Oligothymidylyl- and Oligodeoxycytidylyl-Phosphorothioates, Journal of the American Chemical Society, 122(10): 2149-2156 (2000).

Written Opinion for PCT/US2017/022135, 11 pages (dated Jun. 6, 2017).

Zhuravlev, L.T. et al., Structurally bound water and surface characterization of amorphous silica, Pure & Applied Chemistry, 61(11): 1969-1976 (1989).

U.S. Appl. No. 16/618,003, filed Nov. 27, 2019, Vargeese et al.
U.S. Appl. No. 16/624,896, filed Dec. 19, 2019, Butler et al.
U.S. Appl. No. 16/717,986, filed Dec. 17, 2019, Butler et al.
U.S. Appl. No. 16/755,544, filed Apr. 10, 2020, Zhang et al.
U.S. Appl. No. 16/869,126, filed May 7, 2020, Vargeese et al.
U.S. Appl. No. 17/016,313, filed Sep. 9, 2020, Meena et al.
U.S. Appl. No. 17/046,752, filed Oct. 9, 2020, Zhang et al.
U.S. Appl. No. 17/054,452, filed Nov. 10, 2020, Zhang et al.
U.S. Appl. No. 17/177,111, filed Feb. 16, 2021, Zhang et al.
U.S. Appl. No. 17/311,285, filed Jun. 4, 2021, Zhang et al.
U.S. Appl. No. 17/375,658, filed Jul. 14, 2021, Vargeese et al.
U.S. Appl. No. 17/426,511, filed Jul. 28, 2021, Brown et al.
U.S. Appl. No. 17/439,755, filed Sep. 15, 2021, Kandasamy et al.
U.S. Appl. No. 17/465,238, filed Sep. 2, 2021, Shimizu et al.

Bradley, D. et al., Drying of Organic Solvents: Quantitative Evaluation of the Efficiency of Several Desiccants, J. Org. Chem., 75:8351-8354 (2010).

Chem Station, I tried collecting small silica gel material, blog, 15 pages, posted May 16, 2012, <https://www.chem-station.com/blog/2012/05/post-386.html>.

GIEBEL FilTec, Fundamentals for the regeneration of silica gel, GIEBEL Adsorber, 5 pages (Jan. 1, 2009), <https://blog.giebel-adsorber.de/wp-content/uploads/2020/02/Silicagel_Fundamentals-Regeneration-Of-Silicagel_EN.pdf>.

SiliCycle, How can the columns be cleaned or regenerated, website, 2 pages (Jun. 14, 2021), https://www.silicycle.com/faq/hplc/how-can-the-columns-be-cleaned-or-regenerated.

* cited by examiner

COMPOSITIONS AND METHODS FOR PHOSPHORAMIDITE AND OLIGONUCLEOTIDE SYNTHESIS

CROSS-REFERENCE TO RELATED APPLICATIONS

This application is a United States National Stage Application of International PCT Application PCT/US17/22135, filed Mar. 13, 2017, which claims priority to U.S. Provisional Application No. 62/307,542, filed Mar. 13, 2016, the entirety of each of which is incorporated herein by reference.

BACKGROUND

Oligonucleotides are useful for many purposes, including treating various diseases. There is a need for efficient synthetic methods for oligonucleotides.

SUMMARY

The present disclosure encompasses the recognition of the source of a problem with many technologies for preparation of phosphoramidites. As is known in the art, phosphoramidites are often utilized as monomers for oligonucleotide synthesis. Many technologies for preparing phosphoramidites can suffer from low yields and/or purity. Among other things, the present disclosure provides technologies (e.g., compounds, compositions, methods, etc.) that provide significantly improved yields and/or purity for preparation of phosphoramidites, and/or other intermediates and products, that are useful for e.g., improving efficiency and/or lowering cost of oligonucleotide preparation.

The present disclosure encompasses certain surprising findings, including that certain processes for pre-treating a purification medium can surprisingly improve utility and/or effectiveness of that medium, particularly for use in preparation of phosphoramidites. In some embodiments, such processes may be or comprise a deactivation process. In some embodiments, such processes may be or comprise removal or exclusion of water from the medium. In some embodiments, such processes may be or comprise treatment with a hygroscopic solvent system comprising one or more hygroscopic solvent. In some embodiments, such processes may be or comprise treatment with a hygroscopic solvent. In some embodiments, such processes may be or comprise treatment with an alcohol. In some embodiments, such processes may be or comprise treatment with methanol. In some embodiments, such processes may be or comprise treatment with ethanol. In some embodiments, such processes may be or comprise treatment with isopropanol. In some embodiments, such processes may be or comprise treatment with dimethyl carbonate. In some embodiments, such processes may be or comprise treatment with acetonitrile. In some embodiments, such processes may be or comprise treatment with ethyl acetate. In some embodiments, such processes may be or comprise treatment with acetone. In some embodiments, the present disclosure demonstrates that certain such processes, including certain processes that were previously understood or expected to degrade or otherwise damage one or more purification medium, may in fact improve utility and/or effectiveness of such a medium, particularly in the preparation of phosphoramidites. In some embodiments, teachings of the present disclosure relate to a medium that is or comprises a silica medium. In some embodiments, teachings of the present disclosure relate to a medium that is or comprises a silica gel.

In some embodiments, the present disclosure appreciates that one source of a problem with prior technologies that utilize chromatography purification (e.g., purification using silica gel, alumina, etc.) in preparation of phosphoramidites may be that a significant amount of phosphoramidite may be lost during chromatography. Without wishing to be bound by any particular theory, the present disclosure proposes that, in some instances, phosphoramidite may be lost through irreversible adsorption to (e.g., cannot be readily eluted during chromatographic purification), and/or decomposition when in contact with, a purification medium, such as silica gel, alumina, etc. In some embodiments, the present disclosure encompasses the recognition that the low yield and/or purity of phosphoramidites can greatly increase the cost of oligonucleotides and/or pharmaceutical compositions thereof, particularly at large scale such as those required for preparing oligonucleotide-based medicament for therapy. The present disclosure provides a particular insight that, in some embodiments, treatment of a purification medium as described herein may improve its performance (and therefore its utility and/or efficacy) in purification of phosphoramidites.

In some embodiments, the present disclosure provides new technologies, e.g., compounds, compositions, methods, etc., for preparing a phosphoramidite and/or an oligonucleotide. In some embodiments, the present disclosure provides new technologies for purifying phosphoramidites. In some embodiments, provided technologies greatly improve efficiency of phosphoramidite synthesis, and/or significantly decrease the cost of phosphoramidite, and oligonucleotides, compositions and medicaments prepared therefrom.

In some embodiments, the present disclosure provides a method, comprising steps of:
  a) pre-treating a purification medium;
  b) contacting the purification medium with a phosphoramidite; and
  b) optionally using the purification medium to purify a phosphoramidite.

In some embodiments, the present disclosure provides a method, comprising steps of:
  a) pre-treating a purification medium; and
  b) using the purification medium to purify a phosphoramidite.

In some embodiments, the present disclosure provides a method, comprising steps of:
  a) pre-treating a purification medium comprising silica gel; and
  b) contacting the purification medium with a phosphoramidite.

In some embodiments, the present disclosure provides a method, comprising steps of:
  a) pre-treating a purification medium comprising silica gel; and
  b) using the purification medium to purify a phosphoramidite.

In some embodiments, the present disclosure provides a method, comprising steps of:
  a) pre-treating silica gel; and
  b) contacting the silica gel with a phosphoramidite.

In some embodiments, the present disclosure provides a method, comprising steps of:
  a) pre-treating silica gel; and
  b) using the silica gel to purify a phosphoramidite.

In some embodiments, the pre-treatment removes water from the purification medium. In some embodiments, the pre-treatment deactivates the purification medium. In some embodiments, the pre-treatment comprises contacting the purification medium with a first solvent system. In some embodiments, a first solvent system comprises a hygroscopic solvent. In some embodiments, a first solvent system is a hygroscopic solvent. In some embodiments, a hygroscopic solvent is an alcohol. In some embodiments, a hygroscopic solvent is methanol. In some embodiments, a hygroscopic solvent is ethanol. In some embodiments, a hygroscopic solvent is isopropanol. In some embodiments, a hygroscopic solvent is acetone. In some embodiments, a hygroscopic solvent is dimethyl carbonate. In some embodiments, a hygroscopic solvent is acetonitrile. In some embodiments, a hygroscopic solvent is ethyl acetate. In some embodiments, a first solvent system deactivates a reaction site of a purification medium. In some embodiments, the pre-treatment comprises heating the purification medium.

In some embodiments, the present disclosure provides a method, comprising steps of:
a) removing water from a purification medium;
b) contacting the purification medium with a phosphoramidite; and
c) optionally using the purification medium to purify a phosphoramidite.

In some embodiments, the present disclosure provides a method, comprising steps of:
a) removing water from a purification medium;
b) contacting the purification medium with a phosphoramidite; and
c) using the purification medium to purify a phosphoramidite.

In some embodiments, the present disclosure provides a method, comprising steps of:
a) removing water from a purification medium; and
b) using the purification medium to purify the phosphoramidite.

In some embodiments, the present disclosure provides a method for improving recovery rate of a phosphoramidite, comprising steps of:
a) removing water from a purification medium;
b) adding the phosphoramidite to the purification medium; and
c) eluting the phosphoramidite from the purification medium with a solvent system; wherein the recovery rate is higher than a reference recovery rate when step a) is absent.

In some embodiments, the present disclosure provides a method for decreasing decomposition of a phosphoramidite when the phosphoramidite contacts a purification medium, comprising:
a) removing water from the purification medium.

In some embodiments, the present disclosure provides a method comprising steps of:
a) deactivating a purification medium; and
b) using the purification medium to purify a phosphoramidite;
so that the deactivated purification medium provides a higher recovery rate than the purification medium without deactivation.

In some embodiments, the present disclosure provides a method comprising steps of:
a) removing water from a purification medium;
b) contacting the purification medium with a phosphoramidite; and
c) optionally using the purification medium to purify the phosphoramidite.

In some embodiments, the present disclosure provides a method comprising steps of:
a) removing water from a purification medium;
b) contacting the purification medium with a phosphoramidite; and
c) using the purification medium to purify the phosphoramidite.

In some embodiments, the present disclosure provides a method comprising steps of:
a) removing water from a purification medium; and
b) using the purification medium to purify a phosphoramidite.

In some embodiments, the present disclosure provides a method comprising steps of:
a) mechanically removing water from a purification medium;
b) contacting the purification medium with a phosphoramidite; and
c) optionally using the purification medium to purify a phosphoramidite.

In some embodiments, the present disclosure provides a method comprising steps of:
a) mechanically removing water from a purification medium;
b) contacting the purification medium with a phosphoramidite; and
c) using the purification medium to purify a phosphoramidite.

In some embodiments, the present disclosure provides a method comprising steps of:
a) mechanically removing water from a purification medium; and
b) using the purification medium to purify a phosphoramidite.

In some embodiments, the present disclosure provides a method comprising steps of:
a) treating a purification medium with a hygroscopic solvent; and
b) using the purification medium to purify a phosphoramidite.

In some embodiments, the present disclosure provides a method comprising steps of:
a) treating a purification medium with an alcohol; and
b) using the purification medium to purify a phosphoramidite.

In some embodiments, the present disclosure provides a method comprising steps of:
a) treating a purification medium with one or more alcohols;
b) re-equilibrating the purification medium with a solvent system less polar than the one or more alcohols;
c) using the silica gel to purify a phosphoramidite, wherein the elution solvent system is less polar than the one or more alcohols.

In some embodiments, the present disclosure provides a method comprising steps of:
a) treating a purification medium with methanol;
b) re-equilibrating the purification medium with a solvent system comprising ethyl acetate and hexanes;
c) using the purification medium to purify a phosphoramidite, wherein the elution solvent system comprises ethyl acetate, hexanes, and optionally a modifier.

In some embodiments, the present disclosure provides a method comprising steps of:
a) treating a purification medium with methanol;
b) re-equilibrating the purification medium with a solvent system comprising ethyl acetate and hexanes;
c) using the purification medium to purify a phosphoramidite, wherein the elution solvent system is a mixture of ethyl acetate and hexanes.

In some embodiments, the present disclosure provides a method comprising steps of:
a) treating a purification medium with methanol;
b) re-equilibrating the purification medium with a solvent system comprising ethyl acetate and hexanes;
c) using the purification medium to purify a phosphoramidite, wherein the elution solvent system is a mixture of ethyl acetate, hexanes and triethylamine.

In some embodiments, the present disclosure provides a method, comprising:
contacting a compound with a medium;
wherein the medium is de-activated.

In some embodiments, the present disclosure provides a method, comprising:
purifying a compound with a medium;
wherein the medium is de-activated.

In some embodiments, a compound is a phosphoramidite. In some embodiments, a compound is a nucleoside. In some embodiments, a compound is a nucleotide. In some embodiments, a compound is an oligonucleotide. In some embodiments, a medium is a purification medium. In some embodiments, a medium comprises silica gel. In some embodiments, a medium is silica gel. In some embodiments, a medium is de-activated mechanically as described in the present disclosure. In some embodiments, a medium is de-activated using a solvent system or solvent as described in the present disclosure. In some embodiments, a medium is de-activated by contact with a solvent system is or comprises a hygroscopic solvent as described in the present disclosure.

In some embodiments, a provided method is a chromatography method comprising using a medium as described in the present disclosure. In some embodiments, a medium is or comprises silica gel. In some embodiments, a medium is de-activated through, e.g., mechanical means, contact with a hygroscopic solvent (system), etc.

In some embodiments, the present disclosure provides compositions from preparing a phosphoramidite. In some embodiments, the present disclosure provides a composition comprising:
a) a de-activated purification medium;
b) a phosphoramidite.

In some embodiments, a phosphoramidite is in contact with a de-activated purification medium. In some embodiments, a phosphoramidite is adsorbed on a de-activated purification medium.

In some embodiments, treating a purification medium with a solvent system or solvent is or comprises contacting a purification medium with a solvent system or solvent.

In some embodiments, a phosphoramidite is a nucleoside phosphoramidite. In some embodiments, a phosphoramidite is one described in WO/2011/005761, US/2012/0316224, WO/2013/012758, US/2014/0194610, WO/2014/012081, US/2015/0211006, WO/2015/107425, US/2017/0037399, WO/2010/064146, US/2011/0294124, WO/2014/010250, US/2015/0197540, WO/2011/108682, US/2013/0184450, WO/2012/039448, US/2013/0178612, WO/2012/073857, or US/2013/0253178, the phosphoramidites of each of which are hereby incorporated by reference.

In some embodiments, a phosphoramidite is stereochemically enriched. In some embodiments, a phosphoramidite is stereochemically pure. In some embodiments, a phosphoramidite is used for preparing chirally controlled oligonucleotide compositions, such as those described in in WO/2011/005761, US/2012/0316224, WO/2013/012758, US/2014/0194610, WO/2014/012081, US/2015/0211006, WO/2015/107425, US/2017/0037399, WO/2010/064146, US/2011/0294124, WO/2014/010250, US/2015/0197540, WO/2011/108682, US/2013/0184450, WO/2012/039448, US/2013/0178612, WO/2012/073857, or US/2013/0253178, the chirally controlled oligonucleotide compositions of each of which are hereby incorporated by reference.

In some embodiments, a phosphoramidite has the structure of formula I:

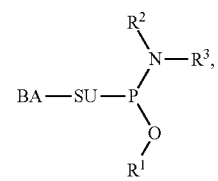

wherein each variable is independently as defined and described infra.

DETAILED DESCRIPTION OF CERTAIN EMBODIMENTS

1. Definitions

Figure 1:
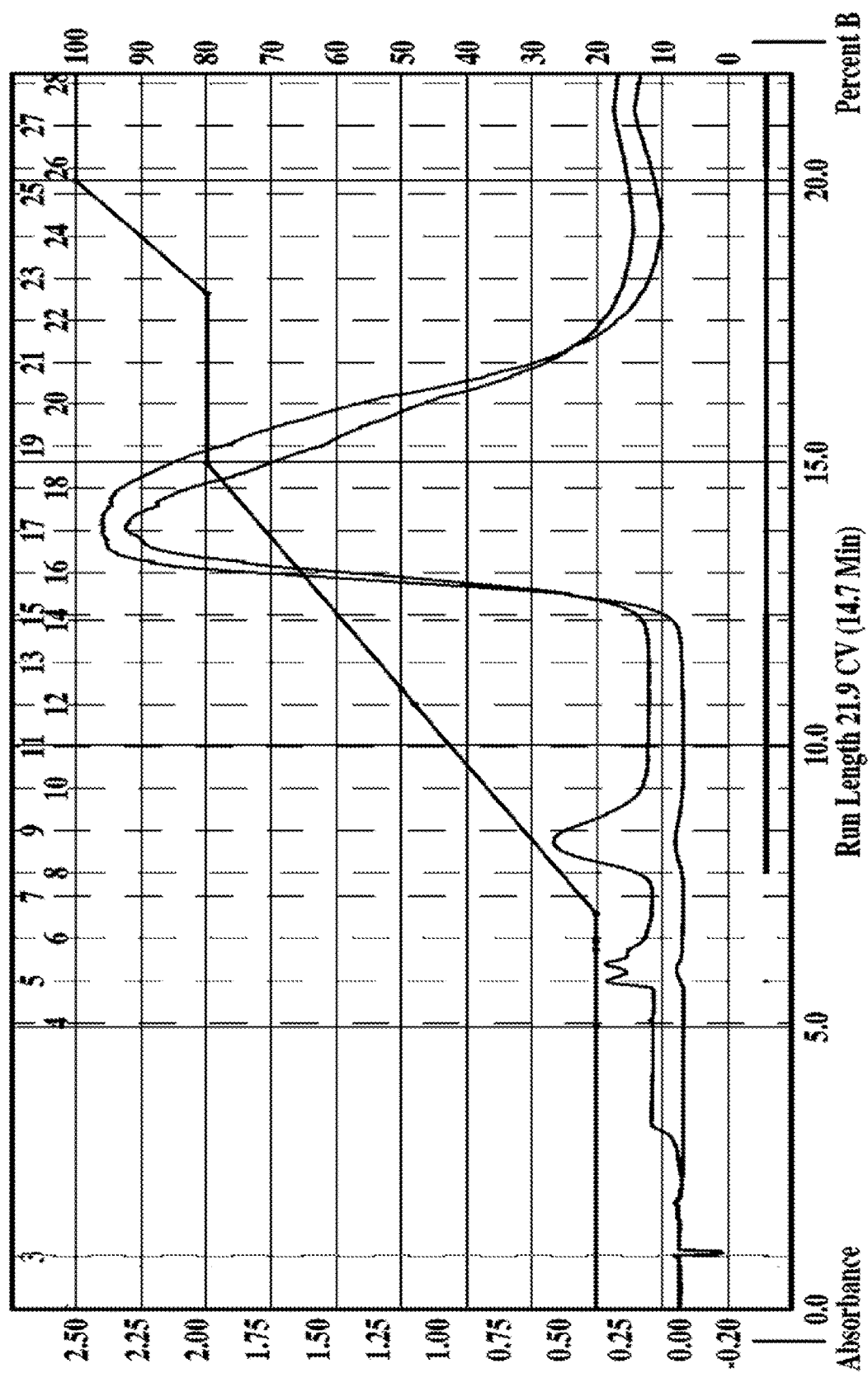
FIG. 1. Chromatogram: Non-pre-treated silica.
Figure 2:
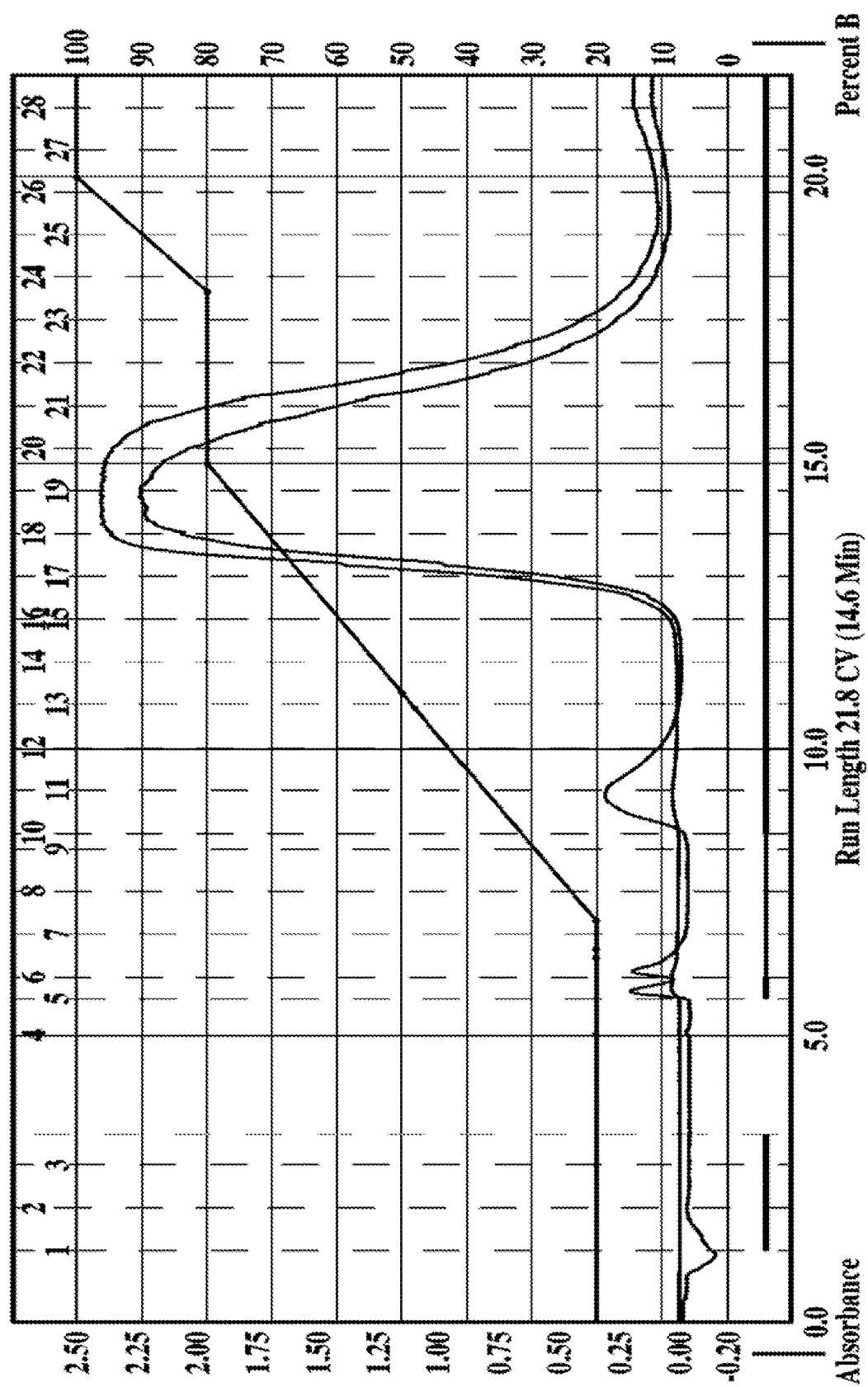
FIG. 2. Chromatogram: Pre-treated silica.

As used herein, the following definitions shall apply unless otherwise indicated. For purposes of this disclosure, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

Aliphatic: As used herein, "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation, or combinations thereof. Unless otherwise specified, aliphatic groups contain 1-100 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Alkenyl: As used herein, the term "alkenyl" refers to an alkyl group, as defined herein, having one or more double bonds.

Alkynyl: As used herein, the term "alkynyl" refers to an alkyl group, as defined herein, having one or more triple bonds.

Aryl: The term "aryl" used alone or as part of a larger moiety as in "aralkyl," "aralkoxy," or "aryloxyalkyl," refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term "aryl" may be used interchangeably with the term "aryl ring." In certain embodiments of the present disclosure, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like. In some embodiments, an aryl group has a radical or point of attachment on an aromatic ring.

Cycloaliphatic: The term "cycloaliphatic," as used herein, refers to saturated or partially unsaturated aliphatic monocyclic, bicyclic, or polycyclic ring systems having, e.g., from 3 to 30, members, wherein the aliphatic ring system is optionally substituted. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic" may also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

Halogen: The term "halogen" means F, Cl, Br, or I.

Heteroaliphatic: The term "heteroaliphatic" is given its ordinary meaning in the art and refers to aliphatic groups as described herein in which one or more carbon atoms is replaced with a heteroatom (e.g., oxygen, nitrogen, sulfur, silicon, phosphorus, and the like).

Heteroalkyl: The term "heteroalkyl" is given its ordinary meaning in the art and refers to alkyl groups as described herein in which one or more carbon atoms is replaced with a heteroatom (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

Heteroaryl: The terms "heteroaryl" and "heteroar-," used alone or as part of a larger moiety, e.g., "heteroaralkyl," or "heteroaralkoxy," refer to monocyclic, bicyclic or polycyclic ring systems having a total of five to thirty ring members, wherein at least one ring in the system is aromatic and at least one aromatic ring atom is a heteroatom. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or 14 it electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl group, wherein the alkyl and heteroaryl portions independently are optionally substituted.

Heteroatom: The term "heteroatom" means an atom that is not carbon or hydrogen. In some embodiments, a heteroatom is oxygen, sulfur, nitrogen, phosphorus, or silicon (including any oxidized form of nitrogen, sulfur, phosphorus, or silicon; the quaternized form of any basic nitrogen or a substitutable nitrogen of a heterocyclic ring (for example, N as in 3,4-dihydro-2H-pyrrolyl), NH (as in pyrrolidinyl) or $NR^+$ (as in N-substituted pyrrolidinyl); etc.).

Heterocyclyl: As used herein, the terms "heterocycle," "heterocyclyl," "heterocyclic radical," and "heterocyclic ring" are used interchangeably and refer to a monocyclic, bicyclic or polycyclic ring moiety (e.g., 3-30 membered) that is saturated or partially unsaturated and has one or more heteroatom ring atoms. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic or polycyclic. The term "heterocyclylalkyl" refers to an alkyl group substituted by a heterocyclyl, wherein the alkyl and heterocyclyl portions independently are optionally substituted.

Partially unsaturated: As used herein, the term "partially unsaturated" refers to a moiety that includes at least one double or triple bond. The term "partially unsaturated" is intended to encompass groups having multiple sites of unsaturation, but is not intended to include aryl or heteroaryl moieties.

Protecting Group: The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Siphenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Protected hydroxyl groups are well known in the art and include those described in detail in Protecting Groups in Organic Synthesis, T. W. Greene and P. G. M. Wuts, $3^{rd}$ edition, John Wiley & Sons, 1999, the entirety of which is incorporated herein by reference. Examples of suitably protected hydroxyl groups further include, but are not limited to, esters, carbonates, sulfonates, allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benznylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5] azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Substitution: As described herein, compounds of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents include halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}CH(OR°)_2$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$; —$(CH_2)_{0-4}O(CH_2)_{0-1}$-pyridyl which may be substituted with $R°$; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$, —$SC(S)SR°$; —$(CH_2)_{0-4}SC(O)R°$; —$(CH_2)_{0-4}C(O)NR°_2$; —$C(S)NR°_2$; —$C(S)SR°$;

—$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R°$; —$N(OR°)R°$; —$C(NH)NR°_2$;

—$P(O)_2R°$; —$P(O)R°_2$; —$OP(O)R°_2$; —$OP(O)(OR°)_2$; —$SiR°_3$; —$OSiR°_3$; —($C_{1-4}$ straight or branched alkylene)O—$N(R°)_2$; or —($C_{1-4}$ straight or branched alkylene)C(O)O—$N(R°)_2$, wherein each $R°$ may be substituted as defined below and is independently hydrogen, $C_{1-20}$ aliphatic, $C_{1-20}$ heteroaliphatic having 1-5 heteroatoms independently selected from nitrogen, oxygen, sulfur, silicon and phosphorus, —$CH_2$—($C_{6-14}$ aryl), —$O(CH_2)_{0-1}(C_{6-14}$ aryl), —$CH_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of $R°$, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on $R°$ (or the ring formed by taking two independent occurrences of $R°$ together with their intervening atoms), are independently halogen, —$(CH_2)_{0-2}R^{\bullet}$, -(halo$R^{\bullet}$), —$(CH_2)_{0-2}OH$, —$(CH_2)_{0-2}OR^{\bullet}$, —$(CH_2)_{0-2}CH(OR^{\bullet})_2$; —O(halo$R^{\bullet}$), —CN, —$N_3$, —$(CH_2)_{0-2}C(O)R^{\bullet}$, —$(CH_2)_{0-2}C(O)OH$, —$(CH_2)_{0-2}C(O)OR^{\bullet}$, —$(CH_2)_{0-2}SR^{\bullet}$, —$(CH_2)_{0-2}SH$, —$(CH_2)_{0-2}NH_2$, —$(CH_2)_{0-2}NHR^{\bullet}$, —$(CH_2)_{0-2}NR^{\bullet}_2$, —$NO_2$, —$SiR^{\bullet}_3$, —$OSiR^{\bullet}_3$, —$C(O)SR^{\bullet}$, —($C_{1-4}$ straight or branched alkylene)C(O)O$R^{\bullet}$, or —$SSR^{\bullet}$ wherein each $R^{\bullet}$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of $R°$ include =O and =S.

Suitable divalent substituents include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-4}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of $R^*$ include halogen, —$R^{\bullet}$, -(halo$R^{\bullet}$), —OH, —$OR^{\bullet}$, —O(halo$R^{\bullet}$), —CN, —C(O)OH, —C(O)$OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

In some embodiments, suitable substituents on a substitutable nitrogen include —$R^{\dagger}$, —$NR^{\dagger}_2$, —C(O)$R^{\dagger}$, —C(O)$OR^{\dagger}$, —C(O)C(O)$R^{\dagger}$, —C(O)$CH_2C(O)R^{\dagger}$, —$S(O)_2R^{\dagger}$, —$S(O)_2NR^{\dagger}_2$, C(S)$NR^{\dagger}_2$, —C(NH)$NR^{\dagger}_2$, or —$N(R^{\dagger})S(O)_2R^{\dagger}$; wherein each $R^{\dagger}$ is independently hydrogen, $C_{1-4}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of $R^{\dagger}$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of $R^{\dagger}$ are independently halogen, —$R^{\bullet}$, -(halo$R^{\bullet}$), —OH, —$OR^{\bullet}$, —O(halo$R^{\bullet}$), —CN, —C(O)OH, —C(O)$OR^{\bullet}$, —$NH_2$, —$NHR^{\bullet}$, —$NR^{\bullet}_2$, or —$NO_2$, wherein each $R^{\bullet}$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

Unsaturated: The term "unsaturated" as used herein, means that a moiety has one or more units of unsaturation.

2. Detailed Description of Certain Embodiments

Phosphoramidites have a variety of applications, for example, nucleoside phosphoramidites are widely used as monomers for oligonucleotide synthesis. Many technologies for preparing phosphoramidites suffer from low yield and/or purity. Among other things, such low yield and/or purity can lead to high cost and/or low quality of phosphoramidites, and any products downstream therefrom, for example, oligonucleotides prepared therefrom.

Among other things, the present disclosure encompasses the recognition that in some instances, a low yield and/or purity can be due to the purification process when a phosphoramidite is separated from other substances through, e.g., chromatography. In some embodiments, the present disclosure appreciates that one source of a problem with prior technologies that utilize chromatography purification (e.g., purification using silica gel, alumina, etc.) in preparation of phosphoramidites may be that a significant amount of phosphoramidite may be lost during chromatography. Without wishing to be bound by any particular theory, the present disclosure proposes that, in some instances, phosphoramidites may be lost through irreversible absorption/adsorption to a purification medium and/or decomposition when in contact with a purification medium during chromatography. In some embodiments, a phosphoramidite may be lost due to irreversible absorption/adsorption to a purification medium in that it cannot be readily eluted. In some embodiments, a phosphoramidite may decompose during chromatography purification. For example, as described in the exemplification section, in some embodiments, a phosphoramidite may decompose during purification using silica gel as a purification medium.

The low yield and/or purity of phosphoramidite, among other things, can significantly increase the cost of compositions made from them, particularly at large, process scale. In some embodiments, when they are used for oligonucleotide synthesis, the high cost of phosphoramidites can make oligonucleotides, compositions thereof and medicaments therefrom unusually expensive.

The present disclosure encompasses certain surprising findings, including that certain processes for pre-treating a purification medium can surprisingly improve utility and/or effectiveness of that medium, particularly for use in preparation of phosphoramidites. In some embodiments, such processes may be or comprise a deactivation process. In some embodiments, the pre-treatment is a deactivation process. In some embodiments, the pre-treatment comprises deactivation of a purification medium. In some embodiments, when a purification medium is deactivated, there is less irreversible absorption/adsorption and/or decomposition of phosphoramidites when such a purification medium is used for purification of phosphoramidites compared to the same, non-deactivated purification medium. In some embodiments, there is less irreversible absorption/adsorption. In some embodiments, there is less decomposition. In some embodiments, there is less irreversible absorption/adsorption and less decomposition. In some embodiments, a pre-treated medium provides higher recovery yield and/or purity of phosphoramidites than medium not pre-treated. In some embodiments, a pre-treated medium provides higher recovery yield. In some embodiments, a pre-treated medium provides higher purity. In some embodiments, a pre-treated medium provides higher recovery yield and higher purity.

In some embodiments, the pre-treatment may be or comprise removal or exclusion of water from a purification medium. In some embodiments, the pre-treatment comprises removal or exclusion of water from a purification medium. In some embodiments, the pre-treatment removes water from a purification medium. In some embodiments, the pre-treatment excludes water from a purification medium.

In some embodiments, the pre-treatment is performed mechanically. In some embodiments, a purification medium is pre-treated with heat. In some embodiments, a purification medium is pre-treated with vacuum. In some embodiments, a purification medium is pre-treated with heat and vacuum. In some embodiments, such mechanical pre-treatment processes deactivate the purification medium. As a person of ordinary skill in the art would appreciate, heat and/or vacuum can, among other things, remove water or other solvents from a purification medium in accordance with the present disclosure. In some embodiments, heating reaches a temperature of at least 50, 60, 70, 80, 90, 100, 110, 120, 130, 140, 150, 160, 170, 180, 190, 200, 250, 300, 400, or 500° C. In some embodiments, a vacuum is no more than 50 kPa, 40 kPa, 30 kPa, 20 kPa, 10 kPa, 5 kPa, 2 kPa, 1 kPa, 0.5 kPa, 0.2 kPa, 0.1 kPa, 50 Pa, 40 Pa, 30 Pa, 20 Pa, 10 Pa, 5 Pa, 2 Pa, 1 Pa, 0.5 Pa, 0.2 Pa, 0.1 Pa, 0.05 Pa, 0.02 Pa, or 0.01 Pa. In some embodiments, a treatment is for a prolonged time. In some embodiment, a treatment lasts 5 min, 10 min, 30 min, 1 hour, 2 hours, 4 hours, 6 hours, 10 hours, 12 hours, 16 hours, 24 hours, 36 hours, 48 hours or more.

In some embodiments, a purification medium is pre-treated with a first solvent system. In some embodiments, a first solvent system is or comprises a hygroscopic solvent. In some embodiments, a first solvent system is a hygroscopic solvent system. In some embodiments, a hygroscopic solvent system is a first solvent system as described in the present disclosure. In some embodiments, a first solvent system comprises a hygroscopic solvent. In some embodiments, a first solvent is a hygroscopic solvent. In some embodiments, a purification medium is deactivated by contacting the medium with a first solvent system. In some embodiments, a first solvent system comprises a water-miscible solvent. In some embodiments, a first solvent system comprises a water-miscible organic solvent. In some embodiments, a first solvent system is a water-miscible solvent. In some embodiments, a first solvent system is a water-miscible organic solvent. In some embodiments, a first solvent system comprises two or more solvents. In some embodiments, a first solvent system comprises two or more water-miscible solvents. In some embodiments, a first solvent system comprises two or more water-miscible organic solvents. Exemplary water-miscible organic solvent includes acetaldehyde, acetic acid, acetone, acetonitrile, 1,2-butanediol, 1,3-butanediol, 1,4-butanediol, 2-butoxyethanol, butyric acid, diethanolamine, diethylenetriamine, dimethylformamide, dimethoxyethane, dimethyl sulfoxide, 1,4-dioxane, ethanol, ethylamine, ethylene glycol, formic acid, furfuryl alcohol, glycerol, methanol, methyl diethanolamine, methyl isocyanide, 1-propanol, 1,3-propanediol, 1,5-pentanediol, 2-propanol, propanoic acid, propylene glycol, pyridine, tetrahydrofuran, triethylene glycol, etc.

In some embodiments, a first solvent system comprises a hygroscopic solvent. In some embodiments, a first solvent system is a hygroscopic solvent. In some embodiments, a first solvent system comprises two or more hygroscopic solvents, e.g., a hygroscopic solvent system which is a mixture of two or more hygroscopic solvents, a hygroscopic solvent system comprises two or more hygroscopic solvents and one or more dry, non-hygroscopic solvents. In some embodiments, a first hygroscopic solvent is a water-miscible solvent. In some embodiments, a hygroscopic solvent is a water-miscible organic solvent. In some embodiments, as a person having ordinary skill in the art appreciates, a hygroscopic solvent system can absorb water from its environment, for example, when contacted with a purification medium, a hygroscopic solvent system can absorb water, if any, from the purification medium. When run through a column packed with a purification medium as a stationary phase, a hygroscopic solvent may remove water from the purification medium. In some embodiments, a hygroscopic solvent used for deactivation may contain no more than 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% of water (v/v). In some embodiments, a hygroscopic solvent is used as an anhydrous solvent directly purchased from commercial vendors (e.g., Sigma-Aldrich, Acros Organics, etc.). Alternatively or additionally, a hygroscopic solvent can be further purified and/or dried according to known protocols in the art.

A number of hygroscopic solvents can be used in a provided solvent system, e.g., a first solvent system, a hygroscopic solvent system, etc., in accordance with the present disclosure. In some embodiments, a hygroscopic solvent is an alcohol. In some embodiments, a hygroscopic solvent is methanol. In some embodiments, a hygroscopic solvent is ethanol. In some embodiments, a hygroscopic solvent is isopropyl alcohol. In some embodiments, a hygroscopic solvent is acetone. In some embodiments, a hygroscopic solvent is acetonitrile. In some embodiments, a hygroscopic solvent is dimethyl carbonate. In some embodiments, a hygroscopic solvent is ethyl acetate. In some embodiments, a hygroscopic solvent is a solvent more hygroscopic than chloroform. In some embodiments, a hygroscopic solvent is a solvent more hygroscopic than methylene chloride. In some embodiments, a hygroscopic solvent is a solvent more hygroscopic than ethyl acetate. In some embodiments, a hygroscopic solvent is a solvent more hygroscopic than acetone. In some embodiments, a hygroscopic solvent is a solvent more hygroscopic than acetonitrile. In some embodiments, a hygroscopic solvent is a solvent more hygroscopic than dimethyl carbonate. In some embodiments, a hygroscopic solvent is a solvent more hygroscopic than methanol. In some embodiments, a hygroscopic solvent is a solvent more hygroscopic than ethanol. In some embodiments, a hygroscopic solvent is a solvent more hygroscopic than isopropanol. In some embodiments, a hygroscopic solvent is a solvent no less hygroscopic than chloroform. In some embodiments, a hygroscopic solvent is a solvent no less hygroscopic than methylene chloride. In some embodiments, a hygroscopic solvent is a solvent no less hygroscopic than ethyl acetate. In some embodiments, a hygroscopic solvent is a solvent no less hygroscopic than acetone. In some embodiments, a hygroscopic solvent is a solvent no less hygroscopic than acetonitrile. In some embodiments, a hygroscopic solvent is a solvent no less hygroscopic than dimethyl carbonate. In some embodiments, a hygroscopic solvent is a solvent no less hygroscopic than methanol. In some embodiments, a hygroscopic solvent is a solvent no less hygroscopic than ethanol. In some embodiments, a hygroscopic solvent is a solvent no less hygroscopic than isopropanol.

In some embodiments, a first solvent system comprises an alcohol. In some embodiments, a first solvent system is an alcohol. In some embodiments, a first solvent system comprises an alcohol and another organic solvent. In some embodiments, a first solvent system comprises at least 10% (v/v) alcohol. In some embodiments, a first solvent system comprises at least 20% (v/v) alcohol. In some embodiments, a first solvent system comprises at least 30% (v/v) alcohol. In some embodiments, a first solvent system comprises at least 40% (v/v) alcohol. In some embodiments, a first solvent system comprises at least 50% (v/v) alcohol. In some embodiments, a first solvent system comprises at least 60% (v/v) alcohol. In some embodiments, a first solvent system comprises at least 70% (v/v) alcohol. In some embodiments, a first solvent system comprises at least 80% (v/v) alcohol. In some embodiments, a first solvent system comprises at least 90% (v/v) alcohol. In some embodiments, a first solvent system comprises at least 95% (v/v) alcohol. In some embodiments, a first solvent system comprises at least 96% (v/v) alcohol. In some embodiments, a first solvent system comprises at least 97% (v/v) alcohol. In some embodiments, a first solvent system comprises at least 98% (v/v) alcohol. In some embodiments, a first solvent system comprises at least 99% (v/v) alcohol. In some embodiments, an alcohol is a $C_{1-6}$ alcohol. In some embodiments, an alcohol is methanol. In some embodiments, an alcohol is an ethanol. In some embodiments, an alcohol is isopropanol. In some embodiments, an alcohol is 1-propanol. In some embodiments, an alcohol is a butanol.

In some embodiments, a first solvent system comprises methanol. In some embodiments, a first solvent system is methanol. In some embodiments, a first solvent system comprises at least 10% (v/v) methanol. In some embodiments, a first solvent system comprises at least 20% (v/v) methanol. In some embodiments, a first solvent system comprises at least 30% (v/v) methanol. In some embodiments, a first solvent system comprises at least 40% (v/v) methanol. In some embodiments, a first solvent system comprises at least 50% (v/v) methanol. In some embodiments, a first solvent system comprises at least 60% (v/v) methanol. In some embodiments, a first solvent system comprises at least 70% (v/v) methanol. In some embodiments, a first solvent system comprises at least 80% (v/v) methanol. In some embodiments, a first solvent system comprises at least 90% (v/v) methanol. In some embodiments, a first solvent system comprises at least 95% (v/v) methanol. In some embodiments, a first solvent system comprises at least 96% (v/v) methanol. In some embodiments, a first solvent system comprises at least 97% (v/v) methanol. In some embodiments, a first solvent system comprises at least 98% (v/v) methanol. In some embodiments, a first solvent system comprises at least 99% (v/v) methanol. In some embodiments, a first solvent system is methanol.

In some embodiments, a first solvent system comprises ethanol. In some embodiments, a first solvent system is ethanol. In some embodiments, a first solvent system comprises at least 10% (v/v) ethanol. In some embodiments, a first solvent system comprises at least 20% (v/v) ethanol. In some embodiments, a first solvent system comprises at least 30% (v/v) ethanol. In some embodiments, a first solvent system comprises at least 40% (v/v) ethanol. In some embodiments, a first solvent system comprises at least 50% (v/v) ethanol. In some embodiments, a first solvent system comprises at least 60% (v/v) ethanol. In some embodiments, a first solvent system comprises at least 70% (v/v) ethanol. In some embodiments, a first solvent system comprises at least 80% (v/v) ethanol. In some embodiments, a first solvent system comprises at least 90% (v/v) ethanol. In some embodiments, a first solvent system comprises at least 95% (v/v) ethanol. In some embodiments, a first solvent system comprises at least 96% (v/v) ethanol. In some embodiments, a first solvent system comprises at least 97% (v/v) ethanol. In some embodiments, a first solvent system comprises at least 98% (v/v) ethanol. In some embodiments, a first solvent system comprises at least 99% (v/v) ethanol. In some embodiments, a first solvent system is ethanol.

In some embodiments, a first solvent system comprises 1-propanol. In some embodiments, a first solvent system is 1-propanol. In some embodiments, a first solvent system comprises at least 10% (v/v) 1-propanol. In some embodiments, a first solvent system comprises at least 20% (v/v) 1-propanol. In some embodiments, a first solvent system comprises at least 30% (v/v) 1-propanol. In some embodiments, a first solvent system comprises at least 40% (v/v) 1-propanol. In some embodiments, a first solvent system comprises at least 50% (v/v) 1-propanol. In some embodiments, a first solvent system comprises at least 60% (v/v) 1-propanol. In some embodiments, a first solvent system comprises at least 70% (v/v) 1-propanol. In some embodiments, a first solvent system comprises at least 80% (v/v) 1-propanol. In some embodiments, a first solvent system comprises at least 90% (v/v) 1-propanol. In some embodiments, a first solvent system comprises at least 95% (v/v) 1-propanol. In some embodiments, a first solvent system comprises at least 96% (v/v) 1-propanol. In some embodiments, a first solvent system comprises at least 97% (v/v) 1-propanol. In some embodiments, a first solvent system comprises at least 98% (v/v) 1-propanol. In some embodiments, a first solvent system comprises at least 99% (v/v) 1-propanol. In some embodiments, a first solvent system is 1-propanol.

In some embodiments, a first solvent system comprises isopropanol. In some embodiments, a first solvent system is isopropanol. In some embodiments, a first solvent system comprises at least 10% (v/v) isopropanol. In some embodiments, a first solvent system comprises at least 20% (v/v) isopropanol. In some embodiments, a first solvent system comprises at least 30% (v/v) isopropanol. In some embodiments, a first solvent system comprises at least 40% (v/v) isopropanol. In some embodiments, a first solvent system comprises at least 50% (v/v) isopropanol. In some embodiments, a first solvent system comprises at least 60% (v/v) isopropanol. In some embodiments, a first solvent system comprises at least 70% (v/v) isopropanol. In some embodiments, a first solvent system comprises at least 80% (v/v) isopropanol. In some embodiments, a first solvent system comprises at least 90% (v/v) isopropanol. In some embodiments, a first solvent system comprises at least 95% (v/v) isopropanol. In some embodiments, a first solvent system comprises at least 96% (v/v) isopropanol. In some embodiments, a first solvent system comprises at least 97% (v/v) isopropanol. In some embodiments, a first solvent system comprises at least 98% (v/v) isopropanol. In some embodiments, a first solvent system comprises at least 99% (v/v) isopropanol. In some embodiments, a first solvent system is isopropanol.

In some embodiments, a first solvent system comprises acetone. In some embodiments, a first solvent system is acetone. In some embodiments, a first solvent system comprises at least 10% (v/v) acetone. In some embodiments, a first solvent system comprises at least 20% (v/v) acetone. In some embodiments, a first solvent system comprises at least 30% (v/v) acetone. In some embodiments, a first solvent system comprises at least 40% (v/v) acetone. In some embodiments, a first solvent system comprises at least 50% (v/v) acetone. In some embodiments, a first solvent system comprises at least 60% (v/v) acetone. In some embodiments, a first solvent system comprises at least 70% (v/v) acetone. In some embodiments, a first solvent system comprises at least 80% (v/v) acetone. In some embodiments, a first solvent system comprises at least 90% (v/v) acetone. In some embodiments, a first solvent system comprises at least 95% (v/v) acetone. In some embodiments, a first solvent system comprises at least 96% (v/v) acetone. In some embodiments, a first solvent system comprises at least 97% (v/v) acetone. In some embodiments, a first solvent system comprises at least 98% (v/v) acetone. In some embodiments, a first solvent system comprises at least 99% (v/v) acetone. In some embodiments, a first solvent system is acetone.

In some embodiments, a first solvent system comprises acetonitrile. In some embodiments, a first solvent system is acetonitrile. In some embodiments, a first solvent system comprises at least 10% (v/v) acetonitrile. In some embodiments, a first solvent system comprises at least 20% (v/v) acetonitrile. In some embodiments, a first solvent system comprises at least 30% (v/v) acetonitrile. In some embodiments, a first solvent system comprises at least 40% (v/v) acetonitrile. In some embodiments, a first solvent system comprises at least 50% (v/v) acetonitrile. In some embodiments, a first solvent system comprises at least 60% (v/v) acetonitrile. In some embodiments, a first solvent system comprises at least 70% (v/v) acetonitrile. In some embodiments, a first solvent system comprises at least 80% (v/v) acetonitrile. In some embodiments, a first solvent system comprises at least 90% (v/v) acetonitrile. In some embodiments, a first solvent system comprises at least 95% (v/v) acetonitrile. In some embodiments, a first solvent system comprises at least 96% (v/v) acetonitrile. In some embodiments, a first solvent system comprises at least 97% (v/v) acetonitrile. In some embodiments, a first solvent system comprises at least 98% (v/v) acetonitrile. In some embodiments, a first solvent system comprises at least 99% (v/v) acetonitrile. In some embodiments, a first solvent system is acetonitrile.

In some embodiments, a first solvent system comprises dimethyl carbonate. In some embodiments, a first solvent system is dimethyl carbonate. In some embodiments, a first solvent system comprises at least 10% (v/v) dimethyl carbonate. In some embodiments, a first solvent system comprises at least 20% (v/v) dimethyl carbonate. In some embodiments, a first solvent system comprises at least 30% (v/v) dimethyl carbonate. In some embodiments, a first solvent system comprises at least 40% (v/v) dimethyl carbonate. In some embodiments, a first solvent system comprises at least 50% (v/v) dimethyl carbonate. In some embodiments, a first solvent system comprises at least 60% (v/v) dimethyl carbonate. In some embodiments, a first solvent system comprises at least 70% (v/v) dimethyl carbonate. In some embodiments, a first solvent system comprises at least 80% (v/v) dimethyl carbonate. In some embodiments, a first solvent system comprises at least 90% (v/v) dimethyl carbonate. In some embodiments, a first solvent system comprises at least 95% (v/v) dimethyl carbonate. In some embodiments, a first solvent system comprises at least 96% (v/v) dimethyl carbonate. In some embodiments, a first solvent system comprises at least 97% (v/v) dimethyl carbonate. In some embodiments, a first solvent system comprises at least 98% (v/v) dimethyl carbonate. In some embodiments, a first solvent system comprises at least 99% (v/v) dimethyl carbonate. In some embodiments, a first solvent system is dimethyl carbonate.

In some embodiments, a first solvent system comprises ethyl acetate. In some embodiments, a first solvent system is ethyl acetate. In some embodiments, a first solvent system comprises at least 10% (v/v) ethyl acetate. In some embodiments, a first solvent system comprises at least 20% (v/v) ethyl acetate. In some embodiments, a first solvent system comprises at least 30% (v/v) ethyl acetate. In some embodiments, a first solvent system comprises at least 40% (v/v) ethyl acetate. In some embodiments, a first solvent system comprises at least 50% (v/v) ethyl acetate. In some embodiments, a first solvent system comprises at least 60% (v/v) ethyl acetate. In some embodiments, a first solvent system comprises at least 70% (v/v) ethyl acetate. In some embodiments, a first solvent system comprises at least 80% (v/v) ethyl acetate. In some embodiments, a first solvent system comprises at least 90% (v/v) ethyl acetate. In some embodiments, a first solvent system comprises at least 95% (v/v) ethyl acetate. In some embodiments, a first solvent system comprises at least 96% (v/v) ethyl acetate. In some embodiments, a first solvent system comprises at least 97% (v/v) ethyl acetate. In some embodiments, a first solvent system comprises at least 98% (v/v) ethyl acetate. In some embodiments, a first solvent system comprises at least 99% (v/v) ethyl acetate. In some embodiments, a first solvent system is ethyl acetate.

In some embodiments, a first solvent is hygroscopic. In some embodiments, a first solvent is hygroscopic in that it comprises a hygroscopic solvent. In some embodiments, a first solvent is hygroscopic in that it is a hygroscopic solvent. In some embodiments, a first solvent is hygroscopic in that it is a hygroscopic solution. In some embodiments, a hygroscopic solution comprises an organic solvent and a hygroscopic solute.

In some embodiments, a first solvent system optionally comprises a modifier. In some embodiments, a first solvent system comprises a modifier. In some embodiments, a first solvent system comprises no modifier.

Those skilled in the art appreciate that many mobile phase modifiers can be utilized in accordance with the present disclosure to, e.g., modify certain properties of a solvent system as mobile phase. In some embodiments, a modifier is a base. In some embodiments, a modifier is ammonia. In some embodiments, a modifier is triethylamine. In some embodiments, a modifier is an acid. In some embodiments, a modifier is formic acid. A modifier can be added in various amount, for example, about 0.05%, 0.1%, 0.2%, 0.3%, 0.4%, 0.5%, 0.6%, 0.7%, 0.8%, 0.9%, 1%, 1.5%, 2%, 2.5%, 3%, 3.5%, 4%, 4.5%, 5%, 6%, 7%, 8%, 9%, 10%, 20%, 30%, 40%, 50%, or more (v/v).

In some embodiments, a first solvent system removes water from a purification medium. In some embodiments, a first solvent may react with reactive sites of a purification medium and deactivates a purification medium, so that compounds such as phosphoramidites decompose less when contacted with the purification medium. In some embodiments, a first solvent system may provide pre-treatment by heat. For example, when methanol is contacted with silica gel, heat may be generated.

A person of ordinary skill in the art will appreciate that various procedures can be used to pre-treat a purification medium in accordance to provided methods. For example, a first solvent system can be run through a column packed with a purification medium as stationary phase to pre-treat the stationary phase. In some embodiments, 1, 2, 3, 4, 5, 6, 7, 8, 9, 10 or more column volumes of a first solvent system is run through a column to pre-treat the purification medium.

In some embodiments, the present disclosure demonstrate that provided pre-treatment process, including those that were previously understood or expected to degrade or otherwise damage or wash out a purification medium during chromatography, can in fact improve utility and/or effectiveness of such a medium, particularly in the purification and/or preparation of phosphoramidites. For example, at the time of the present disclosure it is generally taught that high percentage of certain alcohols, such as methanol, should not be run through columns packed with certain purification media, for example, silica gel. As exemplified by the present disclosure, however, pure methanol can be run through silica columns, and silica pre-treated with methanol can provide unexpectedly higher yield and/or purity of phosphoramidites compared to non-pre-treated silica.

In some embodiments, a provided method comprises an equilibration process after a pre-treatment process. In some embodiments, an equilibration process comprises contacting a pre-treated purification medium with a second solvent system. In some embodiments, a second solvent system is less polar than the first solvent system used to pre-treat the purification medium.

In some embodiments, a second solvent system consists of one solvent and optionally a modifier. In some embodiments, a second solvent system comprises two or more solvents and optionally a modifier. In some embodiments, a modifier is a base. In some embodiments, a modifier is triethylamine.

In some embodiments, a second solvent system comprises an isocratic system during the equilibration process. In some embodiments, a second solvent system is isocratic during the equilibration process. In some embodiments, a second solvent system comprises a gradient system. In some embodiments, a second solvent system is a gradient system. In some embodiments, the equilibration process comprises a first isocratic process, a gradient process, and optionally a second isocratic process. In some embodiments, the gradient process starts with the first isocratic process and ends with the second isocratic process. In some embodiments, the second isocratic process uses a more polar solvent system that the first one, e.g., containing more ethyl acetate in for an ethyl acetate/hexanes system. In some embodiments, the second isocratic process uses a less polar solvent system that the first one, e.g., containing less ethyl acetate for an ethyl acetate/hexanes system. In some embodiments, the first isocratic process for equilibration uses the same solvent system as the first solvent system.

In some embodiments, a second solvent system comprises ethyl acetate. In some embodiments, a second solvent system comprises ethyl acetate and triethylamine as a modifier. In some embodiments, a second solvent system comprises hexanes. In some embodiments, a second solvent system comprises hexanes and triethylamine as a modifier. In some embodiments, a second solvent system comprises hexanes and ethyl acetate. In some embodiments, a second solvent system is a mixture of hexanes and ethyl acetate. In some embodiments, a second solvent system comprises hexanes, ethyl acetate, and triethylamine. In some embodiments, a second solvent system is a mixture of hexanes, ethyl acetate, and triethylamine. In some embodiments, a second solvent system is 20% ethyl acetate in ethyl acetate/hexanes with 5% triethylamine.

A person of ordinary skill in the art appreciates that a variety of methods can be used to equilibrate a purification medium. In some embodiments, for a column packed with a purification medium as stationary phase, about 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10 or more column volume of a second solvent system (including isocratic and/or gradient) is run through the column for equilibration a pre-treated purification medium.

In some embodiments, after an equilibration process, a phosphoramidite is loaded to the pre-treated and equilibrated purification medium, and a third solvent system is utilized to elute, separate and/or purify the phosphoramidite. A person of ordinary skill in the art appreciates that many suitable solvent systems can be employed as a third solvent system in accordance with the present disclosure. In some embodiments, a third solvent system is less polar than the first solvent system. In some embodiments, a third solvent system is the same as the second solvent system for equilibration. In some embodiments, a third solvent system is the same as the second solvent system at the end of the equilibration process.

In some embodiments, a third solvent system consists of one solvent and optionally a modifier. In some embodiments, a third solvent system comprises two or more solvents and optionally a modifier. In some embodiments, a modifier is a base. In some embodiments, a modifier is triethylamine.

In some embodiments, a third solvent system comprises an isocratic system during the elution process. In some embodiments, a third solvent system is isocratic during the elution process. In some embodiments, a third solvent system comprises a gradient system. In some embodiments, a third solvent system is a gradient system. In some embodiments, the elution process comprises a first isocratic process, a gradient process, and optionally a second isocratic process. In some embodiments, the gradient process starts with the first isocratic process and ends with the second isocratic process. In some embodiments, the second isocratic process uses a more polar solvent system that the first one, e.g., containing more ethyl acetate for an ethyl acetate/hexanes system. In some embodiments, the first isocratic elution process uses the same solvent system as the solvent system at the end of the equilibration process. In some embodiments, the elution process comprises two or more first isocratic-gradient-second isocratic processes as illustrated in the examples.

In some embodiments, a third solvent system comprises ethyl acetate. In some embodiments, a third solvent system comprises ethyl acetate and a base as a modifier. In some embodiments, a third solvent system comprises ethyl acetate and an amine as a modifier. In some embodiments, a third solvent system comprises ethyl acetate and triethylamine as a modifier. In some embodiments, a third solvent system comprises hexanes. In some embodiments, a third solvent system comprises hexanes and triethylamine as a modifier. In some embodiments, a third solvent system comprises hexanes and ethyl acetate. In some embodiments, a third solvent system is a mixture of hexanes and ethyl acetate. In some embodiments, a third solvent system comprises hexanes, ethyl acetate, and triethylamine. In some embodiments, a third solvent system is a mixture of hexanes, ethyl acetate, and triethylamine. Exemplary solvent systems for elution are illustrated in the examples.

A person of ordinary skill in the art appreciates that a variety of methods can be used to elute, separate and/or purity a phosphoramidite. In some embodiments, for a column packed with a purification medium as stationary phase, about 0.1, 0.2, 0.3, 0.4, 0.5, 0.6, 0.7, 0.8, 0.9, 1, 1.5, 2, 2.5, 3, 3.5, 4, 4.5, 5, 6, 7, 8, 9, 10, 15, 20, 25, 30, 40, 50, 60, 70, 80, 90, 100 or more column volume of a third solvent system (including isocratic and/or gradient) is run through the column.

Those skilled in the art appreciate that various purification media can be used for purification of phosphoramidites, and can be pre-treated, equilibrated and/or eluted using provided methods to improve yields and/or purity of phosphoramidites in accordance with the present disclosure. In some embodiments, a purification medium is a silica medium. In some embodiments, a purification medium is silica gel. In some embodiments, a purification medium is alumina. In some embodiments, a purification medium is basis alumina. In some embodiments, a purification medium can be used for other purposes other than purification.

Purification media of various particle sizes can be pre-treated and utilized according to the present disclosure. In some embodiments, a particle size is about 5, 10, 15, 20, 25, 30, 35, 40, 45, 50, 55, 60, 70, 80, 90, 100, 150, 200, or more micrometer in diameter. In some embodiments, a particle size is less than about 5, 10, 15, 20, 25, 30, 35, 40, 45, 50, 55, 60, 70, 80, 90, 100, 150, or 200 micrometer in diameter. In some embodiments, a particle size is greater than about 5, 10, 15, 20, 25, 30, 35, 40, 45, 50, 55, 60, 70, 80, 90, 100, 150 or 200 micrometer in diameter. In some embodiments, a purification medium is silica of about 10 micrometer in diameter. In some embodiments, a purification medium is silica of about 15 micrometer in diameter. In some embodiments, a purification medium is silica of about 20 micrometer in diameter. In some embodiments, a purification medium is silica of about 25 micrometer in diameter. In some embodiments, a purification medium is silica of about 30 micrometer in diameter. In some embodiments, a purification medium is silica of about 35 micrometer in diameter. In some embodiments, a purification medium is silica of about 40 micrometer in diameter. In some embodiments, a purification medium is silica of about 45 micrometer in diameter. In some embodiments, a purification medium is silica of about 50 micrometer in diameter. In some embodiments, a purification medium is silica of about 60 micrometer in diameter. In some embodiments, a purification medium is silica of about 70 micrometer in diameter. In some embodiments, a purification medium is silica of about 80 micrometer in diameter. In some embodiments, a purification medium is silica of about 90 micrometer in diameter. In some embodiments, a purification medium is silica of about 100 micrometer in diameter. In some embodiments, a purification medium is silica of greater than about 100 micrometer in diameter.

In some embodiments, a purification medium is packed into a column. In some embodiments, a purification medium is silica gel. In some embodiments, several column volumes of methanol are passed through the column to deactivate the silica gel. In some embodiments, several column volumes of mixtures of ethyl acetate and hexanes with triethylamine as modifier are used to equilibrate the treated silica gel before crude phosphoramidite is loaded. In some embodiments, phosphoramidite is eluted with mixtures of ethyl acetate and hexanes with triethylamine as modifier.

In some embodiments, the present disclosure provides a composition comprising a pre-treated purification medium as described herein, and a phosphoramidite. In some embodiments, the present disclosure provides a composition comprising a pre-treated and equilibrated purification medium as described herein, and a phosphoramidite. In some embodiments, a purification medium is silica gel. In some embodiments, the silica gel is pre-treated with an alcohol. In some embodiments, the silica gel is pre-treated with methanol. In some embodiments, the silica gel is equilibrated with a solvent system comprising hexanes. In some embodiments, the silica gel is equilibrated with a solvent system comprising ethyl acetate. In some embodiments, the silica gel is equilibrated with a solvent system comprises ethyl acetate and hexanes. In some embodiments, the silica gel is equilibrated with a solvent system consisting of ethyl acetate and hexanes. In some embodiments, the silica gel is equilibrated with a solvent system comprising ethyl acetate, hexanes and triethylamine. In some embodiments, the silica gel is equilibrated with a solvent system consisting of ethyl acetate, hexanes and triethylamine. In some embodiments, the silica gel is equilibrated, wherein the equilibration comprises contact with hexanes. In some embodiments, the silica gel is equilibrated, wherein the equilibration comprises contact with ethyl acetate. In some embodiments, the silica gel is equilibrated, wherein the equilibration comprises contact with triethylamine. In some embodiments, the silica gel is equilibrated, wherein the equilibration comprises contact with hexanes and ethyl acetate. In some embodiments, the silica gel is equilibrated, wherein the equilibration comprises contact with hexanes and triethylamine. In some embodiments, the silica gel is equilibrated, wherein the equilibration comprises contact with ethyl acetate and triethylamine. In some embodiments, the silica gel is equilibrated, wherein the equilibration comprises contact with hexane, ethyl acetate and triethylamine. In some embodiments, the silica gel is equilibrated, wherein the equilibration consists of contact with hexane, ethyl acetate and triethylamine.

In some embodiments, a phosphoramidite is a nucleoside phosphoramidite.

In some embodiments, a phosphoramidite has the structure of formula I:

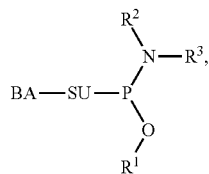

I wherein:

BA is R, or an optionally substituted group selected from a 3-30 membered cycloaliphatic ring, a 6-30 membered aryl ring, a 3-30 membered heterocyclyl having 1-10 heteroatoms independently selected from oxygen, nitrogen, sulfur, phosphorus and silicon, a 5-30 membered heteroaryl ring having 1-10 heteroatoms independently selected from oxygen, nitrogen, sulfur, phosphorus and silicon, a natural nucleobase moiety and a modified nucleobase moiety;

SU is a sugar moiety, a modified sugar moiety, -L-O— or

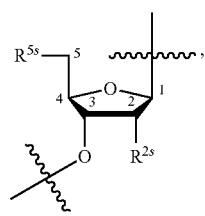

wherein SU is connected to the phosphorus atom in formula I through the oxygen atom;

L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

$R^{5s}$ is R' or —OR';

$R^{2s}$ is —F, —CN, —N$_3$, —NO, —NO$_2$, —R'—OR', —SR', —N(R')$_2$, -L-R', —O-L-OR', —O-L-SR', or —O-L-N(R')$_2$, or $R^{2s}$ is L connecting C2 with C1, C2, C3, C4 or C5;

-Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;

each of $R^1$, $R^2$, and $R^3$ is independently R', or two or three of $R^1$, $R^2$, and $R^3$ are taken together with their intervening atoms to form:

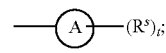

Ring A is an optionally substituted multivalent, monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon;

each $R^s$ is independently R' or -L-R';

t is 0-5;

each R' is independently —R, —C(O)R, —CO$_2$R, or —SO$_2$R, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, a 6-30 membered aryl ring, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

In some embodiments, a phosphoramidite has the structure of formula I:

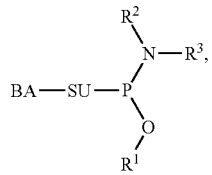

I wherein:
BA is an optionally substituted group selected from $C_{1-30}$ cycloaliphatic, $C_{6-30}$ aryl, $C_{3-30}$ heterocyclyl having 1-10 heteroatoms independently selected from oxygen, nitrogen, sulfur, phosphorus and silicon, $C_{5-30}$ heteroaryl having 1-10 heteroatoms independently selected from oxygen, nitrogen, sulfur, phosphorus and silicon, a natural nucleobase moiety and a modified nucleobase moiety;
SU is -L-O— or

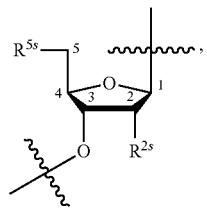

wherein SU is connected to the phosphorus atom in formula I through the oxygen atom;
L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
$R^{5s}$ is R' or —OR;
$R^{2s}$ is —F, —CN, —N$_3$, —NO, —NO$_2$, —R'—OR, —SR', —N(R')$_2$, —O-L-OR', —O-L-SR', or —O-L-N(R')$_2$, or $R^{2s}$ is L connecting C2 with C1, C2, C3, C4 or C5;
-Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;
each of $R^1$, $R^2$, and $R^3$ is independently R', or two or three of $R^1$, $R^2$, and $R^3$ are taken together with their intervening atoms to form:

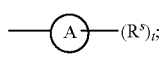

Ring A is an optionally substituted multivalent, monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon;
each $R^s$ is independently R' or -L-R';
t is 0-5;
each R' is independently —R, —C(O)R, —CO$_2$R, or —SO$_2$R, or:
two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and
each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

In some embodiments, BA is an optionally substituted group selected from a 3-30 membered cycloaliphatic ring, a 6-30 membered aryl ring, a 3-30 membered heterocyclyl having 1-10 heteroatoms independently selected from oxygen, nitrogen, sulfur, phosphorus and silicon, a 5-30 membered heteroaryl ring having 1-10 heteroatoms independently selected from oxygen, nitrogen, sulfur, phosphorus and silicon, a natural nucleobase moiety and a modified nucleobase moiety. In some embodiments, BA is optionally substituted $C_{1-30}$ cycloaliphatic. In some embodiments, BA is optionally substituted $C_{6-30}$ aryl. In some embodiments, BA is optionally substituted 3-30 membered heterocyclyl. In some embodiments, BA is optionally substituted $C_{3-30}$ heterocyclyl. In some embodiments, BA is optionally substituted 5-30 membered heteroaryl. In some embodiments, BA is optionally substituted $C_{5-30}$ heteroaryl. In some embodiments, BA is an optionally substituted natural base moiety. In some embodiments, BA is an optionally substituted modified base moiety. In some embodiments, BA is an optionally substituted group selected from $C_{1-30}$ cycloaliphatic, $C_{6-30}$ aryl, $C_{3-30}$ heterocyclyl, and $C_{5-30}$ heteroaryl. In some embodiments, BA is an optionally substituted group selected from $C_{1-30}$ cycloaliphatic, $C_{6-30}$ aryl, $C_{3-30}$ heterocyclyl, $C_{5-30}$ heteroaryl, and a natural nucleobase moiety. In some embodiments, BA is optionally substituted A, T, C, or G. In some embodiments, BA is A, T, C, G, or 5-mC.

In some embodiments, BA is connected to SU through an aromatic ring. In some embodiments, BA is connected to SU through a heteroatom. In some embodiments, BA is connected to SU through a ring heteroatom of an aromatic ring. In some embodiments, BA is connected to SU through a ring nitrogen atom of an aromatic ring. In some embodiments, a connection is as one found in natural nucleoside.

In some embodiments, BA is a natural nucleobase moiety. In some embodiments, BA is an optionally substituted natural nucleobase moiety. In some embodiments, BA is a substituted natural nucleobase moiety.

In some embodiments, BA is an optionally substituted group, which group is formed by removing a —H from

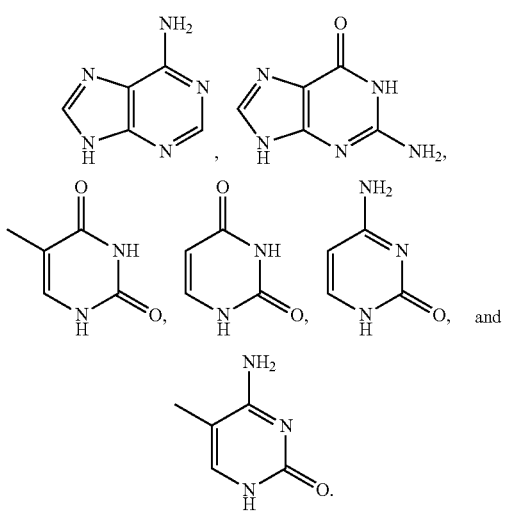

In some embodiments, BA is an optionally substituted group which group is selected from

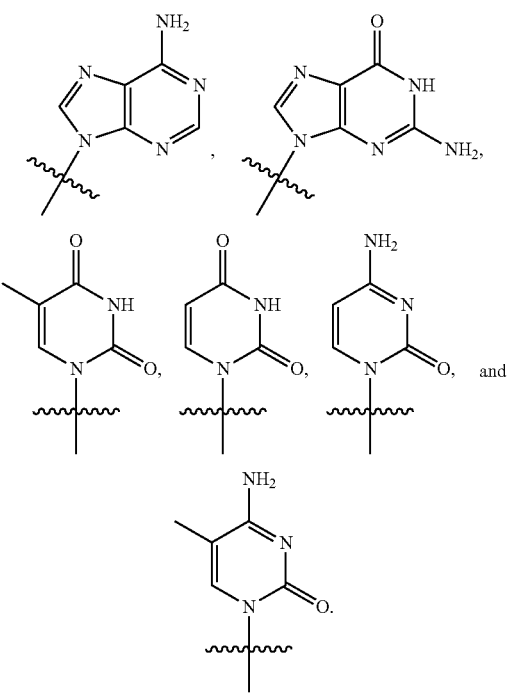

In some embodiments, BA is an optionally substituted group, which group is formed by removing a —H from

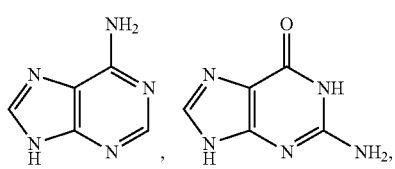

In some embodiments, BA is an optionally substituted group which group is selected from

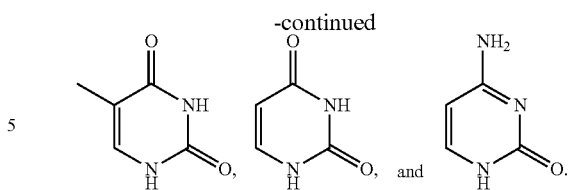

In some embodiments, BA is

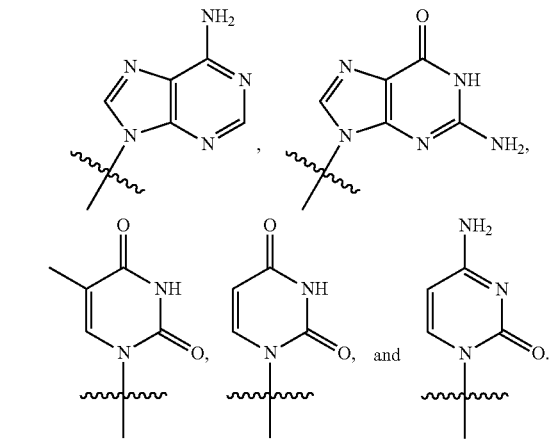

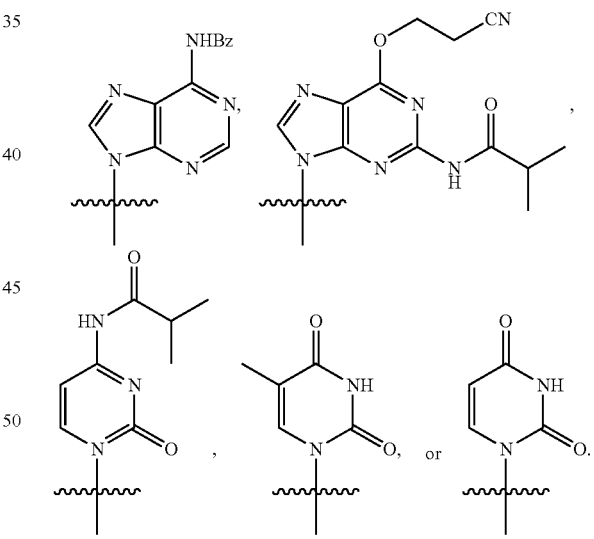

In some embodiments, BA is an optionally substituted guanine residue wherein the $O^6$-position is not protected.

Those skilled in the art appreciate that a variety of modified nucleobases are suitable in accordance with the present disclosure for formula I. Exemplary modified bases include but are not limited to those described in WO/2011/005761, US/2012/0316224, WO/2013/012758, US/2014/0194610, WO/2014/012081, US/2015/0211006, WO/2015/107425, US/2017/0037399, WO/2010/064146, US/2011/0294124, WO/2014/010250, US/2015/0197540, WO/2011/108682, US/2013/0184450, WO/2012/039448, US/2013/

0178612, WO/2012/073857, or US/2013/0253178, the modified nucleobases of each of which are hereby incorporated by reference.

In some embodiments, BA is a substituted nucleobase so that the phosphoramidite is properly protected with one or more protecting groups and can be used for oligonucleotide synthesis. Suitable protecting groups for nucleobases are widely known in the art, including those useful for oligonucleotide synthesis, and can be used in accordance with the present disclosure. In some embodiments, a protecting group is acetyl (Ac), phenylacetyl, benzoyl (Bz), isobutyryl (iBu), phenoxyacetyl (Pac), isopropyl-Pac, tertbutyl-Pac, alkyl-Pac, dimethylformamidine (DMF), or dialkylformamidine. In some embodiments, a protecting group is phthalimido, 9-fludrenylmethoxycarbonyl (FMOC), triphenylmethylsulfenyl, t-BOC, 4,4'-dimethoxytrityl (DMTr), 4-methoxytrityl (MMTr), 9-phenylxanthin-9-yl (Pixyl), trityl (Tr), or 9-(p-methoxyphenyl)xanthin-9-yl (MOX). For additional suitable protecting groups, see Green and Wuts, Protective Groups in Organic Synthesis, 2nd Ed., John Wiley & Sons, New York, 1991, and WO/2011/005761, WO/2013/012758, WO/2014/012081, WO/2015/107425, WO/2010/064146, WO/2014/010250, WO/2011/108682, WO/2012/039448, and WO/2012/073857, the protecting groups of each of which are hereby incorporated by reference.

In some embodiments, SU is a sugar moiety as used in oligonucleotides. In some embodiments, SU is a modified sugar moiety as used in oligonucleotides. In some embodiments, SU is a sugar moiety of a natural nucleoside. In some embodiments, SU is an optionally substituted sugar moiety found in a natural nucleoside. In some embodiments, SU is a modified sugar moiety found in a natural nucleoside, wherein the 2'-position is modified. In some embodiments, SU is a modified sugar moiety found in a natural nucleoside, wherein the 2'-position is modified by replacing a 2'-H and/or 2'-OH with $R^{2s}$. In some embodiments, $R^{2s}$ is not —H. In some embodiments, $R^{2s}$ is not —OH. In some embodiments, $R^{2s}$ is not —H and is not —OH.

In some embodiments, SU is -L-O—. In some embodiments, L is -Cy-. In some embodiments, L is optionally substituted 3-30 membered carbocyclylene. In some embodiments, L is optionally substituted 6-30 membered arylene. In some embodiments, L is optionally substituted 5-30 membered heteroarylene having 1-10 heteroatoms independently selected from oxygen, nitrogen and sulfur. In some embodiments, L is optionally substituted 5-30 membered heteroarylene having 1-5 heteroatoms independently selected from oxygen, nitrogen and sulfur. In some embodiments, L is optionally substituted 3-30 membered heterocyclylene having 1-10 heteroatoms independently selected from oxygen, nitrogen, sulfur, phosphorus and silicon. In some embodiments, L is optionally substituted 3-30 membered heterocyclylene having 1-5 heteroatoms independently selected from oxygen, nitrogen, sulfur, phosphorus and silicon. In some embodiments, L is optionally substituted 5-30 membered heterocyclylene having 1-10 heteroatoms independently selected from oxygen, nitrogen, sulfur, phosphorus and silicon. In some embodiments, L is optionally substituted 5-30 membered heterocyclylene having 1-5 heteroatoms independently selected from oxygen, nitrogen, sulfur, phosphorus and silicon. In some embodiments, L is optionally substituted 5-10 membered heterocyclylene having one oxygen atom. In some embodiments, L is optionally substituted 5-membered heterocyclylene having one oxygen atom. In some embodiments, L is optionally substituted 6-membered heterocyclylene having one oxygen atom. In some embodiments, L is optionally substituted 5-10 membered bicyclic heterocyclylene having one or two oxygen atoms. In some embodiments, L is optionally substituted 7-10 membered bicyclic heterocyclylene having one or two oxygen atoms. In some embodiments, L is optionally substituted 7-10 membered bicyclic heterocyclylene having two oxygen atoms. In some embodiments, L is optionally substituted 7-membered bicyclic heterocyclylene having two oxygen atoms.

In some embodiments, SU is a sugar moiety used in oligonucleotide synthesis. A person of ordinary skill in the art understands that phosphoramidites with a variety of sugar moieties can benefit from improved yields and/or purity when provided technologies are utilized for their preparation. In some embodiments, SU is an optionally substituted saturated monocyclic, bicyclic or polycyclic saturated aliphatic ring wherein one or more methylene units are replaced with —O—. In some embodiments, SU is a ribose or deoxyribose moiety found in natural DNA or RNA molecules.

In some embodiments, SU is

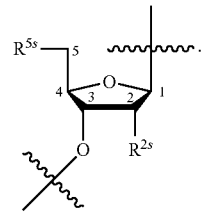

In some embodiments, SU is a modified sugar having the structure of:

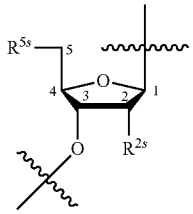

wherein $R^{5s}$ is —OR'; and $R^{2s}$ is —F, —CN, —N$_3$, —NO, —NO$_2$, —R', —OR', —SR', —N(R')$_2$, —O-L-OR', —O-L-SR', or —O-L-N(R')$_2$, or $R^{2s}$ is L connecting C2 with C1, C2, C3, C4 or C5. In some embodiments, $R^{2s}$ is —H. In some embodiments, $R^{2s}$ is —F. In some embodiments, $R^{2s}$ is —OMe. In some embodiments, $R^{2s}$ is —OCH$_2$CH$_2$OMe.

In some embodiments, a modified sugar contains one or more substituents at the 2' position (e.g., $R^{2s}$) including one of the following: —F, —CN, —N$_3$, —NO, —NO$_2$, —OR', —SR', or —N(R')$_2$, wherein each R' is independently as defined above and described herein; —O—(C$_{1-10}$ alkyl), —S—(C$_{1-10}$ alkyl), —NH—(C$_{1-10}$ alkyl), or —N(C$_{1-10}$ alkyl)$_2$; —O—(C$_{2-10}$ alkenyl), —S—(C$_{2-10}$ alkenyl), —NH—(C$_{2-10}$ alkenyl), or —N(C$_{2-10}$ alkenyl)$_2$; —O—(C$_{2-10}$ alkynyl), —S—(C$_{2-10}$ alkynyl), —NH—(C$_{2-10}$ alkynyl), or —N(C$_{2-10}$alkynyl)$_2$; or —O—(C$_{1-10}$ alkylene)-O—(C$_{1-10}$ alkyl), —O—(C$_{1-10}$ alkylene)-NH—(C$_{1-10}$ alkyl) or —O—(C$_{1-10}$ alkylene)-NH(C$_{1-10}$ alkyl)$_2$, —NH—(C$_{1-10}$ alkylene)-O—(C$_{1-10}$ alkyl), or —N(C$_{1-10}$ alkyl)-(C$_{1-10}$ alkylene)-O—(C$_{1-10}$ alkyl), wherein the alkyl, alkylene, alkenyl and alkynyl may be substituted or unsubstituted.

Examples of substituents include, and are not limited to, —O(CH$_2$)$_n$OCH$_3$, and —O(CH$_2$)$_n$NH$_2$, wherein n is from 1 to about 10, MOE, DMAOE, and DMAEOE.

Also contemplated herein are modified sugars described in WO 2001/088198; and Martin et al., *Helv. Chim. Acta,* 1995, 78, 486-504. In some embodiments, a modified sugar comprises one or more groups selected from a substituted silyl group, an RNA cleaving group, a reporter group, a fluorescent label, an intercalator, a group for improving the pharmacokinetic properties of a nucleic acid, a group for improving the pharmacodynamic properties of a nucleic acid, or other substituents having similar properties. In some embodiments, modifications are made at one or more of the the 2', 3', 4', 5', or 6' positions of the sugar or modified sugar, including the 3' position of the sugar on the 3'-terminal nucleotide or in the 5' position of the 5'-terminal nucleotide.

Modified sugars also include locked nucleic acids (LNAs). In some embodiments, two substituents on sugar carbon atoms are taken together to form a bivalent moiety. In some embodiments, two substituents are on two different sugar carbon atoms. In some embodiments, a formed bivalent moiety has the structure of -L- as defined herein. In some embodiments, R$^{2s}$ is -L-. In some embodiments, -L- is —O—CH$_2$—, wherein —CH$_2$— is optionally substituted. In some embodiments, -L- is —O—CH$_2$—. In some embodiments, -L- is —O—CH(Et)-. In some embodiments, -L- is (S)-cEt. In some embodiments, -L- is between C2 and C4 of a sugar moiety. In some embodiments, a locked nucleic acid has the structure indicated below. A locked nucleic acid of the structure below is indicated, wherein Ba represents a nucleobase or modified nucleobase as described herein, and wherein R$^{2s}$ is —OCH$_2$C4'—.

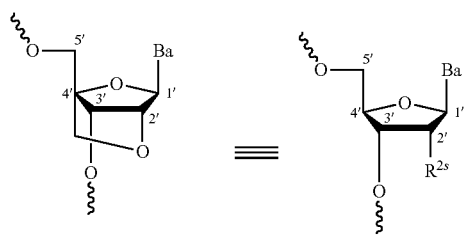

C2'OCH$_2$C4' =
LNA (Locked Nucleic Acid)           R$^{2s}$ = OCH$_2$C4'

In some embodiments, a modified sugar is an ENA such as those described in, e.g., Seth et al., J Am Chem Soc. 2010 Oct. 27; 132(42): 14942-14950. In some embodiments, a modified sugar is any of those found in an XNA (xeno-nucleic acid), for instance, arabinose, anhydrohexitol, threose, 2'fluoroarabinose, or cyclohexene.

Modified sugars include sugar mimetics such as cyclobutyl or cyclopentyl moieties in place of the pentofuranosyl sugar. Representative United States patents that teach the preparation of such modified sugar structures include, but are not limited to, U.S. Pat. Nos. 4,981,957; 5,118,800; 5,319,080; and 5,359,044. Some modified sugars that are contemplated include sugars in which the oxygen atom within the ribose ring is replaced by nitrogen, sulfur, selenium, or carbon. In some embodiments, a modified sugar is a modified ribose wherein the oxygen atom within the ribose ring is replaced with nitrogen, and wherein the nitrogen is optionally substituted with an alkyl group (e.g., methyl, ethyl, isopropyl, etc).

In some embodiments, one or more hydroxyl group in a sugar moiety is optionally and independently replaced with halogen, —R'—N(R')$_2$, —OR', or —SR', wherein each R' is independently as defined above and described herein.

In some embodiments, SU is

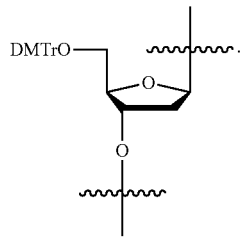

In some embodiments, SU is

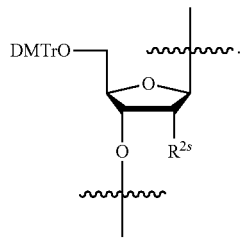

In some embodiments, SU is

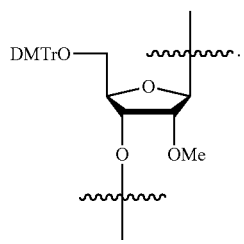

In some embodiments, L is a covalent bond. In some embodiments, L is not a covalent bond. In some embodiments, L is a bivalent, optionally substituted, linear or branched group selected from C$_{1-30}$ aliphatic and C$_{1-30}$ heteroaliphatic group having 1-10 heteroatoms independently selected from oxygen, nitrogen, sulfur, phosphorus and silicon, wherein one or more methylene units are optionally and independently replaced by an optionally substituted C$_{1-6}$ alkylene, C$_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, L is a bivalent, optionally substituted, linear or branched C$_{1-30}$ aliphatic group, wherein one or more methylene units are optionally and independently replaced by an optionally substituted C$_{1-6}$ alkylene, C$_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N (R')—, —N(R')C(O)—, —N(R')C(O)O—, —OC(O)N (R')—, —S(O)—, —S(O)$_2$—, —S(O)$_2$N(R')—, —N(R')S (O)$_2$—, —SC(O)—, —C(O)S—, —OC(O)—, or —C(O) O—. In some embodiments, L is a bivalent, optionally substituted, linear or branched $C_{1-30}$ heteroaliphatic group, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—. In some embodiments, L is a bivalent, optionally substituted, linear or branched $C_{1-30}$ heteroaliphatic group. In some embodiments, L comprises one or more Si.

In some embodiments, $R^{5s}$ is R'. In some embodiments, $R^{5s}$ is —OR'. In some embodiments, $R^5$ is a protected hydroxyl group suitable for oligonucleotide synthesis. In some embodiments, $R^{5s}$ is DMTrO—. Exemplary protecting groups are widely known in the art for use in accordance with the present disclosure. For additional examples, see Greene, T. W.; Wuts, P. G. M. Protective Groups in Organic Synthesis, 2nd ed.; Wiley: New York, 1991, and WO/2011/005761, US/2012/0316224, WO/2013/012758, US/2014/0194610, WO/2014/012081, US/2015/0211006, WO/2015/107425, US/2017/0037399, WO/2010/064146, US/2011/0294124, WO/2014/010250, US/2015/0197540, WO/2011/108682, US/2013/0184450, WO/2012/039448, US/2013/0178612, WO/2012/073857, or US/2013/0253178, the protecting groups of each of which are hereby incorporated by reference.

In some embodiments, $R^{2s}$ is —F. In some embodiments, $R^{2s}$ is —CN. In some embodiments, $R^{2s}$ is —N$_3$. In some embodiments, $R^{2s}$ is —NO. In some embodiments, $R^{2s}$ is —NO$_2$. In some embodiments, $R^{2s}$ is —R'. In some embodiments, $R^{2s}$ is —OR'. In some embodiments, $R^{2s}$ is —OR', wherein R' is optionally substituted $C_{1-6}$ aliphatic. In some embodiments, $R^{2s}$ is —OMe. In some embodiments, $R^{2s}$ is —SR'. In some embodiments, $R^{2s}$ is —N(R')$_2$. In some embodiments, $R^{2s}$ is —O-L-OR'. In some embodiments, $R^{2s}$ is —O-(optionally substituted $C_{1-6}$ alkylene)-OR'. In some embodiments, $R^{2s}$ is —O-(optionally substituted $C_{1-6}$ alkylene)-OR', wherein R' is optionally substituted $C_{1-6}$ alkyl. In some embodiments, $R^{2s}$ is —OCH$_2$CH$_2$OMe. In some embodiments, $R^{2s}$ is —O-L-SR'. In some embodiments, $R^{2s}$ is —O-L-N(R')$_2$. In some embodiments, $R^{2s}$ is L connecting C2 with C1, C2, C3, C4 or C5. In some embodiments, $R^{2s}$ L connecting C2 with C1. In some embodiments, $R^{2s}$ is L connecting C2 with C2. In some embodiments, $R^{2s}$ is L connecting C2 with C3. In some embodiments, $R^{2s}$ is L connecting C2 with C4. In some embodiments, $R^{2s}$ is L connecting C2 with C5. In some embodiments, $R^{2s}$ (C2)—O-(optionally substituted methylene)-(C4). In some embodiments, $R^{2s}$(C2)—O-(methylene)-(C4). In some embodiments, $R^{2s}$ (C2)—O-(ethylmethylene)-(C4). In some embodiments, $R^{2s}$ (C2)—O—((R)-ethylmethylene)-(C4). In some embodiments, $R^{2s}$(C2)—O—((S)-ethylmethylene)-(C4). In some embodiments, $R^{2s}$ is not —H. In some embodiments, $R^{2s}$ is not —OH. In some embodiments, $R^{2s}$ is not —OMe. In some embodiments, $R^{2s}$ is not —OCH$_2$CH$_2$OMe. In some embodiments, $R^{2s}$ is not a group selected from —OH, —OMe, and OCH$_2$CH$_2$OMe.

In some embodiments, C1 is connected to BA.

In some embodiments, -Cy- is an optionally substituted bivalent 3-30 membered carbocyclylene. In some embodiments, -Cy- is an optionally substituted bivalent 6-30 membered arylene. In some embodiments, -Cy- is an optionally substituted bivalent 5-30 membered heteroarylene having 1-10 heteroatoms independently selected from oxygen, nitrogen and sulfur. In some embodiments, -Cy- is an optionally substituted bivalent 3-30 membered heterocyclylene having 1-10 heteroatoms independently selected from oxygen, nitrogen, sulfur, phosphorus and silicon. In some embodiments, -Cy- is an optionally substituted bivalent 5-30 membered heteroarylene having 1-5 heteroatoms independently selected from oxygen, nitrogen and sulfur. In some embodiments, -Cy- is an optionally substituted bivalent 3-30 membered heterocyclylene having 1-5 heteroatoms independently selected from oxygen, nitrogen, sulfur, phosphorus and silicon.

In some embodiments, $R^1$ is R'. In some embodiments, $R^2$ is R'. In some embodiments, $R^3$ is R'.

In some embodiments, each of $R^1$, $R^2$, and $R^3$ is independently R', or two or three of $R^1$, $R^2$, and $R^3$ are taken together with their intervening atoms to form

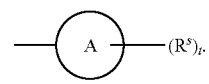

In some embodiments, valence of Ring A is t+1.

In some embodiments, $R^1$ is R. In some embodiments, $R^1$ is R, wherein R is not hydrogen. In some embodiments, $R^1$ is optionally substituted $C_{1-10}$ aliphatic. In some embodiments, $R^1$ is optionally substituted $C_{1-10}$ alkyl. In some embodiments, $R^1$ is optionally substituted methyl. In some embodiments, $R^1$ is optionally substituted ethyl. In some embodiments, $R^1$ is —O(CH$_2$)$_2$CN.

In some embodiments, $R^2$ is R. In some embodiments, $R^2$ is R, wherein R is not hydrogen. In some embodiments, $R^2$ is optionally substituted $C_{1-10}$ aliphatic. In some embodiments, $R^2$ is optionally substituted $C_{1-10}$ alkyl. In some embodiments, $R^2$ is optionally substituted methyl. In some embodiments, $R^2$ is optionally substituted ethyl. In some embodiments, $R^2$ is isopropyl.

In some embodiments, $R^3$ is R. In some embodiments, $R^3$ is R, wherein R is not hydrogen. In some embodiments, $R^3$ is optionally substituted $C_{1-10}$ aliphatic. In some embodiments, $R^3$ is optionally substituted $C_{1-10}$ alkyl. In some embodiments, $R^3$ is optionally substituted methyl. In some embodiments, $R^3$ is optionally substituted ethyl. In some embodiments, $R^3$ is isopropyl.

In some embodiments, $R^2$ and $R^3$ are the same. In some embodiments, $R^2$ and $R^3$ are different.

In some embodiments, $R^1$ and $R^2$ are taken together with their intervening atoms to form

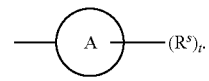

In some embodiments, $R^1$ and $R^2$ are taken together with their intervening atoms to form

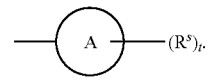

In some embodiments, R¹ and R³ are taken together with their intervening atoms to form

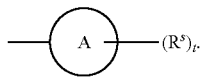

In some embodiments, R² and R³ are taken together with their intervening atoms to form

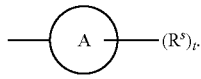

In some embodiments, R¹, R² and R³ are taken together with their intervening atoms to form

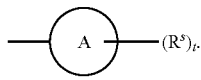

In some embodiments, Ring A is an optionally substituted multivalent, monocyclic, bicyclic or polycyclic, saturated, partially unsaturated, or aryl 3-30 membered ring having, in addition to the intervening nitrogen, phosphorus and oxygen atoms, 0-10 heteroatoms independently selected from oxygen, nitrogen, sulfur, phosphorus and silicon. In some embodiments, Ring A is an optionally substituted multivalent, monocyclic, bicyclic or polycyclic, saturated, partially unsaturated, or aryl 3-30 membered ring having, in addition to the intervening nitrogen, phosphorus and oxygen atoms, 0-10 heteroatoms independently selected from oxygen, nitrogen, and sulfur.

In some embodiments, Ring A is an optionally substituted multivalent, monocyclic, bicyclic or polycyclic, saturated, partially unsaturated, or aryl 3-30 membered ring having, in addition to the intervening nitrogen, phosphorus and oxygen atoms, 0 heteroatom.

In some embodiments, Ring A is an optionally substituted multivalent monocyclic saturated 5-7 membered ring having the intervening nitrogen, phosphorus and oxygen atoms and no additional heteroatoms. In some embodiments, Ring A is an optionally substituted multivalent monocyclic saturated 5-membered ring having the intervening nitrogen, phosphorus and oxygen atoms and no additional heteroatoms. In some embodiments, Ring A is an optionally substituted multivalent monocyclic saturated 6-membered ring having the intervening nitrogen, phosphorus and oxygen atoms and no additional heteroatoms. In some embodiments, Ring A is an optionally substituted multivalent monocyclic saturated 7-membered ring having the intervening nitrogen, phosphorus and oxygen atoms and no additional heteroatoms.

In some embodiments, Ring A is an optionally substituted multivalent, bicyclic, saturated, partially unsaturated, or aryl 5-30 membered ring having, in addition to the intervening nitrogen, phosphorus and oxygen atoms, 0-10 heteroatoms independently selected from oxygen, nitrogen, sulfur, phosphorus and silicon. In some embodiments, Ring A is an optionally substituted multivalent, bicyclic, saturated, partially unsaturated, or aryl 5-30 membered ring having, in addition to the intervening nitrogen, phosphorus and oxygen atoms, 0-10 heteroatoms independently selected from oxygen, nitrogen, and sulfur. In some embodiments, Ring A is a multivalent, bicyclic and saturated 8-10 membered bicyclic ring having the intervening nitrogen, phosphorus and oxygen atoms and no additional heteroatoms. In some embodiments, Ring A is a multivalent, bicyclic and saturated 8-membered bicyclic ring having the intervening nitrogen, phosphorus and oxygen atoms and no additional heteroatoms. In some embodiments, Ring A is a multivalent, bicyclic and saturated 9-membered bicyclic ring having the intervening nitrogen, phosphorus and oxygen atoms and no additional heteroatoms. In some embodiments, Ring A is a multivalent, bicyclic and saturated 10-membered bicyclic ring having the intervening nitrogen, phosphorus and oxygen atoms and no additional heteroatoms. In some embodiments, Ring A is bicyclic and comprises a 5-membered ring fused to a 5-membered ring. In some embodiments, Ring A is bicyclic and comprises a 5-membered ring fused to a 6-membered ring. In some embodiments, the 5-membered ring comprises the intervening nitrogen, phosphorus and oxygen atoms as ring atoms. In some embodiments, Ring A comprises a ring system having the backbone structure of

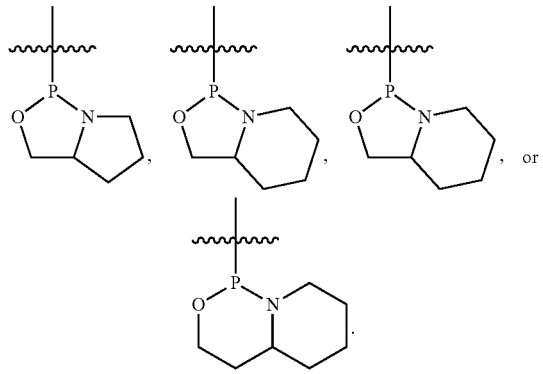

In some embodiments, Ring A is optionally substituted

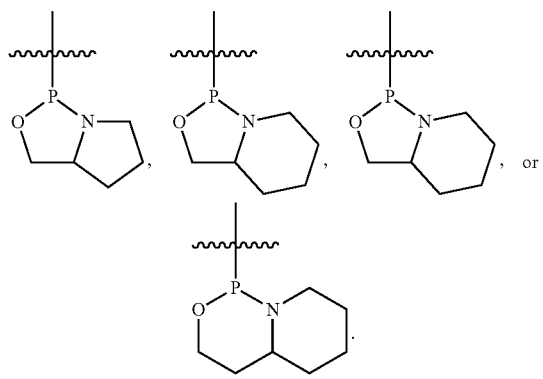

In some embodiments, Ring A is

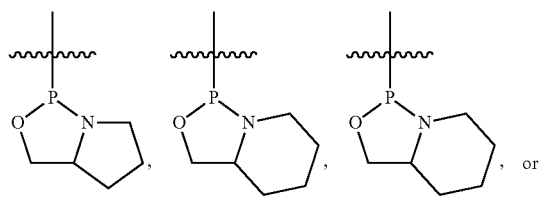

-continued

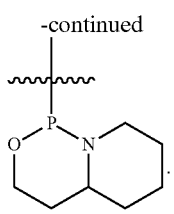

each of which is independently substituted with 1-5 $R^s$. In some embodiments, Ring A is

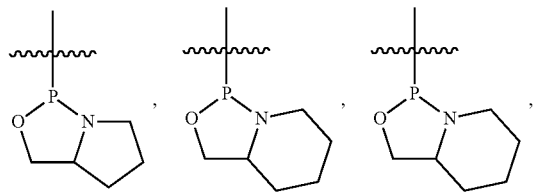

or

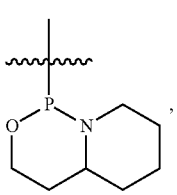

each of which is independently substituted with 1-5 $R^s$, wherein the carbon atom connected to the oxygen atom is substituted with 1 or 2 $R^s$. In some embodiments, Ring A, such as a substituted group selected from

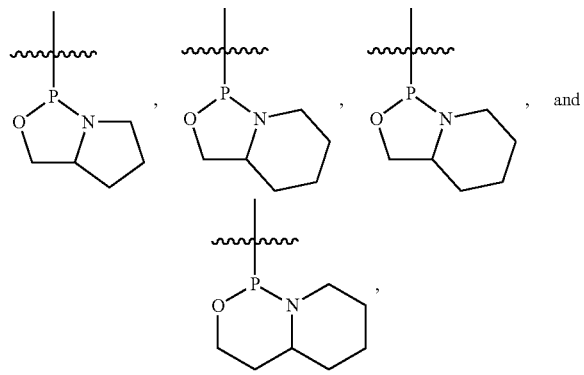

comprises one or more chiral centers other than the phosphorus atom and the tertiary carbon atom connected to nitrogen. In some embodiments, the carbon atom connected to the oxygen atom is a chiral center, for example, as a result of substitution at that carbon atom with one or two $R^s$. In some embodiments, $R^s$ is phenyl. In some embodiments, $R^s$ is alkyl. In some embodiments, $R^s$ is methyl. In some embodiments, one $R^s$ is phenyl and one $R^s$ is methyl. In some embodiments, Ring A is selected from those described in WO/2011/005761, US/2012/0316224, WO/2013/012758, US/2014/0194610, WO/2014/012081, US/2015/0211006, WO/2015/107425, US/2017/0037399, WO/2010/064146, US/2011/0294124, WO/2014/010250, US/2015/0197540, WO/2011/108682, US/2013/0184450, WO/2012/039448, US/2013/0178612, WO/2012/073857, or US/2013/0253178, incorporated herein by reference. In some embodiments, a compound, e.g., phosphoramidite is chiral and is stereochemically pure. In some embodiments, a provided compound, e.g., phosphoramidite has a purity of no less than 80%, 85%, 90%, 91%, 92%, 93%, 94%, 95%, 96%, 97%, 98%, 99%, or 99.5%.

In some embodiments, Ring A is an optionally substituted multivalent, polycyclic, saturated, partially unsaturated, or aryl 3-30 membered ring having, in addition to the intervening nitrogen, phosphorus and oxygen atoms, 0-10 heteroatoms independently selected from oxygen, nitrogen, sulfur, phosphorus and silicon. In some embodiments, Ring A is an optionally substituted multivalent, polycyclic, saturated, partially unsaturated, or aryl 3-30 membered ring having, in addition to the intervening nitrogen, phosphorus and oxygen atoms, 0-10 heteroatoms independently selected from oxygen, nitrogen, and sulfur.

In some embodiments, Ring A is monocyclic, bicyclic or polycyclic and comprises an optionally substituted 5-10 membered monocyclic ring whose ring atoms comprise the intervening nitrogen, phosphorus and oxygen atoms. In some embodiments, Ring A is monocyclic, bicyclic or polycyclic and comprises an optionally substituted 5-9 membered monocyclic ring whose ring atoms comprise the intervening nitrogen, phosphorus and oxygen atoms. In some embodiments, Ring A is monocyclic, bicyclic or polycyclic and comprises an optionally substituted 5-8 membered monocyclic ring whose ring atoms comprise the intervening nitrogen, phosphorus and oxygen atoms. In some embodiments, Ring A is monocyclic, bicyclic or polycyclic and comprises an optionally substituted 5-7 membered monocyclic ring whose ring atoms comprise the intervening nitrogen, phosphorus and oxygen atoms. In some embodiments, Ring A is monocyclic, bicyclic or polycyclic and comprises an optionally substituted 5-6 membered monocyclic ring whose ring atoms comprise the intervening nitrogen, phosphorus and oxygen atoms.

In some embodiments, Ring A is monocyclic, bicyclic or polycyclic and comprises an optionally substituted 5-membered monocyclic ring whose ring atoms comprise the intervening nitrogen, phosphorus and oxygen atoms. In some embodiments, Ring A is monocyclic, bicyclic or polycyclic and comprises an optionally substituted 6-membered monocyclic ring whose ring atoms comprise the intervening nitrogen, phosphorus and oxygen atoms. In some embodiments, Ring A is monocyclic, bicyclic or polycyclic and comprises an optionally substituted 7-membered monocyclic ring whose ring atoms comprise the intervening nitrogen, phosphorus and oxygen atoms. In some embodiments, Ring A is monocyclic, bicyclic or polycyclic and comprises an optionally substituted 8-membered monocyclic ring whose ring atoms comprise the intervening nitrogen, phosphorus and oxygen atoms. In some embodiments, Ring A is monocyclic, bicyclic or polycyclic and comprises an optionally substituted 9-membered monocyclic ring whose ring atoms comprise the intervening nitrogen, phosphorus and oxygen atoms. In some embodiments, Ring A is monocyclic, bicyclic or polycyclic and comprises an optionally substituted 10-membered monocyclic ring whose ring atoms comprise the intervening nitrogen, phosphorus and oxygen atoms.

In some embodiments, Ring A is monocyclic, bicyclic or polycyclic and comprises an optionally substituted 5-membered ring whose ring atoms consist of the intervening nitrogen, phosphorus and oxygen atoms and carbon atoms. In some embodiments, Ring A is monocyclic, bicyclic or polycyclic and comprises an optionally substituted 6-membered ring whose ring atoms consist of the intervening nitrogen, phosphorus and oxygen atoms and carbon atoms. In some embodiments, Ring A is monocyclic, bicyclic or polycyclic and comprises an optionally substituted 7-membered ring whose ring atoms consist of the intervening nitrogen, phosphorus and oxygen atoms and carbon atoms. In some embodiments, Ring A is monocyclic, bicyclic or polycyclic and comprises an optionally substituted 8-membered ring whose ring atoms consist of the intervening nitrogen, phosphorus and oxygen atoms and carbon atoms. In some embodiments, Ring A is monocyclic, bicyclic or polycyclic and comprises an optionally substituted 9-membered ring whose ring atoms consist of the intervening nitrogen, phosphorus and oxygen atoms and carbon atoms. In some embodiments, Ring A is monocyclic, bicyclic or polycyclic and comprises an optionally substituted 10-membered ring whose ring atoms consist of the intervening nitrogen, phosphorus and oxygen atoms and carbon atoms.

In some embodiments, Ring A comprises a ring system having the backbone structure

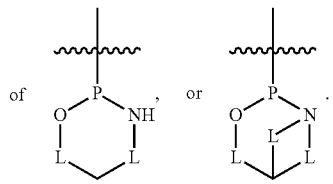

In some embodiments, $R^s$ is R'. In some embodiments, $R^s$ is R. In some embodiments, $R^s$ is optionally substituted $C_{1-30}$ heteroaliphatic. In some embodiments, $R^s$ comprises one or more silicon atoms. In some embodiments, $R^s$ is —CH$_2$Si(Ph)$_2$CH$_3$.

In some embodiments, $R^s$ is -L-R'. In some embodiments, $R^s$ is -L-R' wherein -L- is a bivalent, optionally substituted $C_{1-30}$ heteroaliphatic group. In some embodiments, $R^s$ is —CH$_2$Si(Ph)$_2$CH$_3$.

In some embodiments, t is 0. In some embodiments, t is 1-5. In some embodiments, t is 1. In some embodiments, t is 2. In some embodiments, t is 3. In some embodiments, t is 4. In some embodiments, t is 5.

In some embodiments, R' is —R. In some embodiments, R' is —C(O)R. In some embodiments, R' is —CO$_2$R. In some embodiments, R' is —SO$_2$R. In some embodiments, two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon. In some embodiments, R' is hydrogen. In some embodiments, R' is not hydrogen.

In some embodiments, R is hydrogen. In some embodiments, R is not hydrogen. In some embodiments, R is an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

In some embodiments, R is hydrogen or an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, and sulfur, a 4-7 membered saturated or partially unsaturated heterocyclic ring having 1-3 heteroatoms independently selected from nitrogen, oxygen, and sulfur, a 7-10 membered bicyclic saturated or partially unsaturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur.

In some embodiments, R is optionally substituted $C_{1-30}$ aliphatic. In some embodiments, R is optionally substituted $C_{1-20}$ aliphatic. In some embodiments, R is optionally substituted $C_{1-15}$ aliphatic. In some embodiments, R is optionally substituted $C_{1-10}$ aliphatic. In some embodiments, R is optionally substituted $C_{1-6}$ aliphatic. In some embodiments, R is optionally substituted $C_{1-6}$ alkyl. In some embodiments, R is optionally substituted hexyl, pentyl, butyl, propyl, ethyl or methyl. In some embodiments, R is optionally substituted hexyl. In some embodiments, R is optionally substituted pentyl. In some embodiments, R is optionally substituted butyl. In some embodiments, R is optionally substituted propyl. In some embodiments, R is optionally substituted ethyl. In some embodiments, R is optionally substituted methyl. In some embodiments, R is hexyl. In some embodiments, R is pentyl. In some embodiments, R is butyl. In some embodiments, R is propyl. In some embodiments, R is ethyl. In some embodiments, R is methyl. In some embodiments, R is isopropyl. In some embodiments, R is n-propyl. In some embodiments, R is tert-butyl. In some embodiments, R is sec-butyl. In some embodiments, R is n-butyl.

In some embodiments, R is optionally substituted $C_{3-30}$ cycloaliphatic. In some embodiments, R is optionally substituted $C_{3-20}$ cycloaliphatic. In some embodiments, R is optionally substituted $C_{3-10}$ cycloaliphatic. In some embodiments, R is optionally substituted cyclohexyl. In some embodiments, R is cyclohexyl. In some embodiments, R is optionally substituted cyclopentyl. In some embodiments, R is cyclopentyl.

In some embodiments, R is an optionally substituted 3-30 membered saturated or partially unsaturated carbocyclic ring. In some embodiments, R is an optionally substituted 3-7 membered saturated or partially unsaturated carbocyclic ring. In some embodiments, R is an optionally substituted 3-membered saturated or partially unsaturated carbocyclic ring. In some embodiments, R is an optionally substituted 4-membered saturated or partially unsaturated carbocyclic ring. In some embodiments, R is an optionally substituted 5-membered saturated or partially unsaturated carbocyclic ring. In some embodiments, R is an optionally substituted 6-membered saturated or partially unsaturated carbocyclic ring. In some embodiments, R is an optionally substituted 7-membered saturated or partially unsaturated carbocyclic ring. In some embodiments, R is optionally substituted cycloheptyl. In some embodiments, R is cycloheptyl. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, R is $C_{1-30}$ heteroaliphatic having 1-10 heteroatoms independently selected from oxygen, nitrogen, sulfur, phosphorus and silicon. In some embodiments, R is $C_{1-20}$ heteroaliphatic having 1-10 heteroatoms. In some embodiments, R is $C_{1-20}$ heteroaliphatic having 1-10 heteroatoms independently selected from oxygen, nitrogen, sulfur, phosphorus or silicon, optionally including one or more oxidized forms of nitrogen, sulfur, phosphorus or selenium. In some embodiments, R is $C_{1-30}$ heteroaliphatic comprising 1-10 groups independently selected from

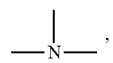

—N—, —N=, =N, —S—, —S(O)—, —S(O)$_2$—, —O—, =O,

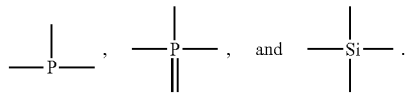

In some embodiments, R is optionally substituted $C_{6-30}$ aryl. In some embodiments, R is optionally substituted phenyl. In some embodiments, R is phenyl. In some embodiments, R is substituted phenyl.

In some embodiments, R is an optionally substituted 8-10 membered bicyclic saturated, partially unsaturated or aryl ring. In some embodiments, R is an optionally substituted 8-10 membered bicyclic saturated ring. In some embodiments, R is an optionally substituted 8-10 membered bicyclic partially unsaturated ring. In some embodiments, R is an optionally substituted 8-10 membered bicyclic aryl ring. In some embodiments, R is optionally substituted naphthyl.

In some embodiments, R is optionally substituted 5-30 membered heteroaryl ring having 1-10 heteroatoms independently selected from oxygen, nitrogen, sulfur, phosphorus and silicon. In some embodiments, R is optionally substituted 5-30 membered heteroaryl ring having 1-10 heteroatoms independently selected from oxygen, nitrogen, and sulfur. In some embodiments, R is optionally substituted 5-30 membered heteroaryl ring having 1-5 heteroatoms independently selected from oxygen, nitrogen, sulfur, phosphorus and silicon. In some embodiments, R is optionally substituted 5-30 membered heteroaryl ring having 1-5 heteroatoms independently selected from oxygen, nitrogen, and sulfur.

In some embodiments, R is an optionally substituted 5-6 membered monocyclic heteroaryl ring having 1-4 heteroatoms independently selected from nitrogen, oxygen, and sulfur. In some embodiments, R is a substituted 5-6 membered monocyclic heteroaryl ring having 1-4 heteroatoms independently selected from nitrogen, oxygen, and sulfur. In some embodiments, R is an unsubstituted 5-6 membered monocyclic heteroaryl ring having 1-4 heteroatoms independently selected from nitrogen, oxygen, and sulfur.

In some embodiments, R is an optionally substituted 5-membered monocyclic heteroaryl ring having 1-4 heteroatoms independently selected from nitrogen, oxygen or sulfur. In some embodiments, R is an optionally substituted 6-membered monocyclic heteroaryl ring having 1-4 heteroatoms independently selected from nitrogen, oxygen, and sulfur.

In some embodiments, R is an optionally substituted 5-membered monocyclic heteroaryl ring having one heteroatom selected from nitrogen, oxygen, and sulfur. In some embodiments, R is selected from optionally substituted pyrrolyl, furanyl, or thienyl.

In some embodiments, R is an optionally substituted 5-membered heteroaryl ring having two heteroatoms independently selected from nitrogen, oxygen, and sulfur. In certain embodiments, R is an optionally substituted 5-membered heteroaryl ring having one nitrogen atom, and an additional heteroatom selected from sulfur or oxygen. Exemplary R groups include but are not limited to optionally substituted pyrazolyl, imidazolyl, thiazolyl, isothiazolyl, oxazolyl or isoxazolyl.

In some embodiments, R is an optionally substituted 5-membered heteroaryl ring having three heteroatoms independently selected from nitrogen, oxygen, and sulfur. Exemplary R groups include but are not limited to optionally substituted triazolyl, oxadiazolyl or thiadiazolyl.

In some embodiments, R is an optionally substituted 5-membered heteroaryl ring having four heteroatoms independently selected from nitrogen, oxygen, and sulfur. Exemplary R groups include but are not limited to optionally substituted tetrazolyl, oxatriazolyl and thiatriazolyl.

In some embodiments, R is an optionally substituted 6-membered heteroaryl ring having 1-4 nitrogen atoms. In some embodiments, R is an optionally substituted 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having four nitrogen atoms. In some embodiments, R is an optionally substituted 6-membered heteroaryl ring having three nitrogen atoms. In some embodiments, R is an optionally substituted 6-membered heteroaryl ring having two nitrogen atoms. In certain embodiments, R is an optionally substituted 6-membered heteroaryl ring having one nitrogen atom. Exemplary R groups include but are not limited to optionally substituted pyridinyl, pyrimidinyl, pyrazinyl, pyridazinyl, triazinyl, or tetrazinyl.

In some embodiments, R is 3-30 membered heterocyclic ring having 1-10 heteroatoms independently selected from oxygen, nitrogen, sulfur, phosphorus and silicon. In some embodiments, R is 3-30 membered heterocyclic ring having 1-10 heteroatoms independently selected from oxygen, nitrogen, and sulfur. In some embodiments, R is 3-30 membered heterocyclic ring having 1-5 heteroatoms independently selected from oxygen, nitrogen, sulfur, phosphorus and silicon. In some embodiments, R is 3-30 membered heterocyclic ring having 1-5 heteroatoms independently selected from oxygen, nitrogen, and sulfur.

In some embodiments, R is an optionally substituted 3-7 membered saturated or partially unsaturated heterocyclic ring having 1-3 heteroatoms independently selected from nitrogen, oxygen, and sulfur. In some embodiments, R is a substituted 3-7 membered saturated or partially unsaturated heterocyclic ring having 1-3 heteroatoms independently selected from nitrogen, oxygen, and sulfur. In some embodiments, R is an unsubstituted 3-7 membered saturated or partially unsaturated heterocyclic ring having 1-3 heteroatoms independently selected from nitrogen, oxygen, and sulfur. In certain embodiments, R is an optionally substituted 5-7 membered partially unsaturated monocyclic ring having 1-3 heteroatoms independently selected from nitrogen, oxygen, and sulfur. In certain embodiments, R is an optionally substituted 5-6 membered partially unsaturated monocyclic ring having 1-3 heteroatoms independently selected from nitrogen, oxygen, and sulfur. In certain embodiments, R is an optionally substituted 5-membered partially unsaturated monocyclic ring having 1-3 heteroatoms independently selected from nitrogen, oxygen, and sulfur. In certain embodiments, R is an optionally substituted 6-membered partially unsaturated monocyclic ring having 1-3 heteroatoms independently selected from nitrogen, oxygen, and sulfur. In certain embodiments, R is an optionally substituted 7-membered partially unsaturated monocyclic ring having 1-3 heteroatoms independently selected from nitrogen, oxygen, and sulfur. In some embodiments, R is optionally substituted 3-membered heterocyclic ring having one heteroatom selected from nitrogen, oxygen or sulfur. In some embodiments, R is optionally substituted 4-membered heterocyclic ring having 1-3 heteroatoms independently selected from nitrogen, oxygen, and sulfur. In some embodiments, R is optionally substituted 5-membered heterocyclic ring having 1-3 heteroatoms independently selected from nitrogen, oxygen, and sulfur. In some embodiments, R is optionally substituted 6-membered heterocyclic ring having 1-3 heteroatoms independently selected from nitrogen, oxygen, and sulfur. In some embodiments, R is optionally substituted 7-membered heterocyclic ring having 1-3 heteroatoms independently selected from nitrogen, oxygen, and sulfur.

In some embodiments, R is an optionally substituted 7-10 membered bicyclic saturated or partially unsaturated heterocyclic ring having 1-5 heteroatoms independently selected from nitrogen, oxygen, and sulfur. In some embodiments, R is optionally substituted indolinyl. In some embodiments, R is optionally substituted isoindolinyl. In some embodiments, R is optionally substituted 1, 2, 3, 4-tetrahydroquinolinyl. In some embodiments, R is optionally substituted 1, 2, 3, 4-tetrahydroisoquinolinyl. In some embodiments, R is an optionally substituted azabicyclo[3.2.1]octanyl.

In some embodiments, R is an optionally substituted 8-10 membered bicyclic heteroaryl ring having 1-5 heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In some embodiments, R is an optionally substituted 5,6-fused heteroaryl ring having 1-3 heteroatoms independently selected from nitrogen, oxygen, and sulfur. In some embodiments, R is an optionally substituted 5,6-fused heteroaryl ring having two heteroatoms independently selected from nitrogen, oxygen, and sulfur. In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is an optionally substituted 5,6-fused heteroaryl ring having three heteroatoms independently selected from nitrogen, oxygen, and sulfur. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, R is an optionally substituted 5,6-fused heteroaryl ring having four heteroatoms independently selected from nitrogen, oxygen, and sulfur. In some embodiments, R is an optionally substituted 5,6-fused heteroaryl ring having five heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In other embodiments, R is an optionally substituted 5,6-fused heteroaryl ring having 1-2 heteroatoms independently selected from nitrogen, oxygen, and sulfur. In certain embodiments, R is an optionally substituted 5,6-fused heteroaryl ring having one heteroatom independently selected from nitrogen, oxygen, and sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, and sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, and sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen, and sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, and sulfur.

In certain embodiments, R is an optionally substituted 6,6-fused heteroaryl ring having 1-5 heteroatoms independently selected from nitrogen, oxygen, and sulfur. In some embodiments, R is an optionally substituted 6,6-fused heteroaryl ring having 1-2 heteroatoms independently selected from nitrogen, oxygen, and sulfur. In other embodiments, R is an optionally substituted 6,6-fused heteroaryl ring having one heteroatom selected from nitrogen, oxygen, and sulfur. In some embodiments, R is optionally substituted quinolinyl. In some embodiments, R is optionally substituted isoquinolinyl. In some embodiments, R is an optionally substituted 6,6-fused heteroaryl ring having two heteroatoms independently selected from nitrogen, oxygen, and sulfur. In some embodiments, R is optionally substituted quinazolinyl, phthalazinyl, quinoxalinyl or naphthyridinyl. In some embodiments, R is an optionally substituted 6,6-fused heteroaryl ring having three heteroatoms independently selected from nitrogen, oxygen, and sulfur. In some embodiments, R is optionally substituted pyridopyrimidinyl, pyridopyridazinyl, pyridopyrazinyl, or benzotriazinyl. In some embodiments, R is an optionally substituted 6,6-fused heteroaryl ring having four heteroatoms independently selected from nitrogen, oxygen, and sulfur. In some embodiments, R is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, R is an optionally substituted 6,6- fused heteroaryl ring having five heteroatoms independently selected from nitrogen, oxygen, and sulfur.

In some embodiments, $R^1$, $R^2$, $R^3$ or

comprises one or more chiral elements, for example, chiral centers. In some embodiments, $R^1$, $R^2$, $R^3$ or

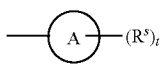

is asymmetric. Phosphoramidites comprising such asymmetric moieties can, among other things, be used for preparing chirally controlled oligonucleotide compositions, such as those described in WO/2014/012081, WO/2015/107425, etc. In some embodiments, when used in oligonucleotide synthesis, such phosphoramidites can deliver diastereoselectivity greater than about 50%, 60%, 70%, 80%, 90%, 91%, 92%, 93%, 94%, 95%, 96%, 97%, 98% or 99% at the newly formed P-chiral center, optionally with greater than about 50%, 60%, 70%, 80%, 90%, 91%, 92%, 93%, 94%, 95%, 96%, 97%, 98% or 99% yield.

In some embodiments,

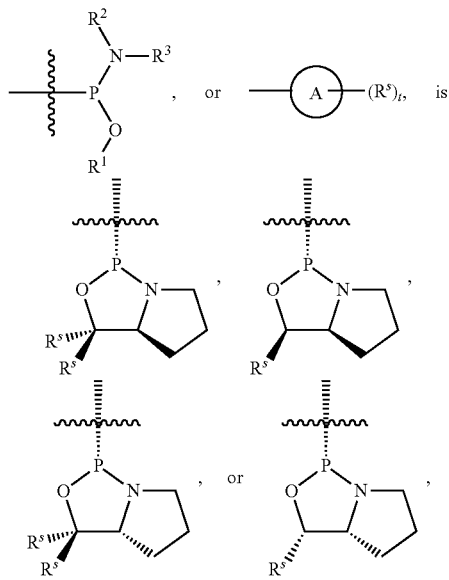

wherein one or more $R^s$ is not hydrogen. In some embodiments,

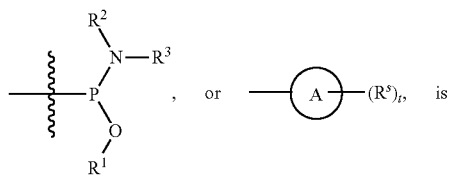

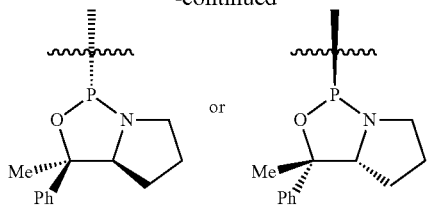

In some embodiments,

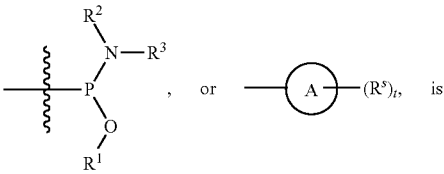

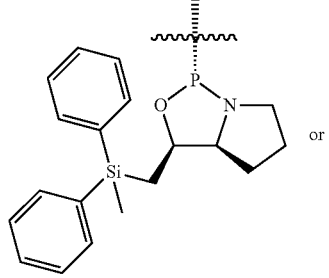

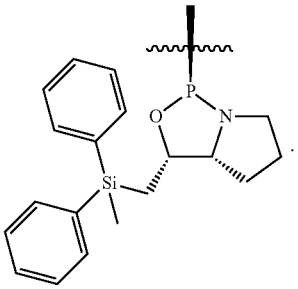

In some embodiments,

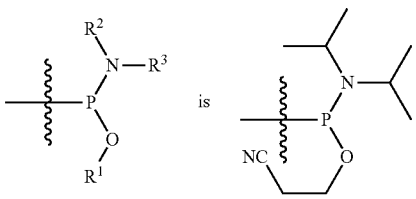

As a person of ordinary skill in the art appreciates, phosphoramidites can be prepared from nucleoside and chiral auxiliaries, including those comprising an amino group and a hydroxyl group as illustrated in the examples. Suitable chiral auxiliaries include but are not limited to those described in WO/2011/005761, US/2012/0316224, WO/2013/012758, US/2014/0194610, WO/2014/012081, US/2015/0211006, WO/2015/107425, US/2017/0037399, WO/2010/064146, US/2011/0294124, WO/2014/010250, US/2015/0197540, WO/2011/108682, US/2013/0184450, WO/2012/039448, US/2013/0178612, WO/2012/073857, or US/2013/0253178, the chiral auxiliaries of each of which are hereby incorporated by reference.

In some embodiments, a phosphoramidite is one described in WO/2011/005761, US/2012/0316224, WO/2013/012758, US/2014/0194610, WO/2014/012081, US/2015/0211006, WO/2015/107425, US/2017/0037399, WO/2010/064146, US/2011/0294124, WO/2014/010250, US/2015/0197540, WO/2011/108682, US/2013/0184450, WO/2012/039448, US/2013/0178612, WO/2012/073857, or US/2013/0253178, the phosphoramidites of each of which are hereby incorporated by reference. In some embodiments, the present disclosure provides a method comprising an oligonucleotide preparation method described in one of these applications, wherein the phosphoramidites are purified using a method described herein.

In some embodiments, a phosphoramidite is:

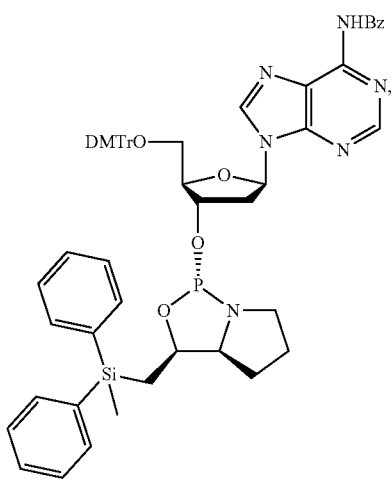

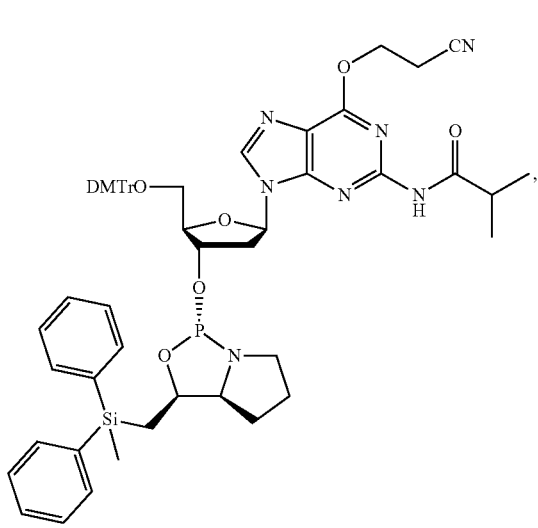

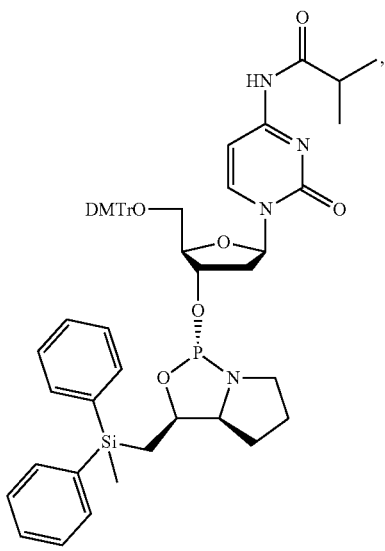

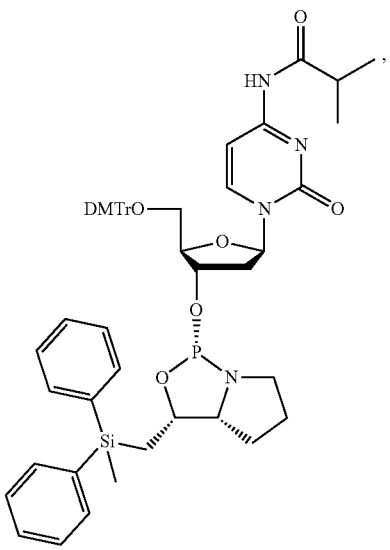

-continued
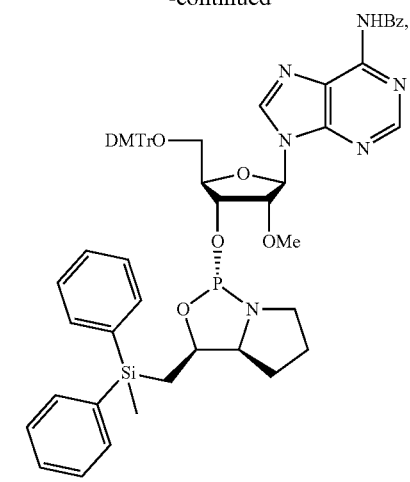
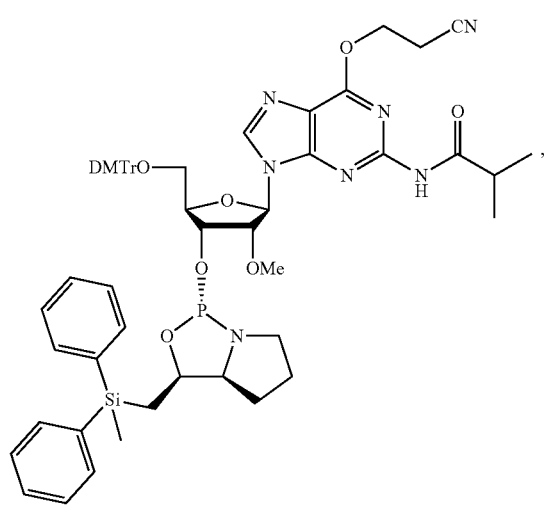
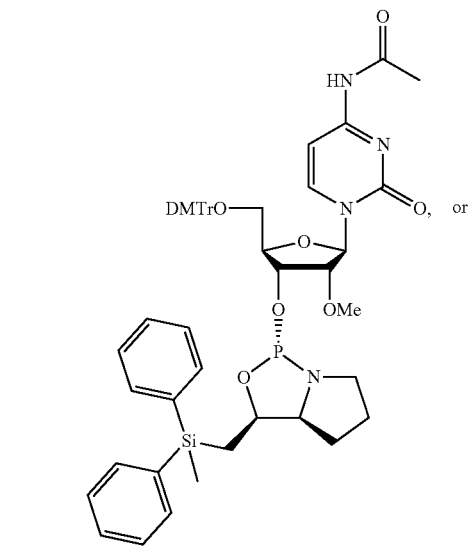
-continued
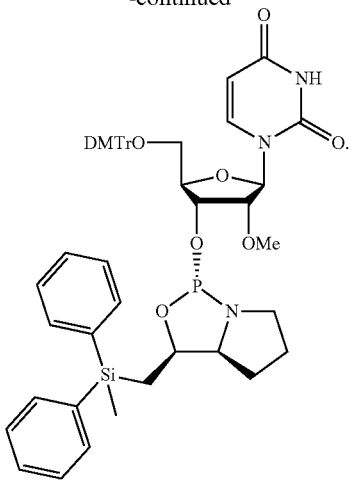
In some embodiments, a phosphoramidite is selected from Table 1 below:
TABLE 1
Example phosphoramidites.
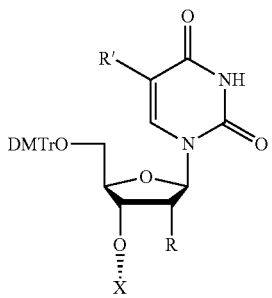
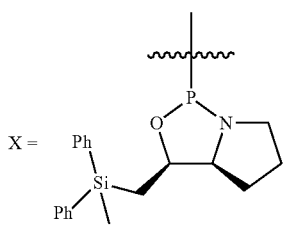 [SMILES: *P1O[C@H](C[Si](C)(c2ccccc2)c2ccccc2)[C@@H]2CCCN21]
R' = H, R = H
R' = H, R = OMe
R' = H, R = OCH₂CH₂OMe
R' = H, R = F
R' = Me, R = H
R' = Me, R = OMe
R' = Me, R = OCH₂CH₂OMe
R' = Me, R = F
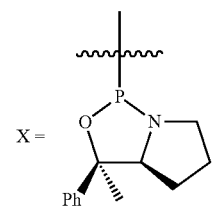 [SMILES: *P1O[C@](C)(c2ccccc2)[C@@H]2CCCN21]
R' = H, R = H
R' = H, R = OMe
R' = H, R = OCH₂CH₂OMe TABLE 1-continued Example phosphoramidites.

R' = H, R = F
R' = Me, R = H
R' = Me, R = OMe
R' = Me, R = OCH$_2$CH$_2$OMe
R' = Me, R = F

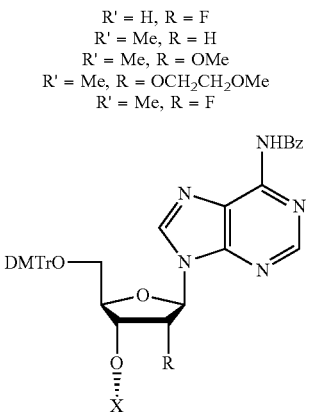

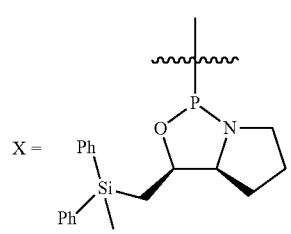 [SMILES: *P1O[C@H](C[Si](C)(c2ccccc2)c2ccccc2)[C@@H]2CCCN21]

R = H
R = OMe
R = OCH$_2$CH$_2$OMe
R = F

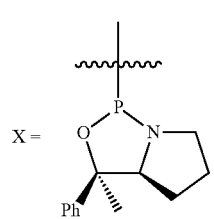 [SMILES: *P1O[C@](C)(c2ccccc2)[C@@H]2CCCN21]

R = H
R = OMe
R = OCH$_2$CH$_2$OMe
R = F

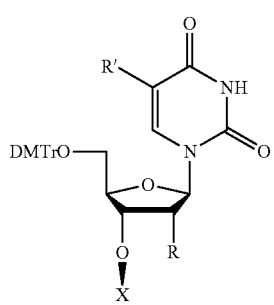

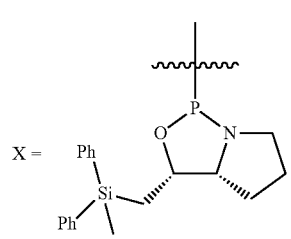 [SMILES: *P1O[C@@H](C[Si](C)(c2ccccc2)c2ccccc2)[C@H]2CCCN21]

TABLE 1-continued

Example phosphoramidites.

R' = H, R = H
R' = H, R = OMe
R' = H, R = OCH$_2$CH$_2$OMe
R' = H, R = F
R' = Me, R = H
R' = Me, R = OMe
R' = Me, R = OCH$_2$CH$_2$OMe
R' = Me, R = F

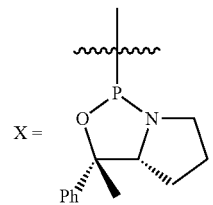 [SMILES: *P1O[C@@](C)(c2ccccc2)[C@H]2CCCN21]

R' = H, R = H
R' = H, R = OMe
R' = H, R = OCH$_2$CH$_2$OMe
R' = H, R = F
R' = Me, R = H
R' = Me, R = OMe
R' = Me, R = OCH$_2$CH$_2$OMe
R' = Me, R = F

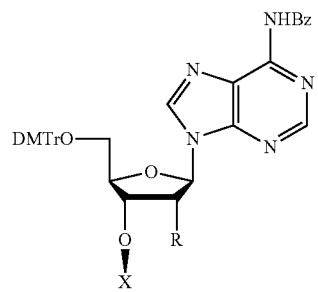

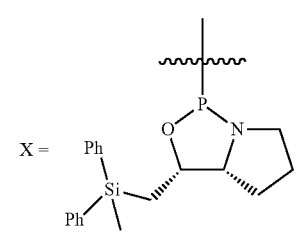 [SMILES: *P1O[C@@H](C[Si](C)(c2ccccc2)c2ccccc2)[C@H]2CCCN21]

R = H
R = OMe
R = OCH$_2$CH$_2$OMe
R = F

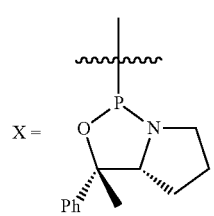 [SMILES: *P1O[C@@](C)(c2ccccc2)[C@H]2CCCN21]

R = H
R = OMe
R = OCH$_2$CH$_2$OMe
R = F

TABLE 1-continued

Example phosphoramidites.

[Structure: DMTrO-deoxyribose-cytosine with NHR', 2'-OR, 3'-O-X]

[Structure: X = phosphoramidite with Ph2(Me)Si-CH2- pyrrolidine-oxazaphospholidine]

R' = Ac, R = H
R' = Ac, R = OMe
R' = Ac, R = OCH₂CH₂OMe
R' = Ac, R = F
R' = iBu, R = H
R' = iBu, R = OMe
R' = iBu, R = OCH₂CH₂OMe
R' = iBu, R = F

[Structure: X = phosphoramidite with Ph(Me)- pyrrolidine-oxazaphospholidine]

R' = Ac, R = H
R' = Ac, R = OMe
R' = Ac, R = OCH₂CH₂OMe
R' = Ac, R = F
R' = iBu, R = H
R' = iBu, R = OMe
R' = iBu, R = OCH₂CH₂OMe
R' = iBu, R = F

[Structure: DMTrO-deoxyribose-purine with O-CH₂CH₂CN and NH-isobutyryl, 2'-OR, 3'-O-X]

TABLE 1-continued

Example phosphoramidites.

[Structure: X = phosphoramidite with Ph2(Me)Si-CH2- pyrrolidine-oxazaphospholidine, opposite stereochemistry]

R = H
R = OMe
R = OCH₂CH₂OMe
R = F

[Structure: X = phosphoramidite with Ph(Me)- pyrrolidine-oxazaphospholidine, opposite stereochemistry]

R = H
R = OMe
R = OCH₂CH₂OMe
R = F

[Structure: DMTrO-deoxyribose-cytosine with NHR', 2'-OR, 3'-O-X]

[Structure: X = phosphoramidite with Ph2(Me)Si-CH2- pyrrolidine-oxazaphospholidine]

R' = Ac, R = H
R' = Ac, R = OMe
R' = Ac, R = OCH₂CH₂OMe
R' = Ac, R = F
R' = iBu, R = H
R' = iBu, R = OMe
R' = iBu, R = OCH₂CH₂OMe
R' = iBu, R = F

[Structure: X = phosphoramidite with Ph(Me)- pyrrolidine-oxazaphospholidine]

TABLE 1-continued
Example phosphoramidites.
R' = Ac, R = H
R' = Ac, R = OMe
R' = Ac, R = OCH$_2$CH$_2$OMe
R' = Ac, R = F
R' = iBu, R = H
R' = iBu, R = OMe
R' = iBu, R = OCH$_2$CH$_2$OMe
R' = iBu, R = F
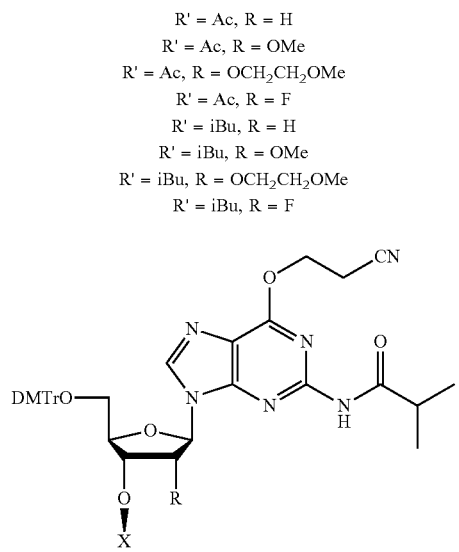
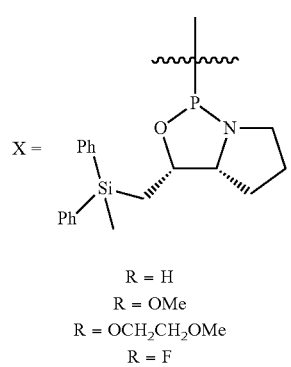
R = H
R = OMe
R = OCH$_2$CH$_2$OMe
R = F
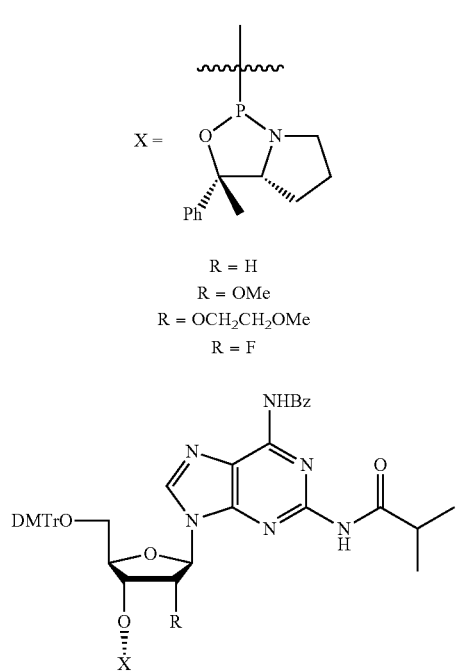
TABLE 1-continued
Example phosphoramidites.
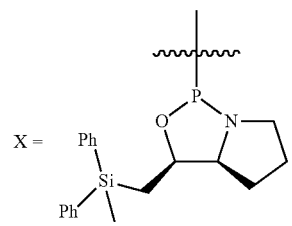 [SMILES: *P1O[C@H](C[Si](C)(c2ccccc2)c2ccccc2)[C@@H]2CCCN21]
R = H
R = OMe
R = OCH$_2$CH$_2$OMe
R = F
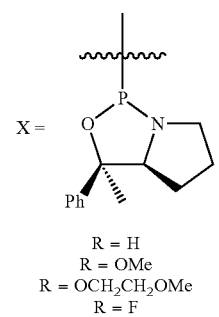
R = H
R = OMe
R = OCH$_2$CH$_2$OMe
R = F
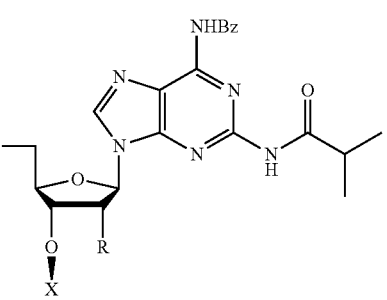
R = H
R = OMe
R = OCH$_2$CH$_2$OMe
R = F
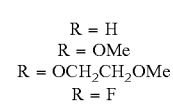
R = H
R = OMe
R = OCH$_2$CH$_2$OMe
R = F In some embodiments, the present disclosure provides new technologies, e.g., compounds, compositions, methods, etc., for preparing a phosphoramidite and/or an oligonucleotide. In some embodiments, the present disclosure provides new technologies for purifying phosphoramidite. In some embodiments, provided technologies greatly improve efficiency of phosphoramidite synthesis, and/or significantly decrease the cost of phosphoramidite, and oligonucleotides, compositions and medicaments prepared therefrom. Among other things, provided technologies can be utilized to prepare phosphoramidites for a variety of oligonucleotide synthesis methods, including but not limited to those described in WO/2011/005761, US/2012/0316224, WO/2013/012758, US/2014/0194610, WO/2014/012081, US/2015/0211006, WO/2015/107425, US/2017/0037399, WO/2010/064146, US/2011/0294124, WO/2014/010250, US/2015/0197540, WO/2011/108682, US/2013/0184450, WO/2012/039448, US/2013/0178612, WO/2012/073857, or US/2013/0253178, the methods of each of which are hereby incorporated by reference. In some embodiments, methods provided herewith are particularly useful for preparing chirally controlled oligonucleotide compositions, such as those described in WO/2014/012081, WO/2015/107425, etc.

As demonstrated herein, provided technologies can surprisingly improve yields and/or purity of phosphoramidites. In some embodiments, the absolute improvement is about 5%, 10%, 15%, 20%, 25%, 30%, 35%, 40%, 45%, 50%, 55%, 60%, 65%, 70%, 75%, 80%, 85%, 90%, 95% or more. In some embodiments, the absolute improvement is greater than about 5%, 10%, 15%, 20%, 25%, 30%, 35%, 40%, 45%, 50%, 55%, 60%, 65%, 70%, 75%, 80%, 85%, 90%, 95% or more. In some embodiments, yield from a provided technology is greater than about 80%, while yield from a corresponding technology without pre-treatment is less than about 60% (corresponding to an absolute improvement of greater than 20%). In some embodiments, the improvement relative to a corresponding technology without pre-treatment is greater than about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300%, 400%, 500%, 600%, 700%, 800%, 900% or more.

In some embodiments, provided technologies may be conducted, partially or wholly, at a temperature higher and/or lower than room temperature. In some embodiments, provided technologies comprise procedures at temperature higher than room temperature, e.g., at 30, 40, 50, 60, 70, 80, 90, 100° C. or higher. In some embodiments, provided technologies comprise procedures at temperature lower than room temperature, e.g., at 15, 10, 5, 0, −5, −10° C. or lower. In some embodiments, purification, e.g., chromatography purification of a phosphoramidite using a purification medium (often pre-treated), is conducted at a temperature higher than room temperature. In some embodiments, purification, e.g., chromatography purification of a phosphoramidite using a purification medium (often pre-treated), is conducted at a temperature lower than room temperature. In some embodiments, a higher and/or lower temperature is controlled so that temperature variations are controlled within a range.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}C-$ or $^{13}C-$ or $^{14}C-$ enriched carbon are within the scope of this disclosure. Such compounds are useful, for example, as analytical tools or probes in biological assays.

As used herein and in the claims, the singular forms "a", "an", and "the" include the plural reference unless the context clearly indicates otherwise. Thus, for example, a reference to "a compound" includes a plurality of such compounds.

In some embodiments, the present disclosure provides the following embodiments:

1. A method for purifying a compound, comprising steps of:
   a) removing water from a purification medium;
   b) contacting the purification medium with the compound; and
   c) optionally using the purification medium to purify the compound.

2. A method for purifying a compound, comprising steps of:
   a) removing water from a purification medium;
   b) contacting the purification medium with the compound; and
   c) using the purification medium to purify the compound.

3. A method for purifying a compound, comprising steps of:
   a) removing water from a purification medium;
   b) using the purification medium to purify the compound.

4. A method for improving recovery rate of a compound, comprising steps of:
   a) removing water from a purification medium;
   b) adding the compound to the purification medium; and
   c) eluting the compound from the purification medium with a solvent system;
   wherein the recovery rate is higher than a reference recovery rate when step a) is absent.

5. A method for decreasing decomposition of a compound when the compound contacts a purification medium, comprising:
   removing water from the purification medium.

6. A method comprising steps of:
   a) removing water from a purification medium;
   b) contacting the purification medium with a compound; and
   c) optionally using the purification medium to purify the compound.

7. A method comprising steps of:
   a) removing water from a purification medium;
   b) using the purification medium to purify a compound.

8. A method comprising steps of:
   contacting a purification medium with a compound, wherein the medium is pre-treated, wherein the pre-treatment comprises removing water.

9. A method comprising steps of:
   purifying a compound using a pre-treated purification medium, wherein the medium is pre-treated, wherein the pre-treatment comprises removing water.

10. A method comprising steps of:
    a) removing water from a purification medium;
    b) contacting the purification medium with a compound; and
    c) using the purification medium to purify the compound.

11. A method comprising steps of:
 a) mechanically removing water from a purification medium;
 b) contacting the purification medium with a compound; and
 c) optionally using the purification medium to purify a compound.

12. A method comprising steps of:
 a) mechanically removing water from a purification medium;
 b) contacting the purification medium with a compound; and
 c) using the purification medium to purify a compound.

13. The method of any one of the preceding embodiments, wherein the compound is a phosphoramidite.

14. A method for purifying a phosphoramidite, comprising steps of:
 a) removing water from a purification medium;
 b) contacting the purification medium with a phosphoramidite; and
 c) optionally using the purification medium to purify a phosphoramidite.

15. A method for purifying a phosphoramidite, comprising steps of:
 a) removing water from a purification medium;
 b) using the purification medium to purify the phosphoramidite.

16. A method for purifying a phosphoramidite, comprising steps of:
 a) removing water from a purification medium;
 b) contacting the purification medium with a phosphoramidite; and
 c) using the purification medium to purify a phosphoramidite.

17. A method for improving recovery rate of a phosphoramidite, comprising steps of:
 a) removing water from a purification medium;
 b) adding the phosphoramidite to the purification medium; and
 c) eluting the phosphoramidite from the purification medium with a solvent system;
 wherein the recovery rate is higher than a reference recovery rate when step a) is absent.

18. The method of embodiment 4 or 17, wherein the difference between the improved recovery rate and the reference recovery rate is at least about 10%, 20%, 30%, 40% or 50%.

19. A method for decreasing decomposition of a phosphoramidite when the phosphoramidite contacts a purification medium, comprising:
 a) removing water from the purification medium.

20. A method comprising steps of:
 a) removing water from a purification medium;
 b) contacting the purification medium with a phosphoramidite; and
 c) optionally using the purification medium to purify the phosphoramidite.

21. A method comprising steps of:
 a) removing water from a purification medium;
 b) using the purification medium to purify a phosphoramidite.

22. A method comprising steps of:
 a) removing water from a purification medium;
 b) contacting the purification medium with a phosphoramidite; and
 c) using the purification medium to purify the phosphoramidite.

23. A method comprising steps of:
 a) mechanically removing water from a purification medium;
 b) contacting the purification medium with a phosphoramidite; and
 c) optionally using the purification medium to purify a phosphoramidite.

24. A method comprising steps of:
 a) mechanically removing water from a purification medium;
 b) using the purification medium to purify a phosphoramidite.

25. A method comprising steps of:
 a) mechanically removing water from a purification medium;
 b) contacting the purification medium with a phosphoramidite; and
 c) using the purification medium to purify a phosphoramidite.

26. In a method of purifying a phosphoramidite using a purification medium, the improvement comprising pre-treatment of the purification medium with a process that removes water from the purification medium.

27. The method of any one of the preceding embodiments, wherein removing water from the purification medium comprises heating the purification medium.

28. The method of any one of the preceding embodiments, wherein removing water from the purification medium comprises contacting the purification medium with a hygroscopic solvent system.

29. The method of embodiment 28, wherein the hygroscopic solvent system consists of one hygroscopic solvent.

30. The method of embodiment 28, wherein the hygroscopic solvent system comprises one hygroscopic solvent and another solvent.

31. The method of embodiment 30, wherein the hygroscopic solvent system consists of two or more solvents, wherein each solvent is independently a hygroscopic solvent.

32. The method of any one of the preceding embodiments, wherein the hygroscopic solvent is selected from acetaldehyde, acetic acid, acetone, acetonitrile, 1,2-butanediol, 1,3-butanediol, 1,4-butanediol, 2-butoxyethanol, butyric acid, diethanolamine, diethylenetriamine, dimethyl carbonate, dimethylformamide, dimethoxyethane, dimethyl sulfoxide, 1,4-dioxane, ethanol, ethyl acetate, ethylamine, ethylene glycol, formic acid, furfuryl alcohol, glycerol, methanol, methyl diethanolamine, methyl isocyanide, 1-propanol, 1,3-propanediol, 1,5-pentanediol, 2-propanol, propanoic acid, propylene glycol, pyridine, tetrahydrofuran, and triethylene glycol.

33. The method of any one of the preceding embodiments, wherein the hygroscopic solvent is selected from acetaldehyde, acetic acid, acetone, acetonitrile, 1,2-butanediol, 1,3-butanediol, 1,4-butanediol, 2-butoxyethanol, butyric acid, diethanolamine, diethylenetriamine, dimethylformamide, dimethoxyethane, dimethyl sulfoxide, 1,4-dioxane, ethanol, ethylamine, ethylene glycol, formic acid, furfuryl alcohol, glycerol, methanol, methyl diethanolamine, methyl isocyanide, 1-propanol, 1,3-propanediol, 1,5-pentanediol, 2-propanol, propanoic acid, propylene glycol, pyridine, tetrahydrofuran, and triethylene glycol.

34. The method of any one of the preceding embodiments, wherein the hygroscopic solvent is selected from methanol and ethanol.

35. The method of any one of the preceding embodiments, wherein the hygroscopic solvent is methanol.

36. The method of any one of embodiments 1-35, wherein the hygroscopic solvent is ethanol.
37. The method of any one of embodiments 1-35, wherein the hygroscopic solvent is isopropanol.
38. The method of any one of embodiments 1-35, wherein the hygroscopic solvent is acetone.
39. The method of any one of embodiments 1-35, wherein the hygroscopic solvent is acetonitrile.
40. The method of any one of embodiments 1-35, wherein the hygroscopic solvent is dimethyl carbonate.
41. The method of any one of embodiments 1-35, wherein the hygroscopic solvent is ethyl acetate.
42. A method comprising steps of:
   a) pre-treating a purification medium;
   b) contacting the purification medium with a phosphoramidite; and
   c) optionally using the purification medium to purify a phosphoramidite.
43. A method comprising steps of:
   a) pre-treating a purification medium; and
   b) contacting the purification medium with a phosphoramidite.
44. A method comprising steps of:
   a) pre-treating a purification medium; and
   b) using the purification medium to purify a phosphoramidite.
45. A method comprising steps of:
   a) pre-treating a purification medium comprising silica;
   b) contacting the purification medium with a phosphoramidite; and
   c) optionally using the purification medium to purify a phosphoramidite.
46. A method comprising steps of:
   a) pre-treating a purification medium comprising silica; and
   b) contacting the purification medium with a phosphoramidite.
47. A method comprising steps of:
   a) pre-treating a purification medium comprising silica; and
   b) using the purification medium to purify a phosphoramidite.
48. In a method of purifying a phosphoramidite using a purification medium, the improvement comprising pre-treatment of the purification medium.
49. In a method of purifying a phosphoramidite using a purification medium comprising silica, the improvement comprising pre-treatment of the purification medium.
50. The method of any one of embodiments 42-49, wherein the pre-treatment comprises heating the purification medium.
51. The method of any one of embodiments 42-50, wherein the pre-treatment comprises contacting the purification medium with a first solvent system.
52. The method of any one of embodiments 42-50, wherein the pre-treatment comprises contacting the purification medium with a first solvent system, wherein the first solvent system comprises a hygroscopic solvent.
53. The method of any one of embodiments 42-50, wherein the pre-treatment comprises contacting the purification medium with a first solvent system, wherein the first solvent system comprises an alcohol.
54. The method of any one of embodiments 42-53, wherein the first solvent system comprises methanol.
55. The method of any one of embodiments 42-52, wherein the hygroscopic solvent is ethanol.
56. The method of any one of embodiments 42-52, wherein the hydroscopic solvent is isopropanol.
57. The method of any one of embodiments 42-52, wherein the hydroscopic solvent is dimethyl carbonate.
58. The method of any one of embodiments 42-52, wherein the hydroscopic solvent is acetone.
59. The method of any one of embodiments 42-52, wherein the hydroscopic solvent is acetonitrile.
60. The method of any one of embodiments 42-52, wherein the hydroscopic solvent is ethyl acetate.
61. The method of any one of embodiments 42-54, wherein the first solvent system consists of one solvent.
62. The method of any one of embodiments 42-62, wherein the first solvent system comprises a modifier.
63. The method of embodiment 62, wherein the modifier is triethylamine up to 50% v/v.
64. The method of any one of the preceding embodiments, further comprising:
   a1) equilibrating the purification medium with a second solvent system before contacting the purification system with a phosphoramidite.
65. The method of any one of the preceding embodiments, wherein the second solvent system is less polar than the first solvent system.
66. The method of any one of the preceding embodiments, wherein the second solvent system comprising a lower percentage (v/v) of at least one alcohol compared to the first solvent system.
67. The method of any one of the preceding embodiments, wherein the second solvent system comprises no alcohol.
68. The method of any one of the preceding embodiments, wherein the second solvent system comprises hexanes or ethyl acetate, and optionally a modifier.
69. The method of any one of the preceding embodiments, wherein the second solvent system comprises hexanes, ethyl acetate and an organic base.
70. The method of any one of the preceding embodiments, wherein the second solvent system comprises hexanes, ethyl acetate and triethylamine.
71. The method of any one of the preceding embodiments, wherein the purification medium is used for purifying a phosphoramidite, and a third solvent system is used to elute the phosphoramidite from the purification medium.
72. The method of any one of the preceding embodiments, wherein the third solvent system is less polar than the first solvent system.
73. The method of any one of the preceding embodiments, wherein the third solvent system comprising a lower percentage (v/v) of at least one alcohol compared to the first solvent system.
74. The method of any one of the preceding embodiments, wherein the third solvent system is less polar than the second solvent system.
75. The method of any one of the preceding embodiments, wherein the third solvent system is the same as the second solvent system.
76. The method of any one of the preceding embodiments, wherein a gradient is used to elute the phosphoramidite from the purification medium.
77. The method of any one of the preceding embodiments, wherein the solvent system at the beginning of the gradient elution is the same as the second solvent system at the end of equilibration.
78. The method of any one of the preceding embodiments, wherein the purification medium is silica gel.

79. The method of any one of the preceding embodiments, wherein the purification medium is silica gel having a particle size of 50 μM or more.
80. The method of any one of the preceding embodiments, wherein the purification medium is silica gel having a particle size of 50 μM.
81. The method of any one of the preceding embodiments, wherein the first solvent system comprises a base.
82. The method of any one of the preceding embodiments, wherein the third solvent system comprises a base, ethyl acetate and hexanes.
83. The method of any one of the preceding embodiments, wherein the base is triethylamine.
84. The method of any one of the preceding embodiments, wherein the base is up to 50% v/v.
85. The method of any one of the preceding embodiments, wherein the base is 5% v/v.
86. The method of any one of the preceding embodiments, comprising chromatography purification of the phosphoramidite using the purification medium.
87. The method of any one of the preceding embodiments, comprising chromatography purification of the phosphoramidite using the purification medium at a temperature higher than room temperature.
88. The method of any one of the preceding embodiments, comprising chromatography purification of the phosphoramidite using the purification medium at a temperature lower than room temperature.
89. A composition comprising:
  a) a purification medium pre-treated by step a) of any one of the preceding embodiments;
  b) a phosphoramidite.
90. The composition of embodiment 89, wherein a de-activated purification medium is silica gel.
91. A composition comprising:
  a) silica pre-treated by step a) of any one of the preceding embodiments;
  b) a phosphoramidite.
92. The composition of any one of embodiments 89-91, wherein the purification medium pretreated is silica gel pre-treatment with a hygroscopic solvent system.
93. The composition of any one of embodiment 92, wherein the hygroscopic solvent system is a hygroscopic solvent system or a first solvent system of any one of the preceding embodiments.
94. The composition of any one of embodiments 89-91, wherein the purification medium is equilibrated with a second solvent system.
95. The method or composition of any one of the preceding embodiments, wherein the phosphoramidite is a nucleoside phosphoramidite.
96. The method or composition of any one of the preceding embodiments, wherein the phosphoramidite has the structure of formula II:

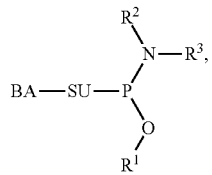

I wherein:
BA is R, or an optionally substituted group selected from a 3-30 membered cycloaliphatic ring, a 6-30 membered aryl ring, a 3-30 membered heterocyclyl having 1-10 heteroatoms independently selected from oxygen, nitrogen, sulfur, phosphorus and silicon, a 5-30 membered heteroaryl ring having 1-10 heteroatoms independently selected from oxygen, nitrogen, sulfur, phosphorus and silicon, a natural nucleobase moiety and a modified nucleobase moiety;
SU is a sugar moiety, a modified sugar moiety, -L-O— or

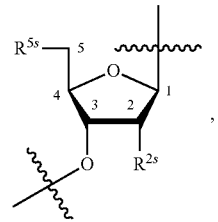

wherein SU is connected to the phosphorus atom in formula I through the oxygen atom;
L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
$R^{5s}$ is R' or —OR;
$R^{2s}$ is —F, —CN, —N$_3$, —NO, —NO$_2$, —R'—OR, —SR', —N(R')$_2$, -L-R', —O-L-OR', —O-L-SR', or —O-L-N(R')$_2$, or $R^{2s}$ is L connecting C2 with C1, C2, C3, C4 or C5;
-Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;
each of $R^1$, $R^2$, and $R^3$ is independently R', or two or three of $R^1$, $R^2$, and $R^3$ are taken together with their intervening atoms to form:

Ring A is an optionally substituted multivalent, monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon;
each $R^s$ is independently R' or -L-R;
t is 0-5;

each R' is independently —R, —C(O)R, —CO$_2$R, or —SO$_2$R, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and each R is independently hydrogen, or an optionally substituted group selected from C$_{1-30}$ aliphatic, C$_{1-30}$ heteroaliphatic having 1-10 heteroatoms independently selected from oxygen, nitrogen, sulfur, phosphorus and silicon, a 6-30 membered aryl ring, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

97. The method or composition of embodiment 88, wherein BA is an optionally substituted group selected from a 3-30 membered cycloaliphatic ring, a 6-30 membered aryl ring, a 3-30 membered heterocyclyl having 1-10 heteroatoms independently selected from oxygen, nitrogen, sulfur, phosphorus and silicon, a 5-30 membered heteroaryl ring having 1-10 heteroatoms independently selected from oxygen, nitrogen, sulfur, phosphorus and silicon, a natural nucleobase moiety and a modified nucleobase moiety.

98. The method or composition of any one of the preceding embodiments, wherein the phosphoramidite has the structure of formula II:

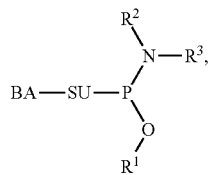

wherein:

BA is an optionally substituted group selected from C$_{1-30}$ cycloaliphatic, C$_{6-30}$ aryl, C$_{3-30}$ heterocyclyl having 1-10 heteroatoms independently selected from oxygen, nitrogen, sulfur, phosphorus and silicon, C$_{5-30}$ heteroaryl having 1-10 heteroatoms independently selected from oxygen, nitrogen, sulfur, phosphorus and silicon, a natural nucleobase moiety and a modified nucleobase moiety;

SU is -L-O— or

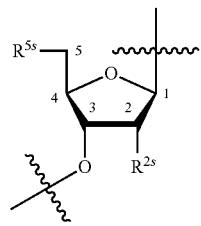

wherein SU is connected to the phosphorus atom in formula I through the oxygen atom;

L is a covalent bond, or a bivalent, optionally substituted, linear or branched group selected from C$_{1-30}$ aliphatic and C$_{1-30}$ heteroaliphatic group having 1-10 heteroatoms independently selected from oxygen, nitrogen, sulfur, phosphorus and silicon, wherein one or more methylene units are optionally and independently replaced by an optionally substituted C$_{1-6}$ alkylene, C$_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

R$^{5s}$ is R' or —OR;

R$^{2s}$ is —F, —CN, —N$_3$, —NO, —NO$_2$, —R'—OR, —SR', —N(R')$_2$, —O-L-OR', —O-L-SR', or —O-L-N(R')$_2$, or R$^{2s}$ is L connecting C2 with C1, C2, C3, C4 or C5;

-Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;

each of R$^1$, R$^2$, and R$^3$ is independently R', or two or three of R$^1$, R$^2$, and R$^3$ are taken together with their intervening atoms to form:

Ring A is an optionally substituted multivalent, monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon;

each R$^s$ is independently R' or -L-R;

t is 0-5;

each R' is independently —R, —C(O)R, —CO$_2$R, or —SO$_2$R, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and each R is independently hydrogen, or an optionally substituted group selected from C$_{1-30}$ aliphatic, C$_{1-30}$ heteroaliphatic having 1-10 heteroatoms independently selected from oxygen, nitrogen, sulfur, phosphorus and silicon, C$_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

99. The method or composition of any one of embodiments 96-98, wherein BA is an optionally substituted group selected from C$_{1-30}$ cycloaliphatic, C$_{6-30}$ aryl, C$_{3-30}$ heterocyclyl, C$_{5-30}$ heteroaryl, and a natural nucleobase moiety.

100. The method or composition of any one of embodiments 96-98, wherein BA is an optionally substituted group, which group is formed by removing a —H from

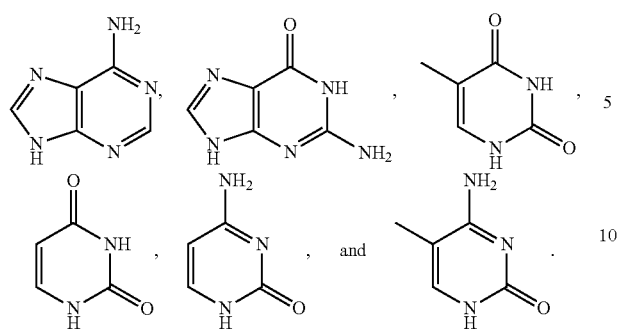

101. The method or composition of embodiment 100, wherein BA is an optionally substituted group which group is selected from

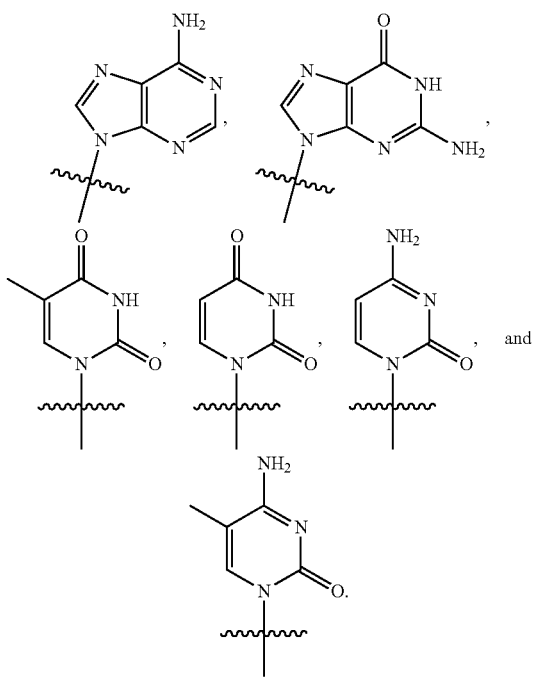

102. The method or composition of any one of embodiments 96-99, wherein BA is an optionally substituted guanine residue wherein its $O^6$ is unprotected.
103. The method or composition of any one of embodiments 96-99, wherein BA is a modified base.
104. The method or composition of any one of embodiments 96-103, wherein SU is a modified or unmodified sugar moiety.
105. The method or composition of any one of embodiments 96-104, wherein SU is -L-O—.
106. The method or composition of any one of embodiments 96-105, wherein SU is -L-O—, and L is optionally substituted 5-10 membered heterocyclylene having one oxygen atom.
107. The method or composition of any one of embodiments 96-106, wherein SU is -L-O—, and L is optionally substituted 5-membered heterocyclylene having one oxygen atom.
108. The method or composition of any one of embodiments 96-106, wherein SU is -L-O—, and L is optionally substituted 7-10 membered bicyclic heterocyclylene having two oxygen atoms.

109. The method or composition of any one of embodiments 96-106, wherein SU is

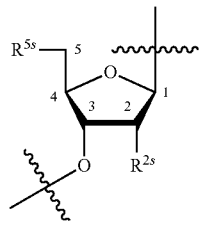

110. The method or composition of embodiment 109, wherein $R^5$ is —OR'.
111. The method or composition of any one of embodiments 109-110, wherein $R^5$ is —ODMTr.
112. The method or composition of any one of embodiments 109-111, wherein $R^{2s}$ is —H.
113. The method or composition of any one of embodiments 109-111, wherein $R^{2s}$ is —F.
114. The method or composition of any one of embodiments 109-111, wherein $R^{2s}$ is —OR'.
115. The method or composition of any one of embodiments 109-111, wherein $R^{2s}$ is —O-L-OR'.
116. The method or composition of any one of embodiments 109-111, wherein $R^{2s}$ is —OMe.
117. The method or composition of any one of embodiments 109-111, wherein $R^{2s}$ is —OCH$_2$CH$_2$OMe.
118. The method or composition of any one of embodiments 109-111, wherein $R^{2s}$ is L connecting C2 with C1, C2, C3, C4 or C5.
119. The method or composition of any one of embodiments 109-111, $R^{2s}$ is L connecting C2 with C4.
120. The method or composition of embodiment 118 or 119, wherein L is (C2)—O-(optionally substituted methylene)-.
121. The method or composition of embodiment 120, wherein L is (C2)—O-(optionally substituted methylene)-, wherein the methylene group is substituted with ethyl.
122. The method or composition of embodiment 121, wherein the carbon atom of the methylene group is S.
123. The method or composition of embodiment 121, wherein the carbon atom of the methylene group is R.
124. The method or composition of any one of embodiments 96-123, wherein $R^2$ and $R^3$ are taken together with the intervening nitrogen atom to form

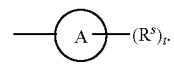

125. The method or composition of any one of embodiments 96-123, wherein $R^1$ and one of $R^2$ and $R^3$ are taken together with their intervening nitrogen, phosphorus and oxygen atoms to form

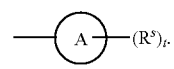

126. The method or composition of any one of embodiments 96-123, wherein $R^1$, $R^2$, and $R^3$ are taken together with their intervening nitrogen, phosphorus and oxygen atoms to form

127. The method or composition of embodiment 125 or 126, wherein Ring A comprises a ring system having the backbone structure of

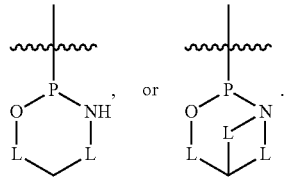

128. The method or composition of embodiment 126 or 127, wherein Ring A comprises a ring system having the backbone structure of

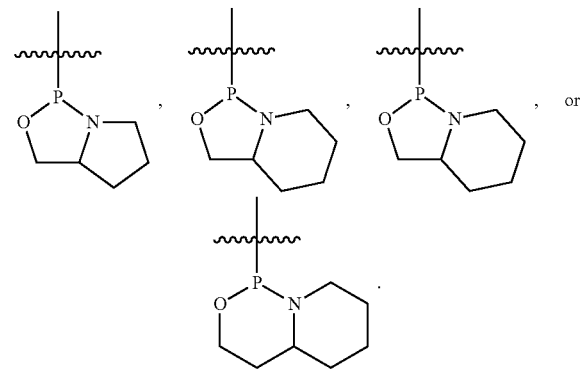

129. The method or composition of any one of embodiments 96-128, wherein t is 0.
130. The method or composition of any one of embodiments 96-128, wherein t is 1-5.
131. The method or composition of any one of embodiments 96-128, wherein one $R^s$ is R' or -L-R' wherein -L- is a bivalent, optionally substituted $C_{1-30}$ heteroaliphatic group.
132. The method or composition of any one of embodiments 96-128, wherein one $R^s$ is —$CH_2Si(Ph)_2CH_3$.

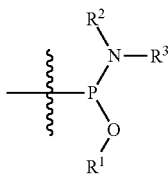

133. The method or composition of any one of embodiments 96-132, wherein $R^1$ comprises one or more chiral elements and is asymmetric.
134. The method or composition of any one of embodiments 96-133, wherein when used in oligonucleotide synthesis, the phosphoramidite can deliver diastereoselectivity greater than about 50%, 60%, 70%, 80%, 90%, 91%, 92%, 93%, 94%, 95%, 96%, 97%, 98% or 99% at the newly formed P-chiral center, optionally with greater than about 50%, 60%, 70%, 80%, 90%, 91%, 92%, 93%, 94%, 95%, 96%, 97%, 98% or 99% yield.

135. The method or composition of embodiment 134, wherein the oligonucleotide synthesis method is one described in WO/2011/005761, WO/2013/012758, WO/2014/012081, WO/2015/107425, WO/2010/064146, WO/2014/010250, WO/2011/108682, WO/2012/039448, or WO/2012/073857.
136. The method or composition of any one of embodiments 96-134, wherein

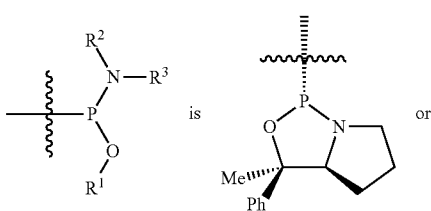

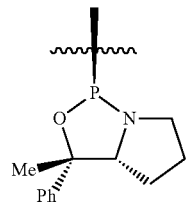

137. The method or composition of any one of embodiments 96-134, wherein

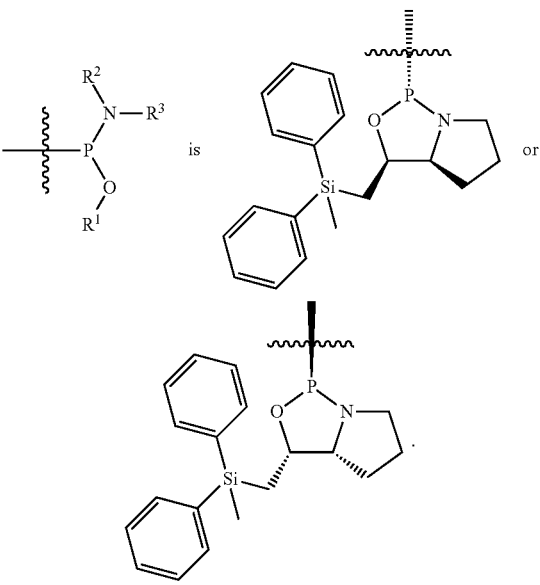

138. The method or composition of any one of embodiments 1-137, wherein the phosphoramidite is one described in WO/2011/005761, WO/2013/012758, WO/2014/012081, WO/2015/107425, WO/2010/064146, WO/2014/010250, WO/2011/108682, WO/2012/039448, or WO/2012/073857.

139. The method or composition of any one of embodiments 1-137, wherein the phosphoramidite is selected from
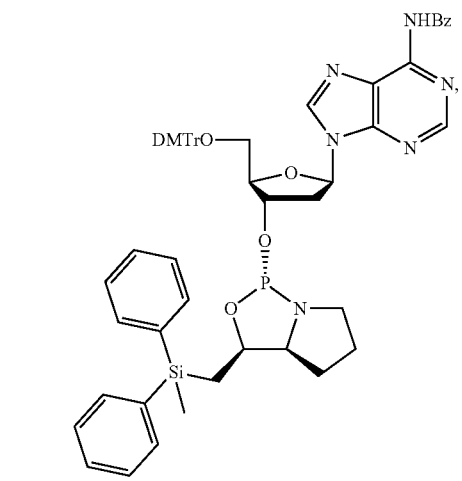
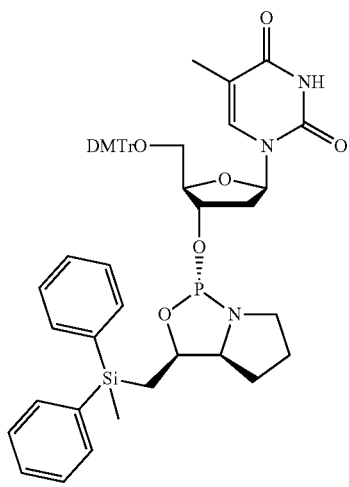
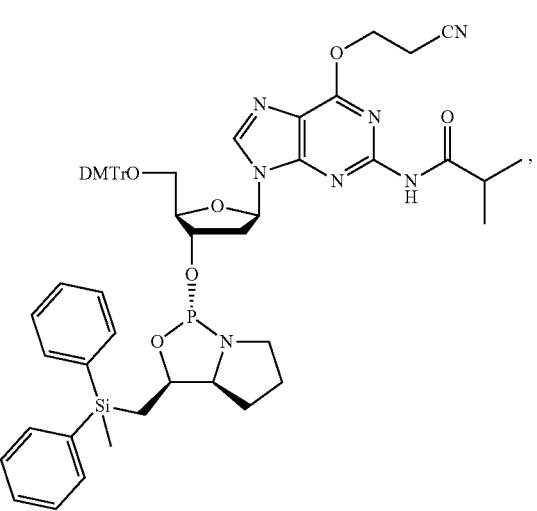
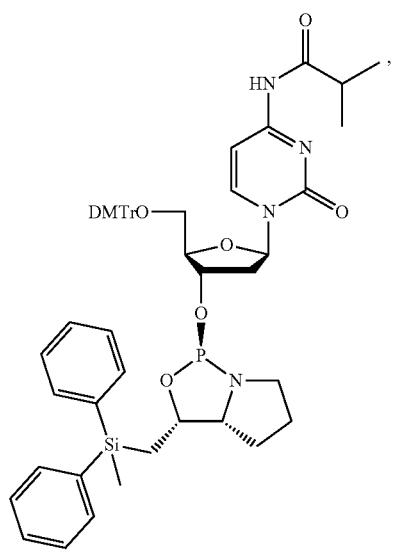
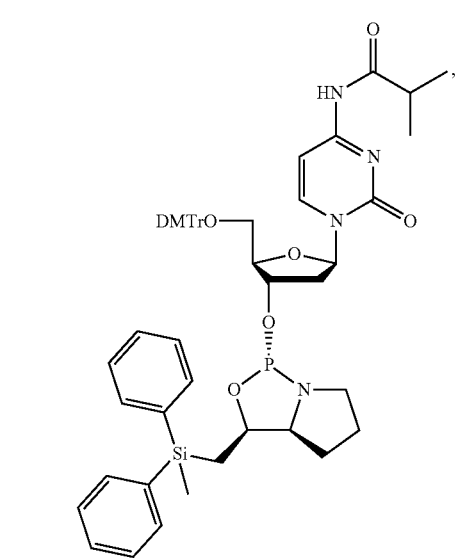
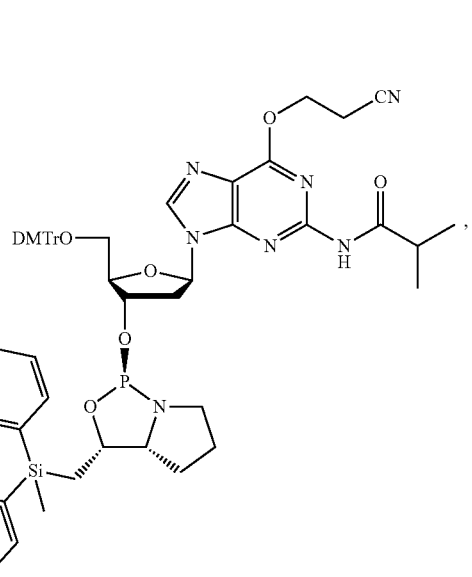

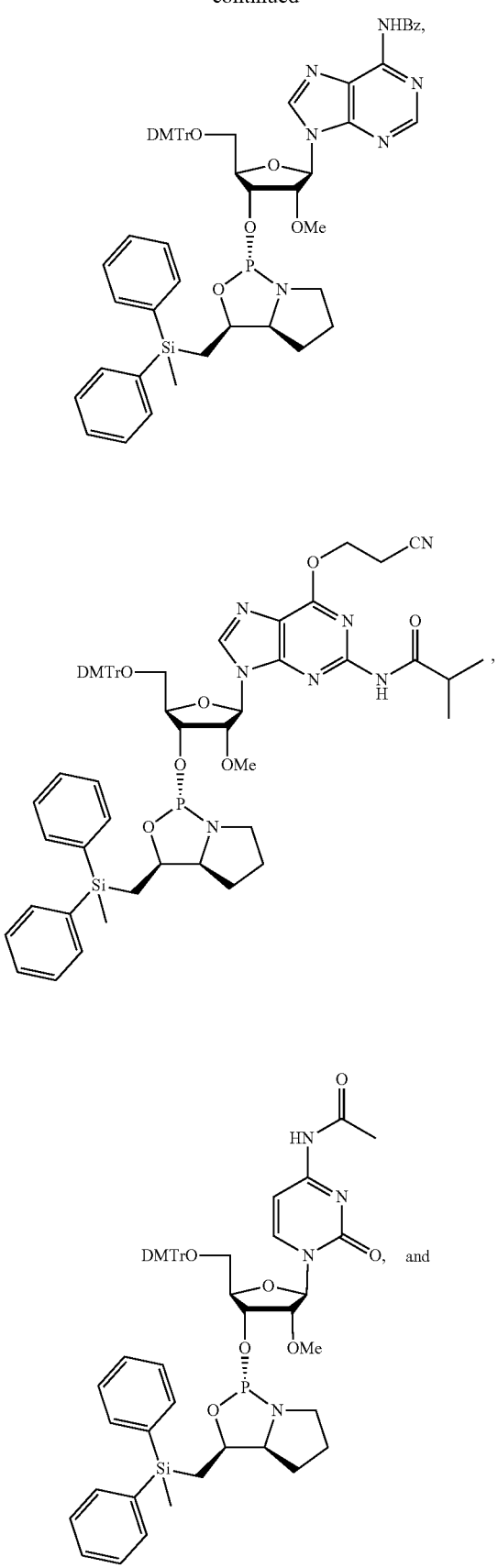

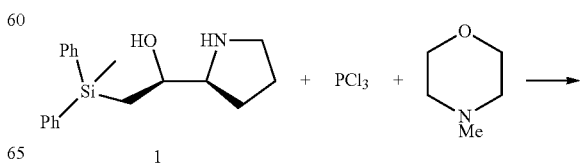

140. The method or composition of any one of embodiments 1-137, wherein the phosphoramidite is selected from Table 1.

141. The method or composition of any one of embodiments 96-132, wherein

142. A method for preparing an oligonucleotide, comprising the method of any one of the preceding embodiments.

143. A method for preparing an oligonucleotide, comprising providing a composition of any one of the preceding embodiments.

144. The method of embodiment 142 or 143, wherein the method for preparing an oligonucleotide is one described in WO/2011/005761, WO/2013/012758, WO/2014/012081, WO/2015/107425, WO/2010/064146, WO/2014/010250, WO/2011/108682, WO/2012/039448, or WO/2012/073857.

EXEMPLIFICATION

Non-limiting examples were provided below. A person of ordinary skill in the art appreciates that other phosphoramidites can similarly be prepared and purified with greatly improved yields and/or purity as illustrated herein.

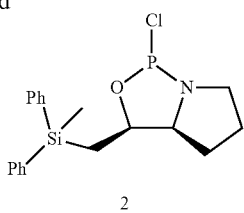

(S)-2-(methyldiphenylsilyl)-1-((S)-pyrrolidin-2-yl)ethanol, 1, (28.3 g, 91.0 mmol) was dried by azeotropic evaporation with anhydrous toluene (110 mL) and left under high vacuum overnight. A solution of this dried 1 (28.3 g, 91.0 mmol) and 4-methylmorpholine (18.59 g, 184 mmol) dissolved in anhydrous toluene (150 mL) was added via cannula to an ice-cold solution of trichlorophosphine (12.6 g, 8.0 mL, 92 mmol) dissolved in anhydrous toluene (80 mL) under argon and the reaction mixture was stirred at 0° C. for 40 min. The reaction mixture was warmed to room temperature (rt) and stirred for 1 hour, then the white precipitate was filtered under vacuum back flushing with argon using a Schlenk air-free filter tube. The solvent was removed under vacuum at 25° C. and the crude semi solid thus obtained was dried under high vacuum for 12 h and used in the next step of the synthesis without further purification.

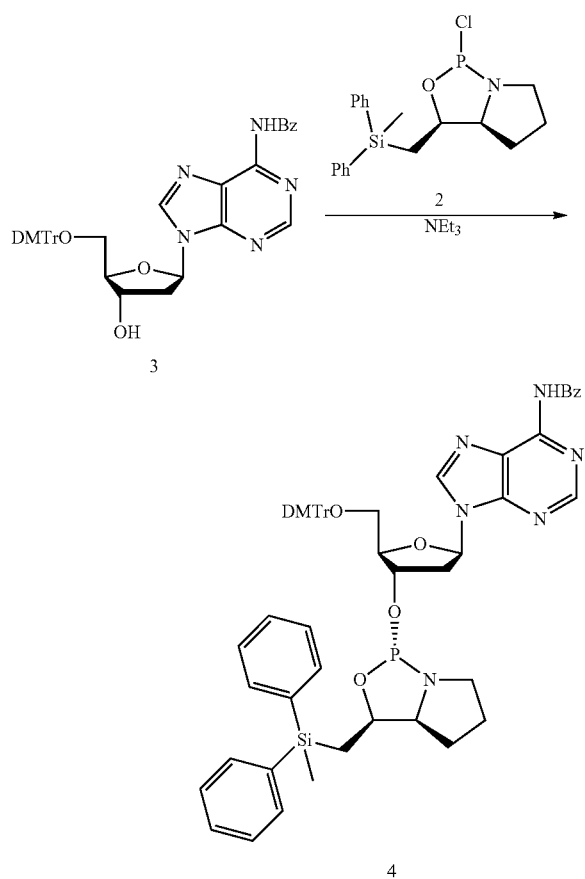

The nucleoside 5'-DMT-dA(N6-Bz), 3, (40 g, 60.8 mmol) was dried by azeotropic evaporation first with anhydrous pyridine (60 mL) and then with anhydrous toluene (110 mL) and dried under high vacuum for 24 hours. This dried compound was dissolved in THF (140 mL) followed by the addition of triethylamine (30.8 g, 42.4 mL, 304 mmol) then cooled to −78° C. using an IPA/dry ice bath. A THF solution (80 mL) of the crude compound 2 (obtained as described above) was added via cannula over 15 min then the mixture was gradually warmed to rt. After 1 hr at rt, TLC indicated complete conversion of SM to product. The mixture was cooled at 0° C. then CHCl$_3$ (800 mL) was added, followed sat NaHCO$_3$ (400 mL). The organic layer was separated and washed with sat NaHCO$_3$ (2×400 mL). The combined aqueous layers were extracted with CHCl$_3$ (200 mL), then washed with sat NaHCO$_3$ (200 mL). The combined CHCl$_3$ extract was dried over anhydrous Na$_2$SO$_4$, filtered and the volatiles were removed by rotary evaporation at 25° C. to afford the light yellowish solid. 71 g crude compound 4.

Purification Methods

The above crude material was purified on a Combiflash instrument from Teledyne using either a pre-treated silica gel column, or a non-pre-treated silica gel column. In either case, every other feature of the separation methods was identical.

Purification by Using Non-Pre-Treated Silica Column 3.0 g of crude compound 4 was dissolved in a 2:1 volume:volume mixture of methylene chloride:hexanes containing 5% Et$_3$N then loaded onto a 24 g silica column which had been equilibrated with 5 column volumes of 20% Hexanes/EtOAc containing 5% Et$_3$N. After loading the sample on the column, the purification process was run using the following gradient: 20 to 80% EtOAc/hexanes containing 5% Et$_3$N as shown in the chromatogram (FIG. 1. Fractions which were homogeneous by TLC, 14-22 shown in FIG. 1, were pooled together and the volatiles removed by rotary evaporation, then residual solvent was removed under high vacuum over 18 h to afford a colorless white solid (yield of pure compound 4=1.3 g, 56%). In some embodiments, later fractions showed decompositions while earlier fractions showed non-polar impurities. Without the intention to be bound by any particular theory, in some instances the decomposition is due to transformations at the phosphoramidite group.

Purification by Using Pre-Treated Silica Column

The exact method described for the non-pre-treated method was followed, except that in this case, the 24 g silica gel column was first pre-treated by eluting with 5 column volumes of methanol, before equilibration with 5 column volumes of 20% EtOAc/hexanes containing 5% Et$_3$N. In this case, a colorless white solid resulting from pooling and evaporation of fractions 15-23 was similarly obtained (yield of pure compound 4=2.0 g, 83%). In some embodiments, pre-treated purification medium provides better separation, better peak shapes and/or less tailing as demonstrated by the examples.

The product was confirmed by $^{31}$P-NMR recorded in CDCl$_3$ and was the same using either method. $^{31}$P-NMR: δ 151.14.

In accordance with technologies described in the present disclosure, many example phosphoramidites (e.g., those described in Table 1) with diverse substituents were successfully prepared and purified, providing high yield and/or purity. As described in the present disclosure, provided technologies are capable of, among other things, improving elution efficiency and/or decreasing or eliminating decomposition. As demonstrated by the examples, phosphoramidites comprising O$^6$-unprotected guanine residues were successfully purified to provide high yield and purity.

As described in the present disclosure, other hygroscopic solvents may be utilized in accordance with the present disclosure and achieve significantly improved yield and/or purity. In some embodiments, acetonitrile was utilized similarly to methanol as in the examples described herein, and provided significant improvements of the yield and/or purity. In some embodiments, ethyl acetate was utilized similarly to methanol as in the examples described herein, and provided significant improvements of the yield and/or purity.

As demonstrated herein, provided technologies provide surprisingly higher yield and/or purity compared to prior technologies. Among other things, provided technologies are unexpectedly effective in suppressing decomposition of phosphoramidites during purification.

While several embodiments of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described herein. It is, therefore, to be understood that the foregoing embodiments are presented by way of example only and that, within the scope of the appended claims and equivalents thereto, the disclosure may be practiced otherwise than as specifically described and claimed. The present disclosure is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

The invention claimed is:

1. A method for purifying a phosphoramidite, comprising steps of:
   a) contacting a purification medium with a hygroscopic solvent system comprising at least 50% (v/v) acetonitrile or methanol;
   b) contacting the purification medium with a phosphoramidite; and
   c) using the purification medium to purify a phosphoramidite;
wherein the phosphoramidite has the structure of formula I,

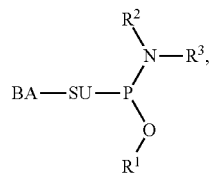

wherein:
BA is R, or an optionally substituted group selected from a 3-30 membered cycloaliphatic ring, a 6-30 membered aryl ring, a 3-30 membered heterocyclyl having 1-10 heteroatoms independently selected from oxygen, nitrogen, sulfur, phosphorus and silicon, a 5-30 membered heteroaryl ring having 1-10 heteroatoms independently selected from oxygen, nitrogen, sulfur, phosphorus and silicon, a natural nucleobase moiety and a modified nucleobase moiety;
SU is a sugar moiety, a modified sugar moiety, -L-O— or

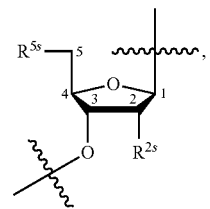

wherein SU is connected to the phosphorus atom in formula I through the oxygen atom;
L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;
$R^{5s}$ is R' or —OR';
$R^{2s}$ is —F, —CN, —N$_3$, —NO, —NO$_2$, —R', —OR', —SR', —N(R')$_2$, -L-R', —O-L-OR', —O-L-SR', or —O-L-N(R')$_2$, or $R^{2s}$ is L connecting C2 with C1, C2, C3, C4 or C5;
-Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;
each of $R^1$, $R^2$, and $R^3$ is independently R', or two or three of $R^1$, $R^2$, and $R^3$ are taken together with their intervening atoms to form:

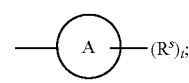

Ring A is an optionally substituted multivalent, monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon;
each $R^s$ is independently R' or -L-R';
t is 0-5;

each R' is independently —R, —C(O)R, —CO₂R, or —SO₂R, or:

two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, a 6-30 membered aryl ring, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

2. The method of claim 1, wherein the hygroscopic solvent system consists of one hygroscopic solvent.

3. The method of claim 1, wherein the hygroscopic solvent system comprises methanol.

4. The method of claim 1, wherein the hygroscopic solvent system comprises acetonitrile.

5. The method of claim 4, wherein the hygroscopic solvent system further comprises a modifier, wherein the modifier is trimethylamine up to 50% (v/v).

6. The method of claim 1, wherein the hygroscopic solvent system is acetonitrile.

7. The method of claim 1, wherein the acetonitrile contains no more than 0.5%, 0.4%, 0.3%, 0.2%, or 0.1% (v/v) water.

8. The method of claim 1, wherein SU is

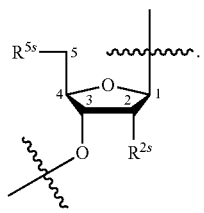

9. The method of claim 8, wherein $R^{5S}$ is —ODMTr.

10. The method of claim 8, wherein $R^{2s}$ is selected form —H, —F, —OMe, and —OCH₂CH₂OMe.

11. The method of claim 1, wherein

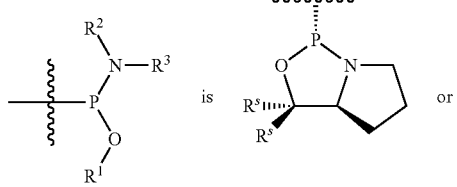

wherein one or more $R^s$ is not hydrogen.

12. The method of claim 1, wherein

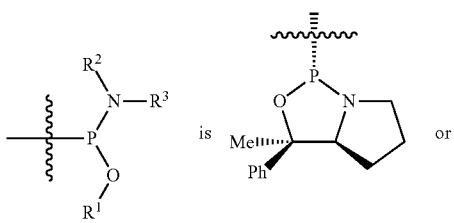

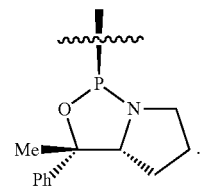

13. The method of claim 1, wherein

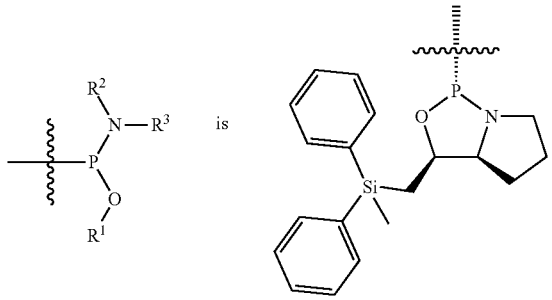

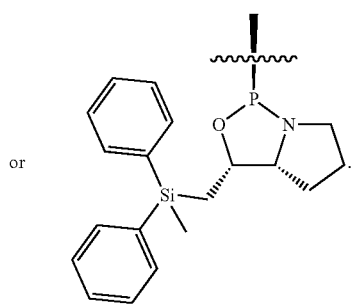

14. The method of claim 1, wherein the phosphoramidite is selected from:
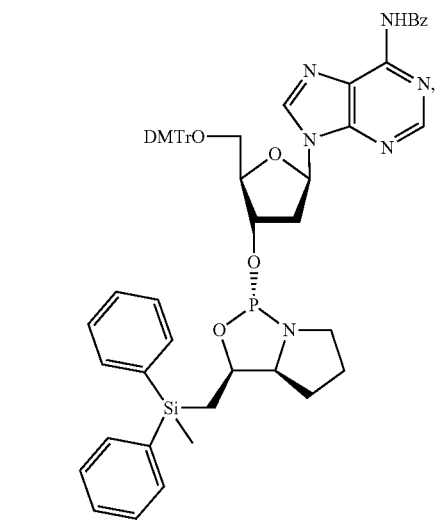
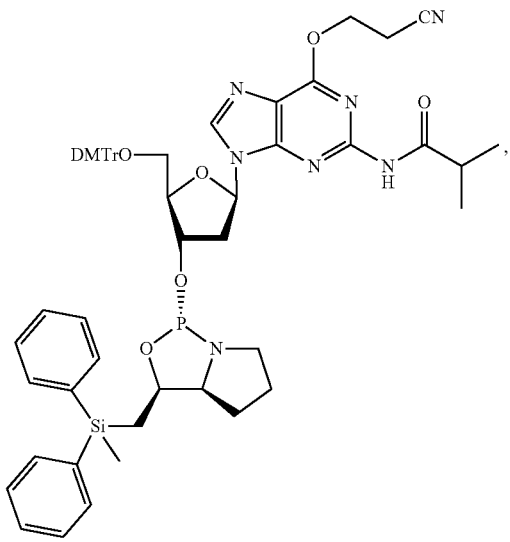
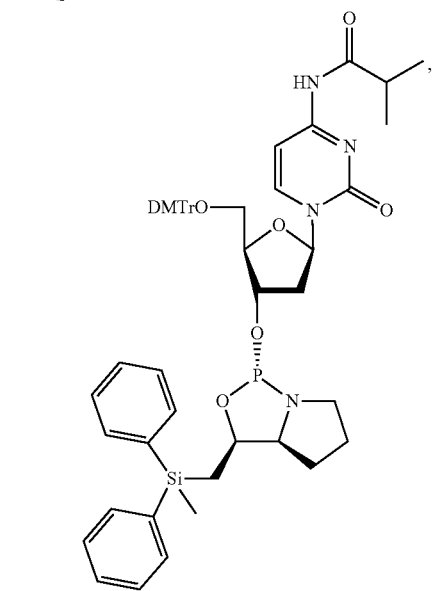
-continued
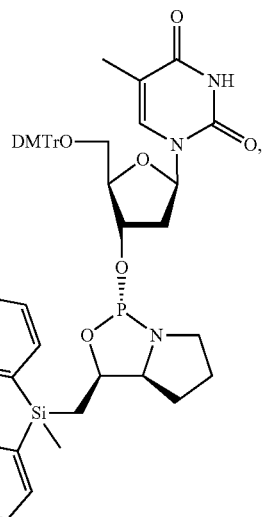
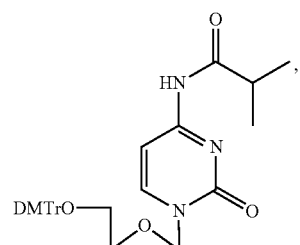
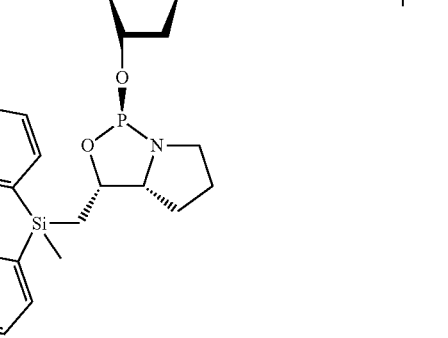

83
-continued
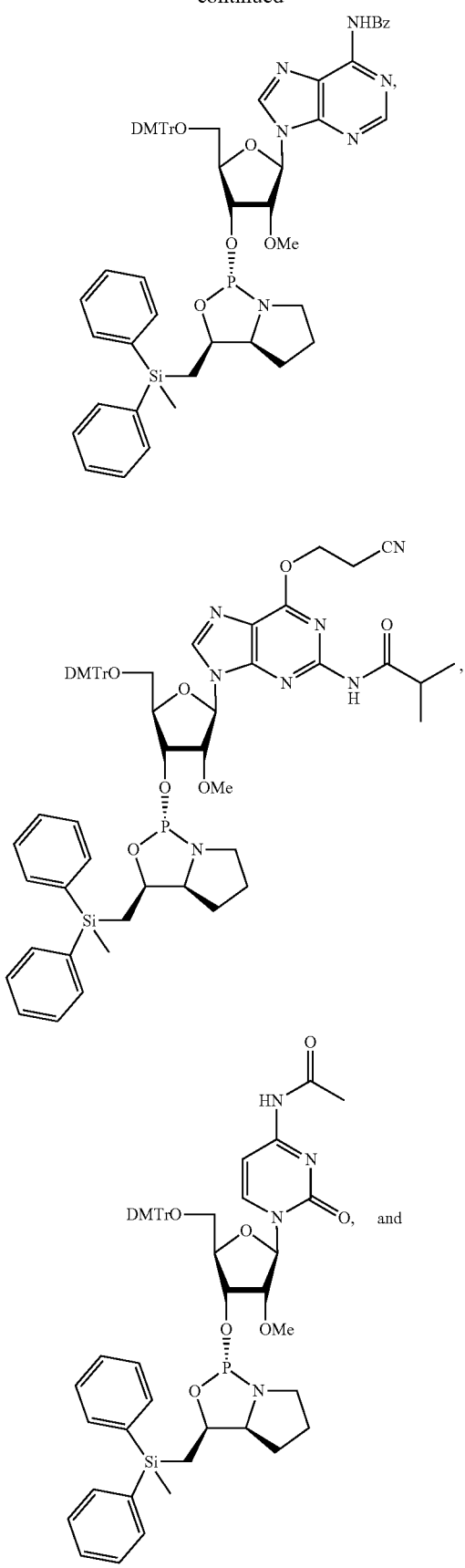
84
-continued
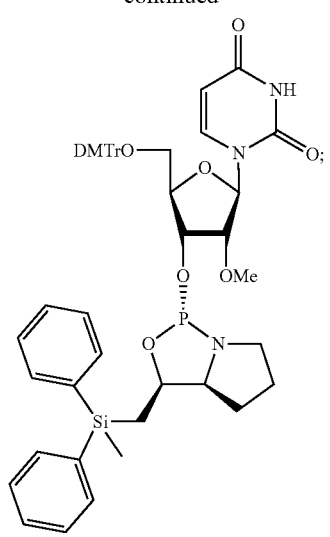
or is selected from:
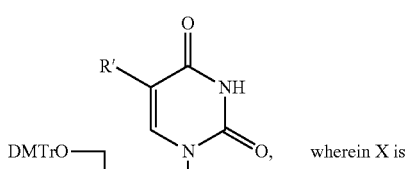, wherein X is
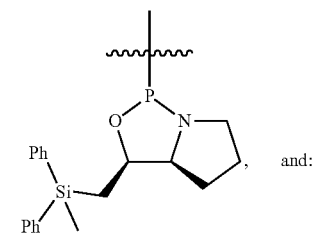 and:
R' is H and R is H,
R' is H, R is OMe,
R' is H and R is $OCH_2CH_2OMe$,
R' is H and R is F,
R' is Me and R is H,
R' is Me, R is OMe,
R' is Me and R is $OCH_2CH_2OMe$, or
R' is Me and R is F;

85

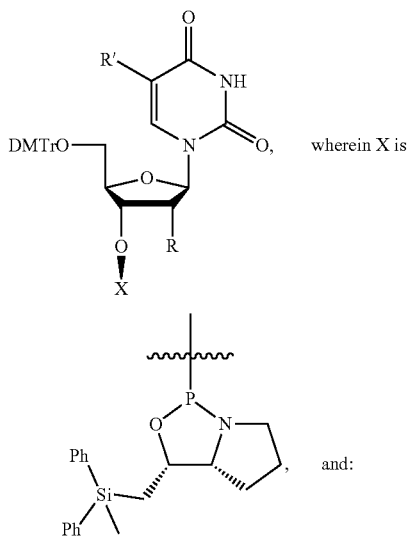

wherein X is

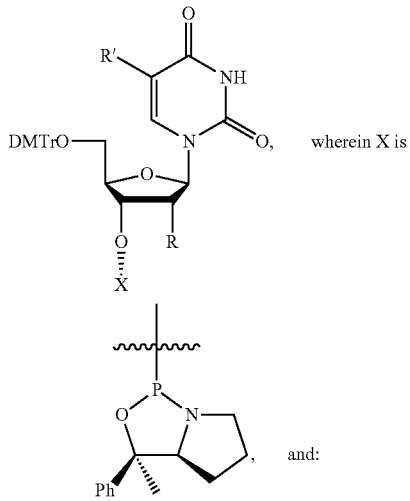

, and:

R' is H and R is H,
R' is H, R is OMe,
R' is H and R is OCH₂CH₂OMe,
R' is H and R is F,
R' is Me and R is H,
R' is Me, R is OMe,
R' is Me and R is OCH₂CH₂OMe, or
R' is Me and R is F;

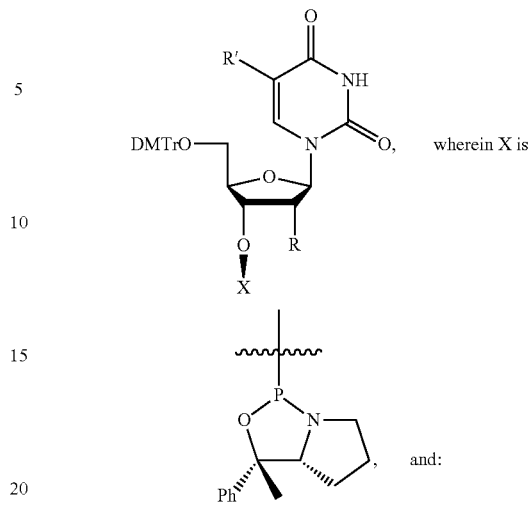

wherein X is

, and:

R' is H and R is H,
R' is H, R is OMe,
R' is H and R is OCH₂CH₂OMe,
R' is H and R is F,
R' is Me and R is H,
R' is Me, R is OMe,
R' is Me and R is OCH₂CH₂OMe, or
R' is Me and R is F;

86 wherein X is

, and:

R' is H and R is H,
R' is H, R is OMe,
R' is H and R is OCH₂CH₂OMe,
R' is H and R is F,
R' is Me and R is H,
R' is Me, R is OMe,
R' is Me and R is OCH₂CH₂OMe, or
R' is Me and R is F;

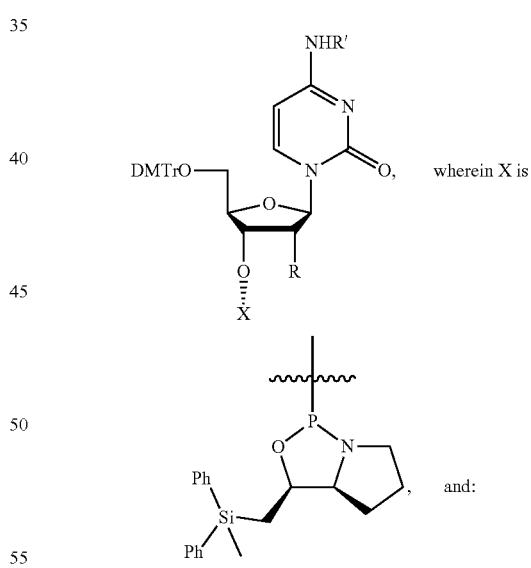

wherein X is

, and:

R' is Ac and R is H,
R' is Ac, R is OMe,
R' is Ac and R is OCH₂CH₂OMe,
R' is Ac and R is F,
R' is iBu and R is H,
R' is iBu, R is OMe,
R' is iBu and R is OCH₂CH₂OMe, or
R' is iBu and R is F;

87

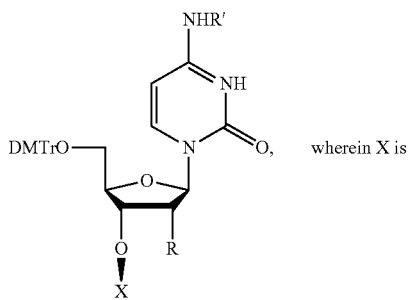
wherein X is

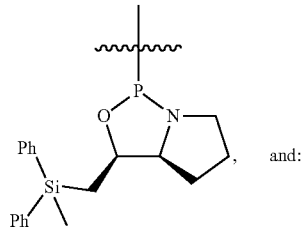
and:

R' is Ac and R is H,
R' is Ac, R is OMe,
R' is Ac and R is OCH₂CH₂OMe,
R' is Ac and R is F,
R' is iBu and R is H,
R' is iBu, R is OMe,
R' is iBu and R is OCH₂CH₂OMe, or
R' is iBu and R is F;

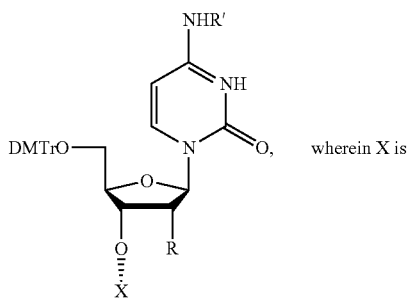
wherein X is

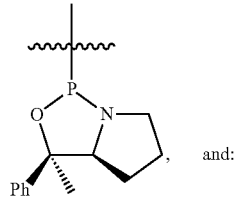
and:

R' is Ac and R is H,
R' is Ac, R is OMe,
R' is Ac and R is OCH₂CH₂OMe,
R' is Ac and R is F,
R' is iBu and R is H,
R' is iBu, R is OMe,
R' is iBu and R is OCH₂CH₂OMe, or
R' is iBu and R is F;

88

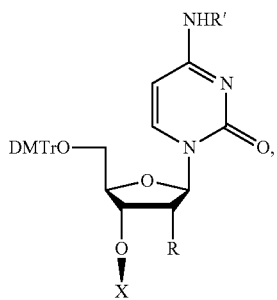
wherein X is 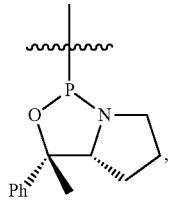 and:

R' is Ac and R is H,
R' is Ac, R is OMe,
R' is Ac and R is OCH₂CH₂OMe,
R' is Ac and R is F,
R' is iBu and R is H,
R' is iBu, R is OMe,
R' is iBu and R is OCH₂CH₂OMe, or
R' is iBu and R is F;

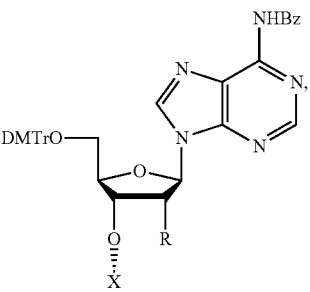
wherein X is 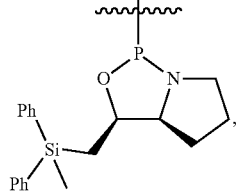 and:

R is H,
R is OMe,
R is OCH₂CH₂OMe, or
R is F;

89
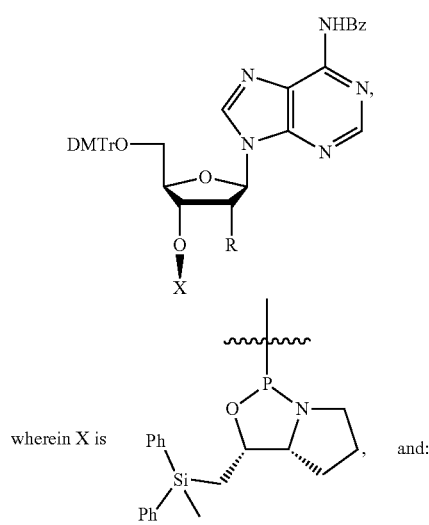
wherein X is 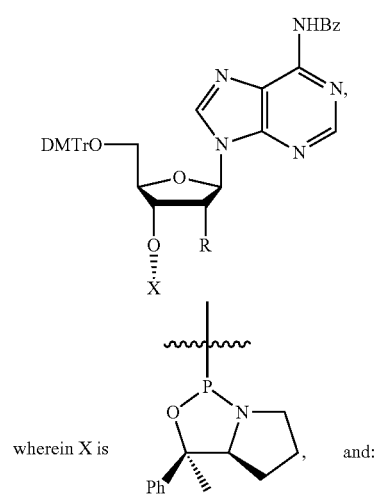, and:
R is H,
R is OMe,
R is OCH₂CH₂OMe, or
R is F;
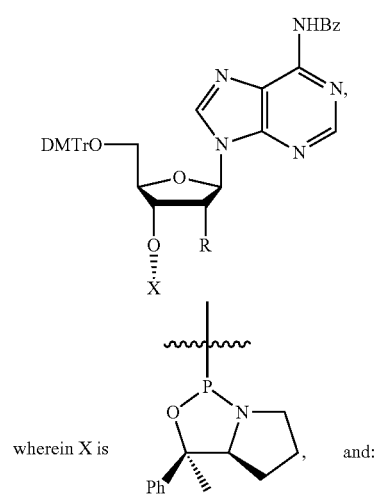
wherein X is 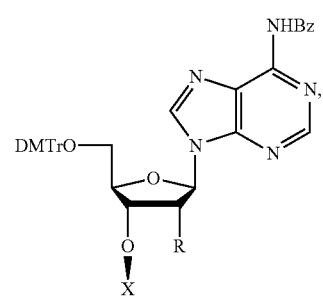, and:
R is H,
R is OMe,
R is OCH₂CH₂OMe, or
R is F;
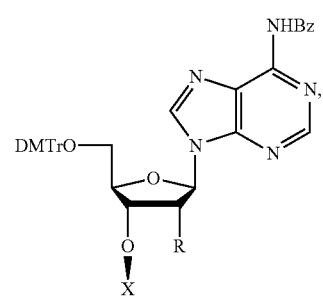
90
-continued
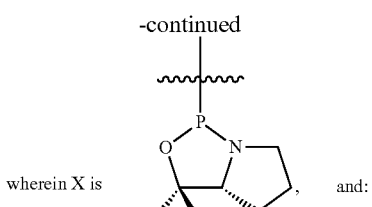
wherein X is 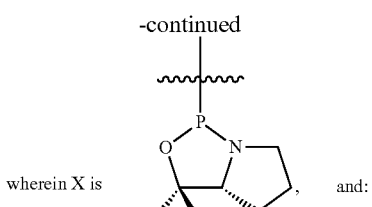, and:
R is H,
R is OMe,
R is OCH₂CH₂OMe, or
R is F;
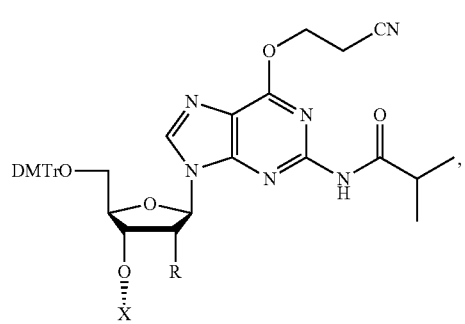
wherein X is 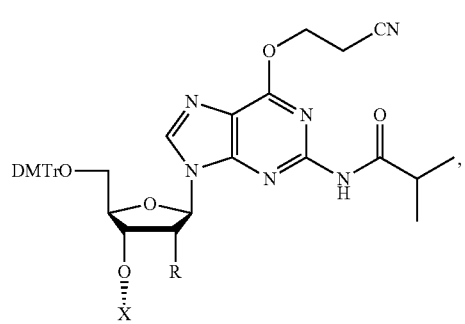, and:
R is H,
R is OMe,
R is OCH₂CH₂OMe, or
R is F;
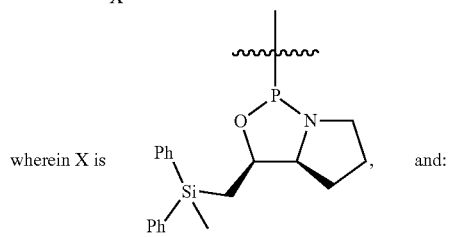
wherein X is 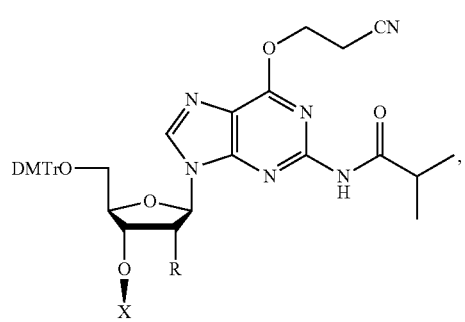, and:
R is H,
R is OMe, R is OCH$_2$CH$_2$OMe, or
R is F;
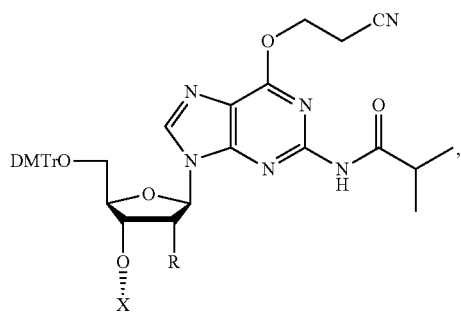
R is H,
R is OMe,
R is OCH$_2$CH$_2$OMe, or
R is F;
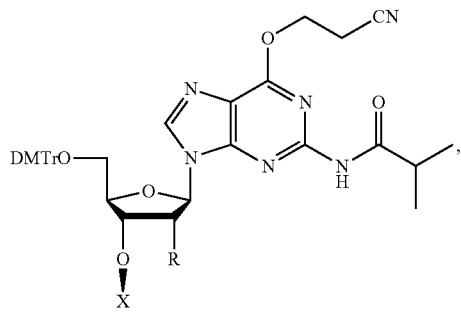
R is H,
R is OMe,
R is OCH$_2$CH$_2$OMe, or
R is F;
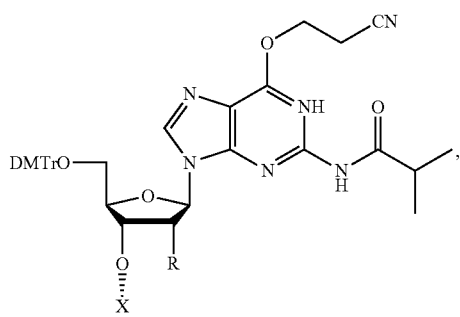
wherein X is 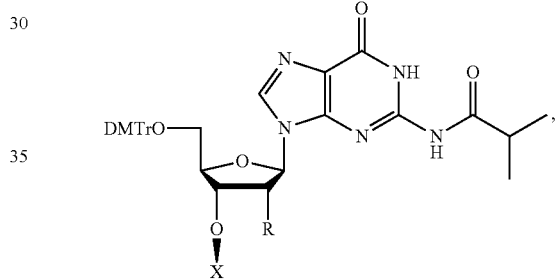, and:
R is H,
R is OMe,
R is OCH$_2$CH$_2$OMe, or
R is F;
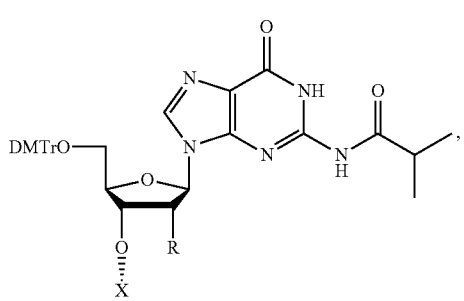

-continued
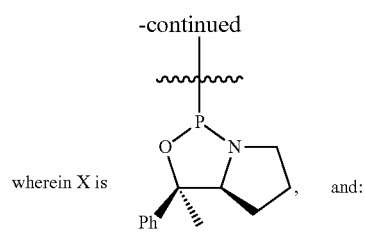
wherein X is [structure], and:
R is H,
R is OMe,
R is OCH$_2$CH$_2$OMe, or
R is F; and
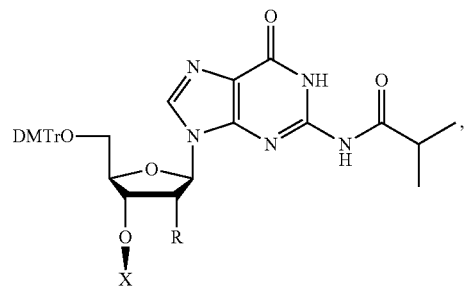
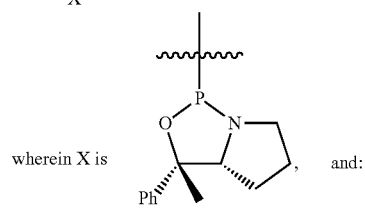
wherein X is [structure], and:
R is H,
R is OMe,
R is OCH$_2$CH$_2$OMe, or
R is F.
15. The method of claim 14, wherein the phosphoramidite is selected from:
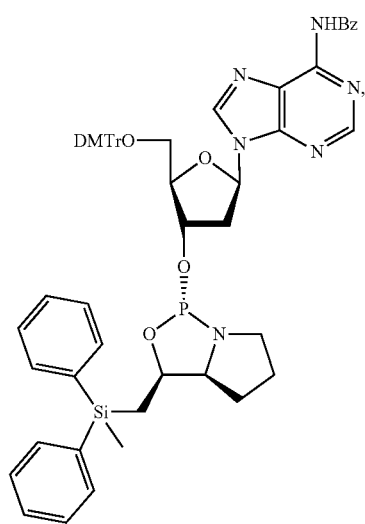
-continued
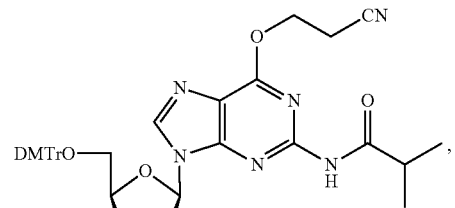
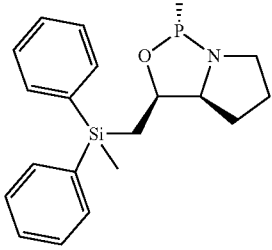
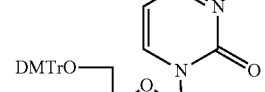
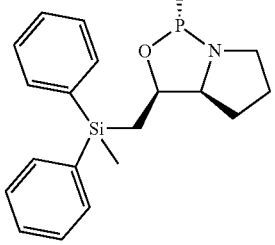
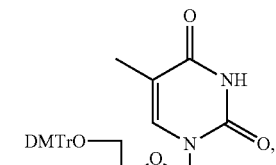
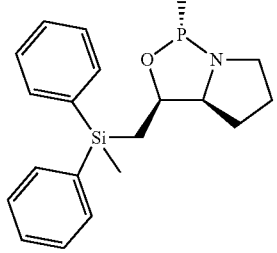

95
-continued
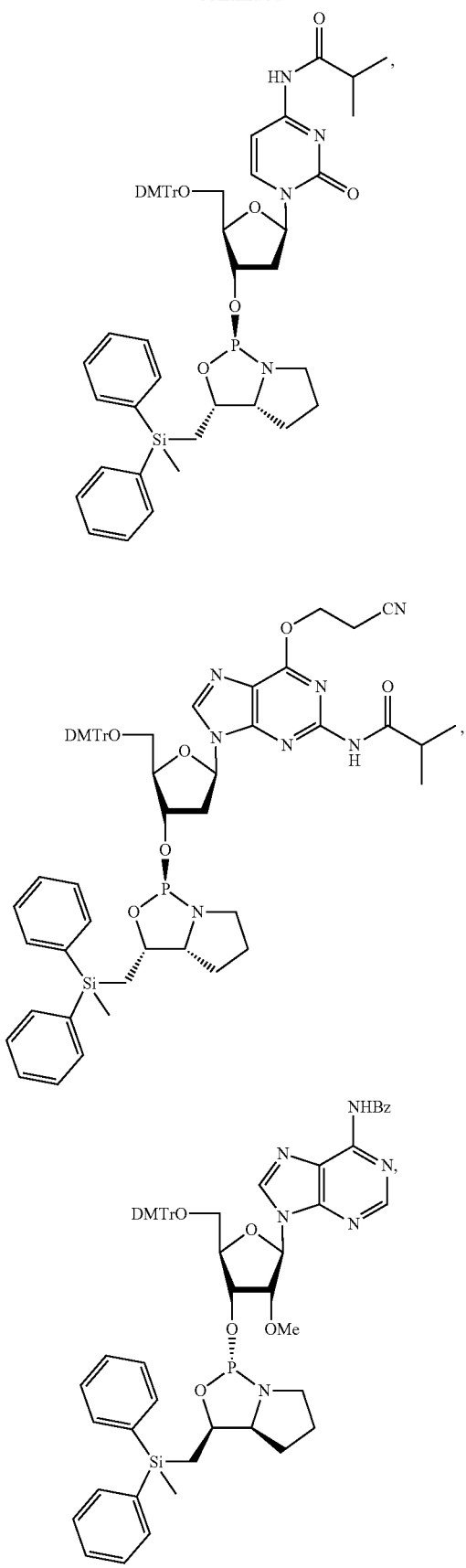
96
-continued
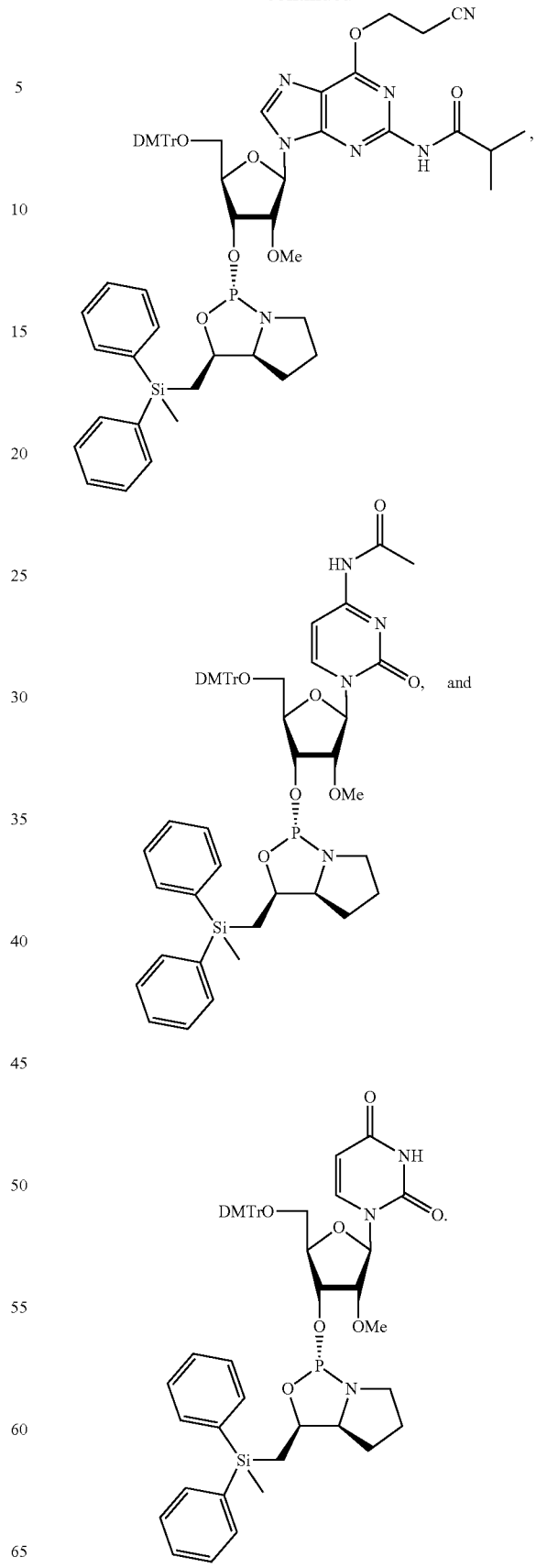

16. The method of claim 14, wherein the phosphoramidite is selected from:

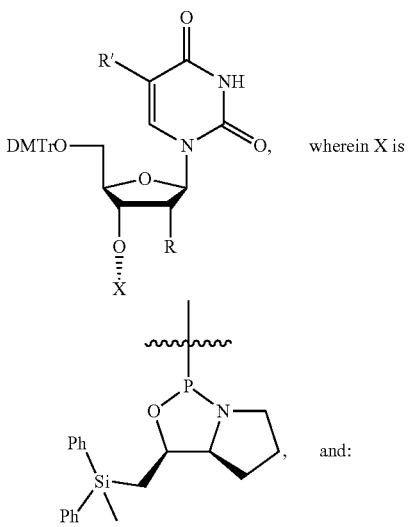

R' is H and R is H,
R' is H, R is OMe,
R' is H and R is OCH$_2$CH$_2$OMe,
R' is H and R is F,
R' is Me and R is H,
R' is Me, R is OMe,
R' is Me and R is OCH$_2$CH$_2$OMe, or
R' is Me and R is F;

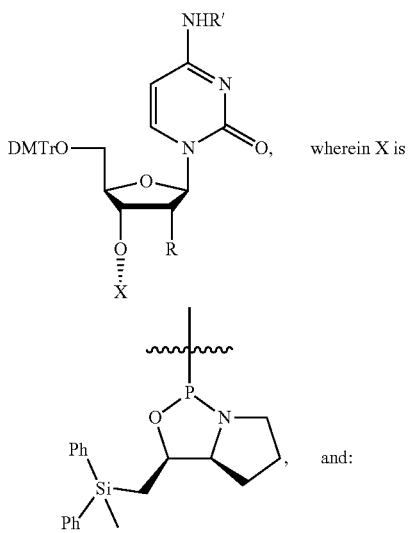

R' is Ac and R is H,
R' is Ac, R is OMe,
R' is Ac and R is OCH$_2$CH$_2$OMe,
R' is Ac and R is F,
R' is iBu and R is H,
R' is iBu, R is OMe,
R' is iBu and R is OCH$_2$CH$_2$OMe, or
R' is iBu and R is F;

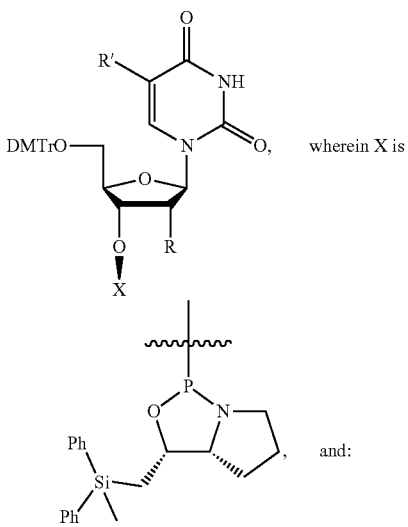

R' is H and R is H,
R' is H, R is OMe,
R' is H and R is OCH$_2$CH$_2$OMe,
R' is H and R is F,
R' is Me and R is H,
R' is Me, R is OMe,
R' is Me and R is OCH$_2$CH$_2$OMe, or
R' is Me and R is F;

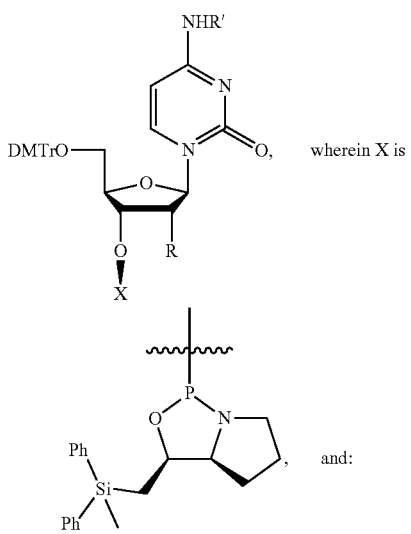

R' is Ac and R is H,
R' is Ac, R is OMe,
R' is Ac and R is OCH$_2$CH$_2$OMe,
R' is Ac and R is F,
R' is iBu and R is H,
R' is iBu, R is OMe,
R' is iBu and R is OCH$_2$CH$_2$OMe, or
R' is iBu and R is F;

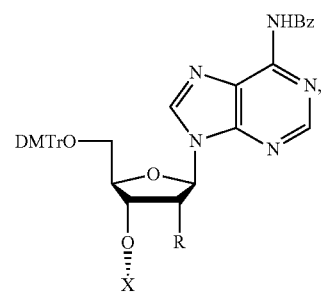
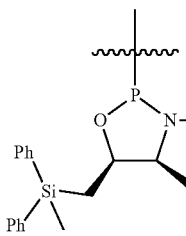
wherein X is , and:
R is H,
R is OMe,
R is OCH$_2$CH$_2$OMe, or
R is F; and
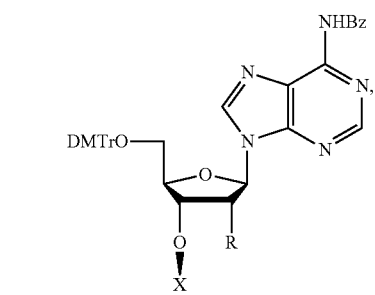
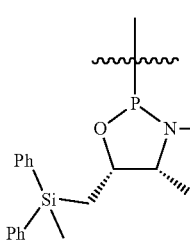
wherein X is , and:
R is H,
R is OMe,
R is OCH$_2$CH$_2$OMe, or
R is F.
17. The method of claim 14, wherein the phosphoramidite is selected from:
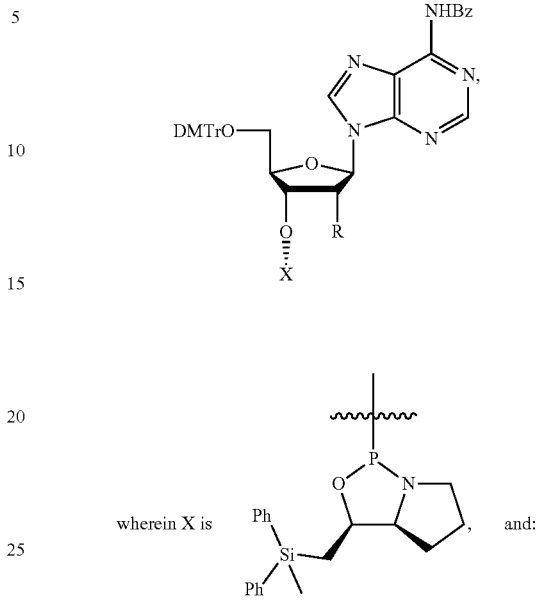
R is H,
R is OMe,
R is OCH$_2$CH$_2$OMe, or
R is F;
R is H,
R is OMe,
R is OCH$_2$CH$_2$OMe, or
R is F;

101

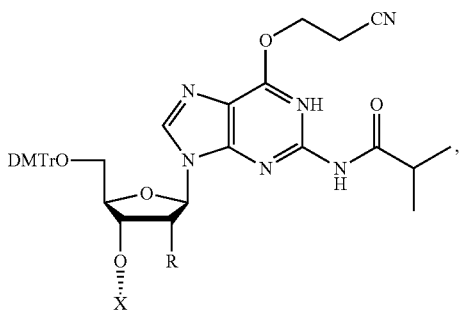

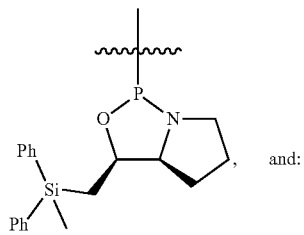
wherein X is

R is H,
R is OMe,
R is OCH₂CH₂OMe, or
R is F;

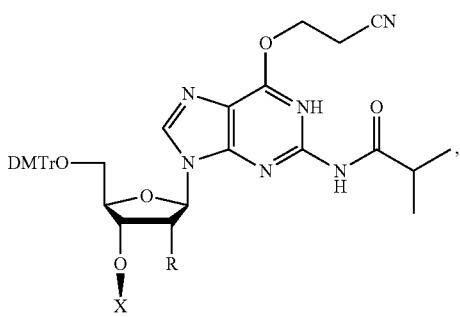

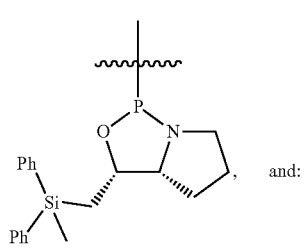
wherein X is

R is H,
R is OMe,
R is OCH₂CH₂OMe, or
R is F;

102

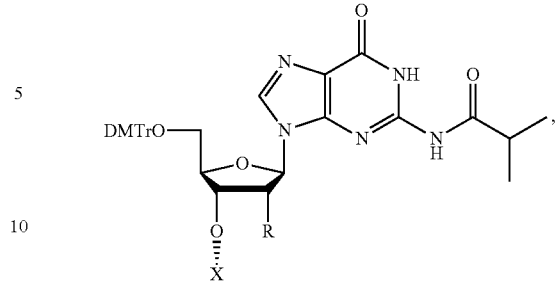

wherein X is , and:

R is H,
R is OMe,
R is OCH₂CH₂OMe, or
R is F; and

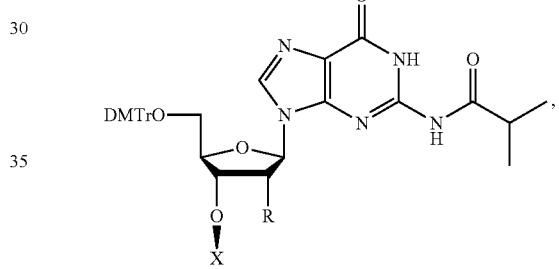

wherein X is , and:

R is H,
R is OMe,
R is OCH₂CH₂OMe, or
R is F.

18. A method for preparing a phosphoramidite, comprising:
1) forming a phosphoramidite from a nucleoside and a chiral auxiliary; and
2) purifying the phosphoramidite obtained in step 1), comprising:
a) contacting a purification medium with a hygroscopic solvent system comprising at least 50% (v/v) acetonitrile or methanol;
b) contacting the purification medium with the phosphoramidite; and
c) using the purification medium to purify a phosphoramidite;
wherein the phosphoramidite has the structure of formula I,

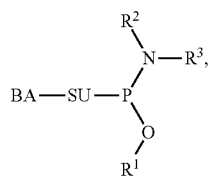

wherein:
BA is R, or an optionally substituted group selected from a 3-30 membered cycloaliphatic ring, a 6-30 membered aryl ring, a 3-30 membered heterocyclyl having 1-10 heteroatoms independently selected from oxygen, nitrogen, sulfur, phosphorus and silicon, a 5-30 membered heteroaryl ring having 1-10 heteroatoms independently selected from oxygen, nitrogen, sulfur, phosphorus and silicon, a natural nucleobase moiety and a modified nucleobase moiety;

SU is

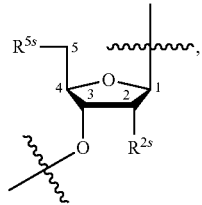

wherein SU is connected to the phosphorus atom in formula I through the oxygen atom;

L is a covalent bond, or a bivalent, optionally substituted, linear or branched group selected from $C_{1-30}$ aliphatic and $C_{1-30}$ heteroaliphatic group having 1-10 heteroatoms independently selected from oxygen, nitrogen, sulfur, phosphorus and silicon, wherein one or more methylene units are optionally and independently replaced by an optionally substituted $C_{1-6}$ alkylene, $C_{1-6}$ alkenylene, —C≡C—, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, or —C(O)O—;

$R^{5s}$ is R' or —OR';

$R^{2s}$ is —F, —CN, —N$_3$, —NO, —NO$_2$, —R', —OR', —SR', —N(R')$_2$, -L-R', —O-L-OR', —O-L-SR', or —O-L-N(R')$_2$, or $R^{2s}$ is L connecting C2 with C1, C2, C3, C4 or C5;

-Cy- is an optionally substituted bivalent ring selected from 3-30 membered carbocyclylene, 6-30 membered arylene, 5-30 membered heteroarylene having 1-10 heteroatoms independently selected from oxygen, nitrogen and sulfur, and 3-30 membered heterocyclylene having 1-10 heteroatoms independently selected from oxygen, nitrogen, sulfur, phosphorus and silicon;

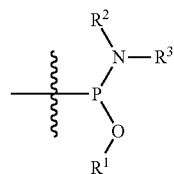

has the structure of

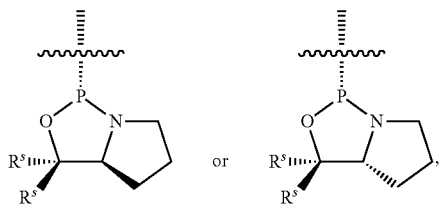

wherein one or more $R^s$ is not hydrogen;
each $R^s$ is independently R' or -L-R';
each R' is independently —R, —C(O)R, —CO$_2$R, or —SO$_2$R, or:
two or more R' are taken together with their intervening atoms to form an optionally substituted monocyclic, bicyclic or polycyclic, saturated, partially unsaturated, or aryl 3-30 membered ring having, in addition to the intervening atoms, 0-10 heteroatoms independently selected from oxygen, nitrogen, sulfur, phosphorus and silicon; and
each R is independently hydrogen, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, a 6-30 membered aryl ring, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

19. The method of claim 18, wherein

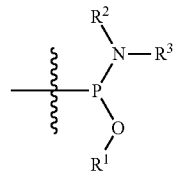

is

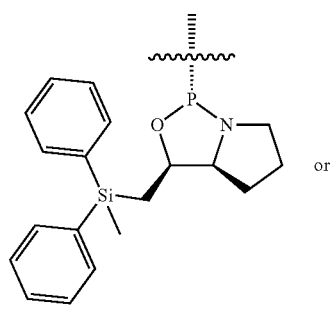

or

-continued
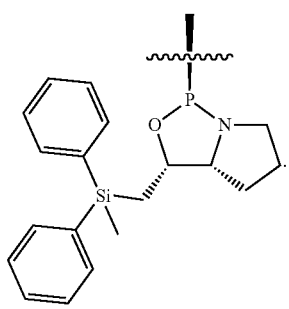
20. The method of claim 18, wherein the
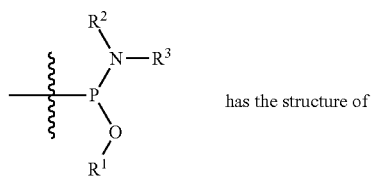 has the structure of
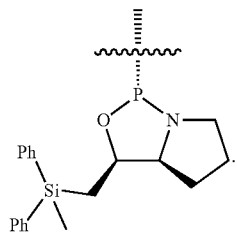
21. The method of claim 20, comprising reacting
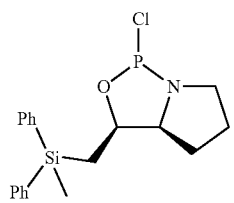 [SMILES: C[Si](C[C@H]1OP(Cl)N2CCC[C@@H]12)(c1ccccc1)c1ccccc1]
with a protected nucleoside.
22. The method of claim 18, wherein the phosphoramidite is selected from:
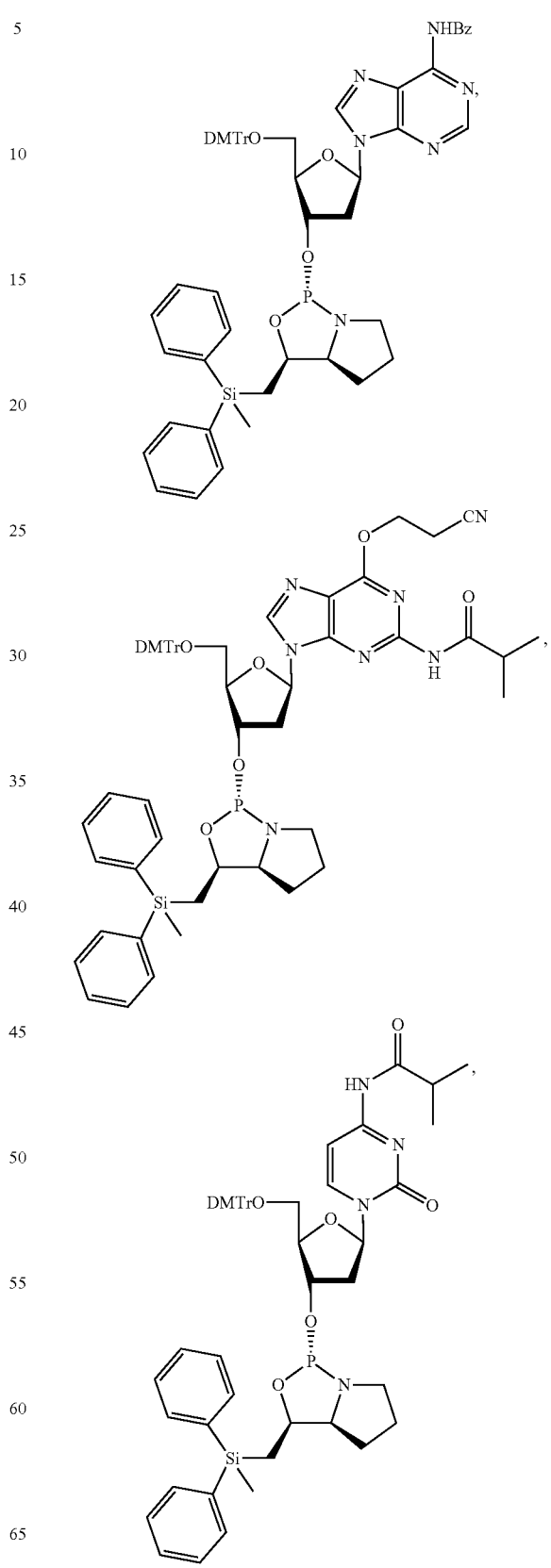

107
-continued
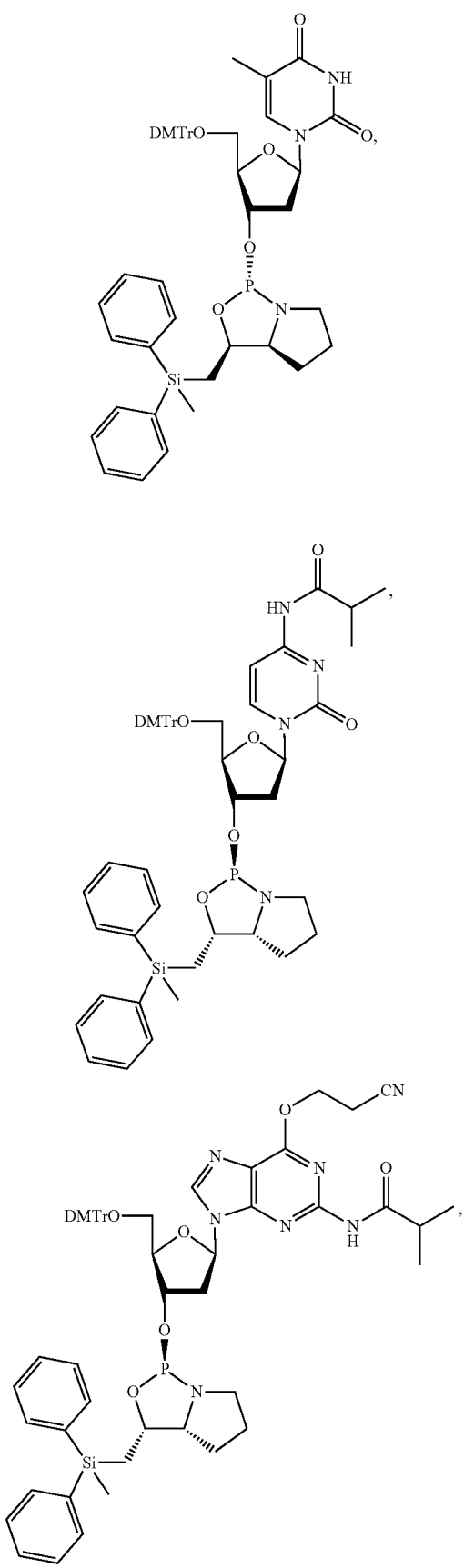
108
-continued
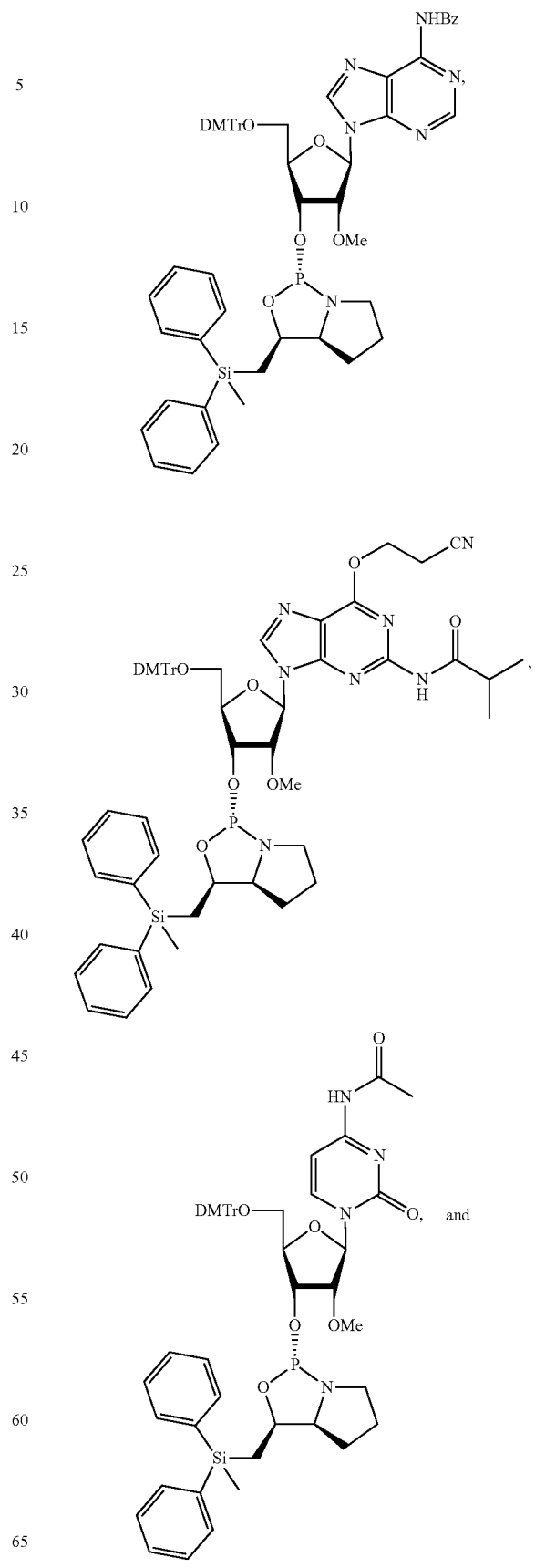

109

-continued

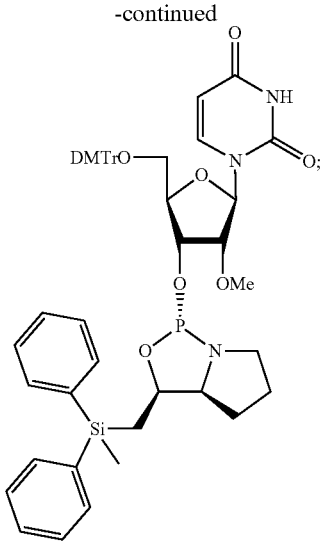

or is selected from:

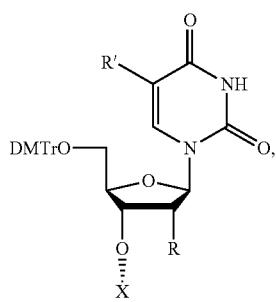

wherein X is 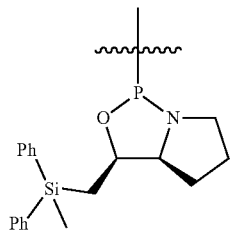, and:

R' is H and R is H,
R' is H, R is OMe,
R' is H and R is OCH₂CH₂OMe,
R' is H and R is F,
R' is Me and R is H,
R' is Me, R is OMe,
R' is Me and R is OCH₂CH₂OMe, or
R' is Me and R is F;

110

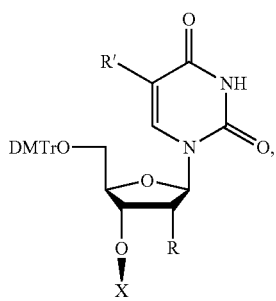

wherein X is

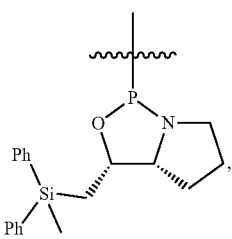

and
R' is H and R is H,
R' is H, R is OMe,
R' is H and R is OCH₂CH₂OMe,
R' is H and R is F,
R' is Me and R is H,
R' is Me, R is OMe,
R' is Me and R is OCH₂CH₂OMe, or
R' is Me and R is F;

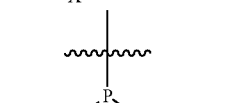

wherein X is 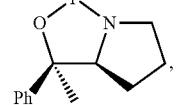, and:

R' is H and R is H,
R' is H, R is OMe,
R' is H and R is OCH₂CH₂OMe,
R' is H and R is F,
R' is Me and R is H,
R' is Me, R is OMe,
R' is Me and R is OCH₂CH₂OMe, or
R' is Me and R is F;

111

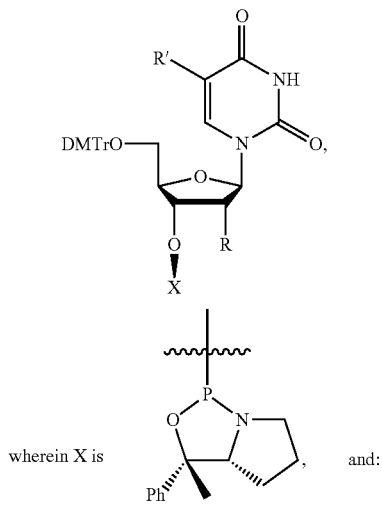

wherein X is

R' is H and R is H,
R' is H, R is OMe,
R' is H and R is OCH₂CH₂OMe,
R' is H and R is F,
R' is Me and R is H,
R' is Me, R is OMe,
R' is Me and R is OCH₂CH₂OMe, or
R' is Me and R is F;

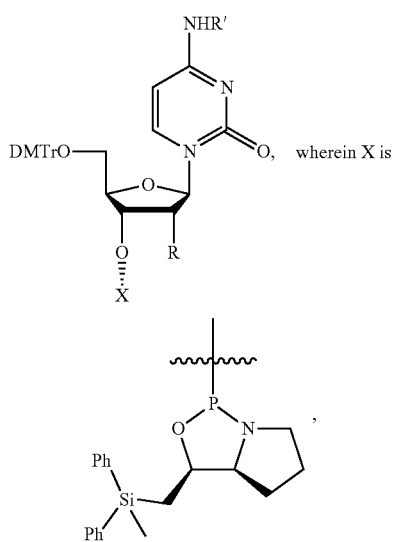

wherein X is

R' is Ac and R is H,
R' is Ac, R is OMe,
R' is Ac and R is OCH₂CH₂OMe,
R' is Ac and R is F,
R' is iBu and R is H,
R' is iBu, R is OMe,
R' is iBu and R is OCH₂CH₂OMe, or
R' is iBu and R is F;

112

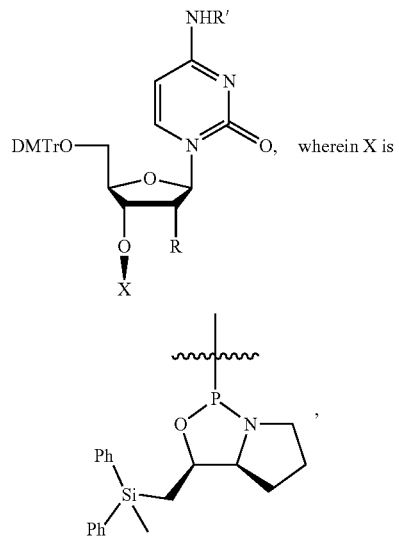

wherein X is

R' is Ac and R is H,
R' is Ac, R is OMe,
R' is Ac and R is OCH₂CH₂OMe,
R' is Ac and R is F,
R' is iBu and R is H,
R' is iBu, R is OMe,
R' is iBu and R is OCH₂CH₂OMe, or
R' is iBu and R is F;

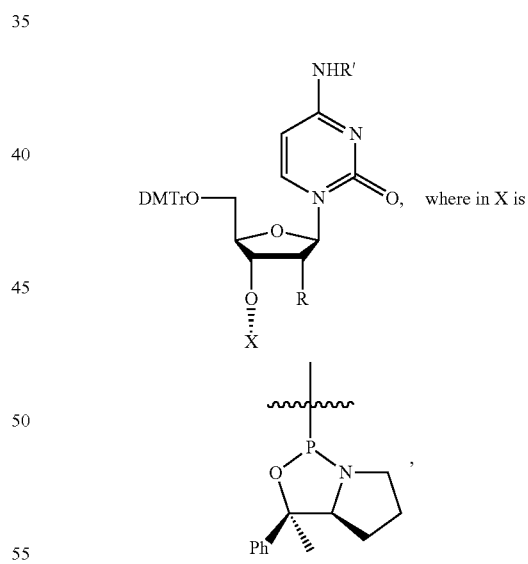

where in X is

R' is Ac and R is H,
R' is Ac, R is OMe,
R' is Ac and R is OCH₂CH₂OMe,
R' is Ac and R is F,
R' is iBu and R is H,
R' is iBu, R is OMe,
R' is iBu and R is OCH₂CH₂OMe, or
R' is iBu and R is F;

113
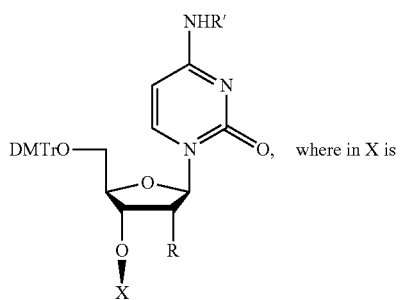, where in X is
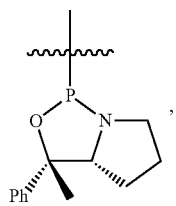,
R' is Ac and R is H,
R' is Ac, R is OMe,
R' is Ac and R is OCH₂CH₂OMe,
R' is Ac and R is F,
R' is iBu and R is H,
R' is iBu, R is OMe,
R' is iBu and R is OCH₂CH₂OMe, or
R' is iBu and R is F;
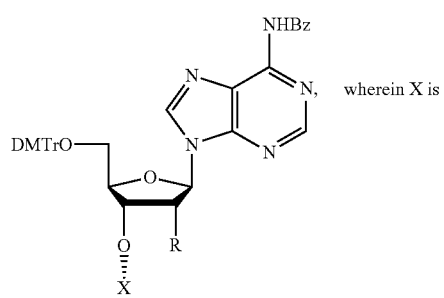
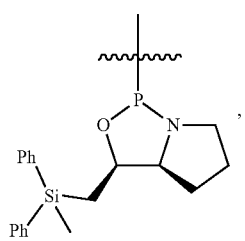,
R is H,
R is OMe,
R is OCH₂CH₂OMe, or
R is F;
114
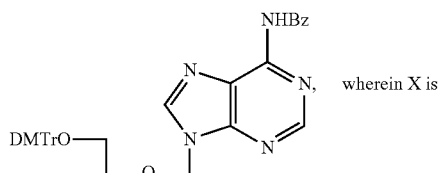, wherein X is
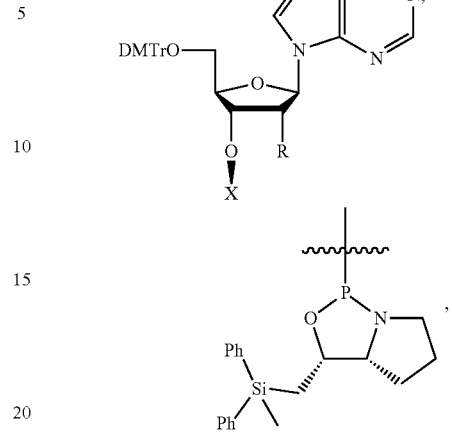,
R is H,
R is OMe,
R is OCH₂CH₂OMe, or
R is F;
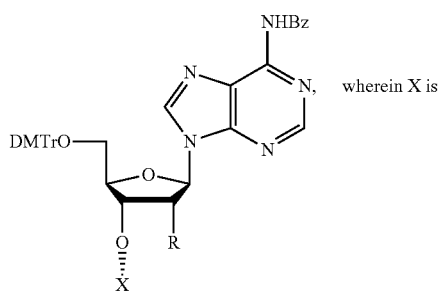, wherein X is
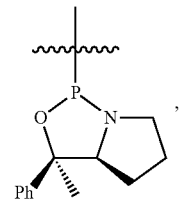,
R is H,
R is OMe,
R is OCH₂CH₂OMe, or
R is F;
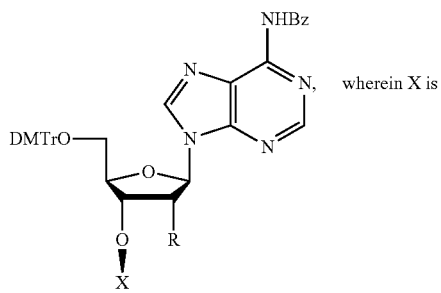, wherein X is 115
-continued
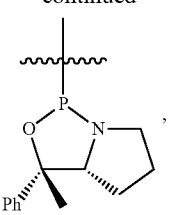
R is H,
R is OMe,
R is OCH$_2$CH$_2$OMe, or
R is F;
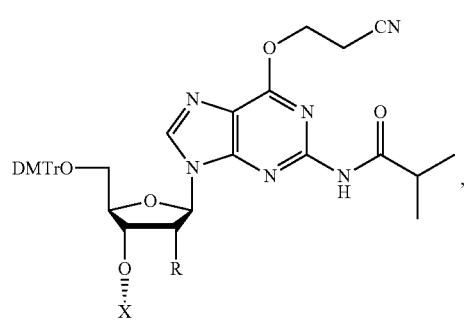
wherein X is
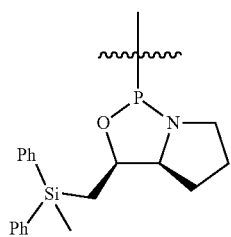
R is H,
R is OMe,
R is OCH$_2$CH$_2$OMe, or
R is F;
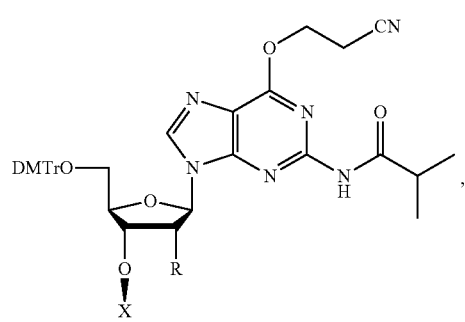
wherein X is
116
-continued
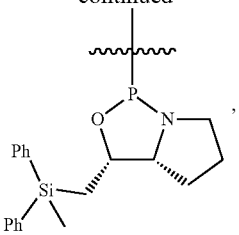
R is H,
R is OMe,
R is OCH$_2$CH$_2$OMe, or
R is F;
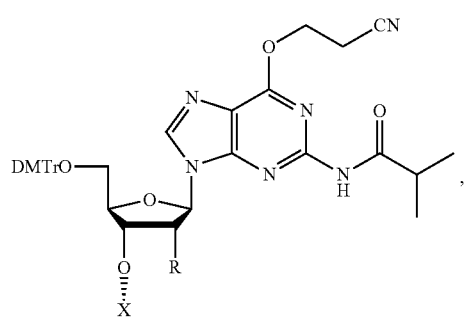
wherein X is
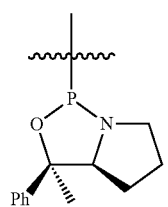
R is H,
R is OMe,
R is OCH$_2$CH$_2$OMe, or
R is F;
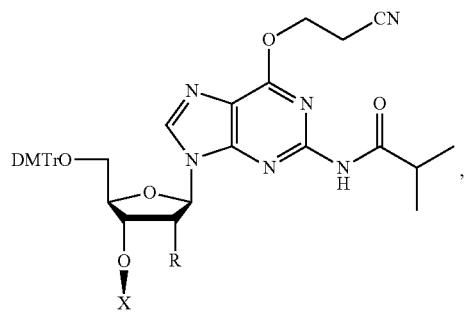
wherein X is
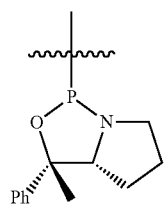

117
R is H,
R is OMe,
R is OCH$_2$CH$_2$OMe, or
R is F;
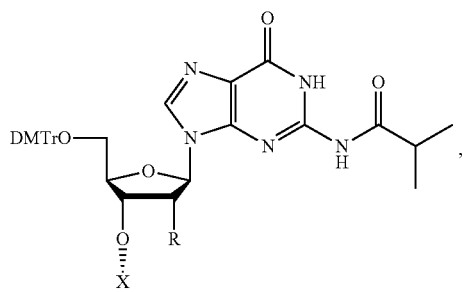
wherein X is
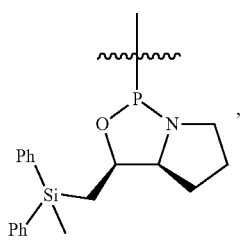
R is H,
R is OMe,
R is OCH$_2$CH$_2$OMe, or
R is F;
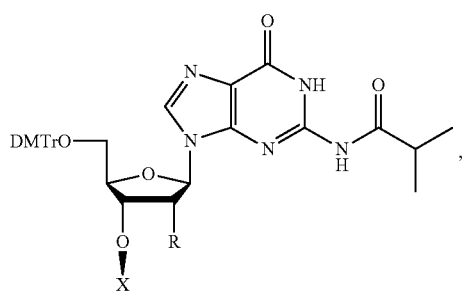
wherein X is
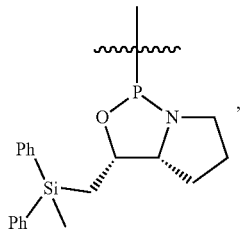
R is H,
R is OMe,
R is OCH$_2$CH$_2$OMe, or
R is F;
118
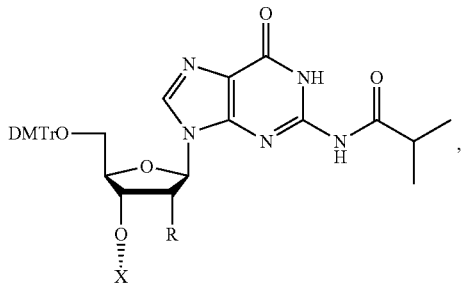
wherein X is
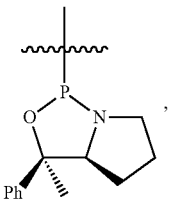
R is H,
R is OMe,
R is OCH$_2$CH$_2$OMe, or
R is F; and
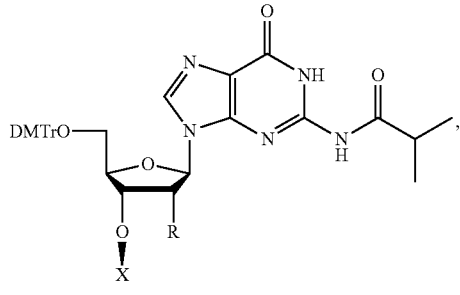
wherein X is 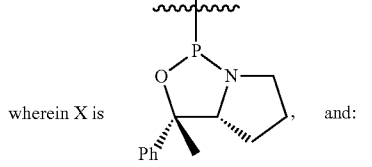 and:
R is H,
R is OMe,
R is OCH$_2$CH$_2$OMe, or
R is F.

23. The method of claim 18, wherein the phosphoramidite is selected from:

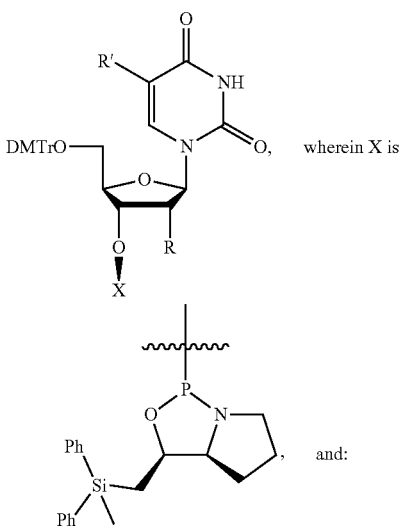

wherein X is

R' is H and R is H,
R' is H, R is OMe,
R' is H and R is OCH$_2$CH$_2$OMe,
R' is H and R is F,
R' is Me and R is H,
R' is Me, R is OMe,
R' is Me and R is OCH$_2$CH$_2$OMe, or
R' is Me and R is F;

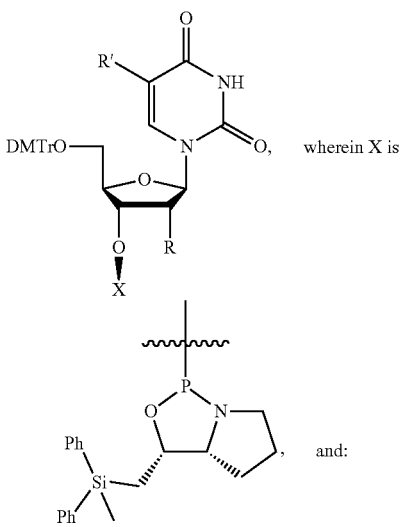

wherein X is

R' is H and R is H,
R' is H, R is OMe,
R' is H and R is OCH$_2$CH$_2$OMe,
R' is H and R is F,
R' is Me and R is H,
R' is Me, R is OMe,
R' is Me and R is OCH$_2$CH$_2$OMe, or
R' is Me and R is F;

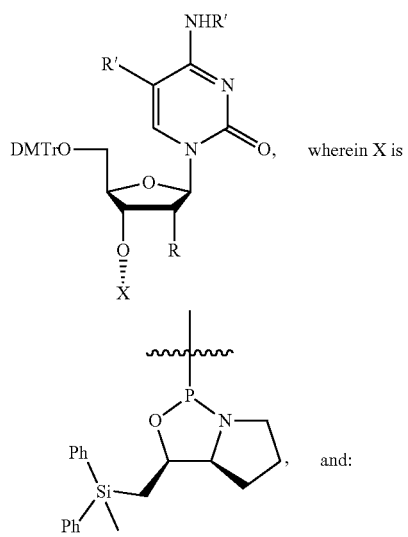

wherein X is

R' is Ac and R is H,
R' is Ac, R is OMe,
R' is Ac and R is OCH$_2$CH$_2$OMe,
R' is Ac and R is F,
R' is iBu and R is H,
R' is iBu, R is OMe,
R' is iBu and R is OCH$_2$CH$_2$OMe, or
R' is iBu and R is F;

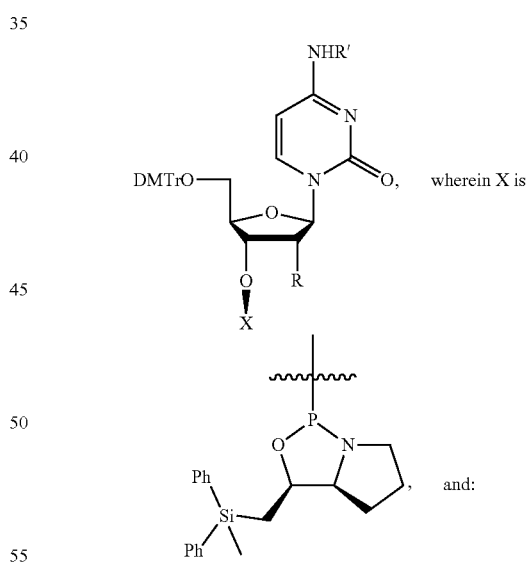

wherein X is

R' is Ac and R is H,
R' is Ac, R is OMe,
R' is Ac and R is OCH$_2$CH$_2$OMe,
R' is Ac and R is F,
R' is iBu and R is H,
R' is iBu, R is OMe,
R' is iBu and R is OCH$_2$CH$_2$OMe, or
R' is iBu and R is F;

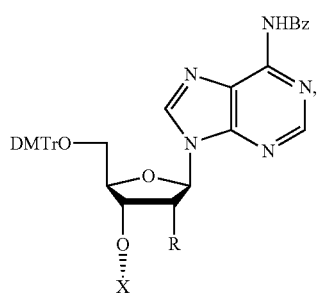
wherein X is
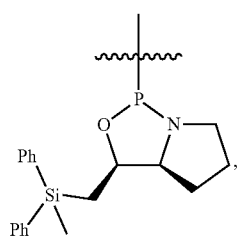, and:
R is H,
R is OMe,
R is OCH$_2$CH$_2$OMe, or
R is F; and
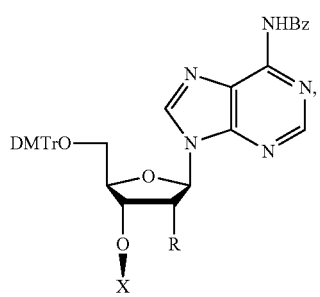
wherein X is
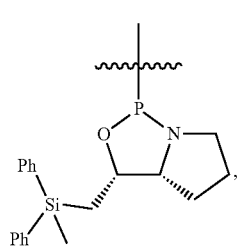, and:
R is H,
R is OMe,
R is OCH$_2$CH$_2$OMe, or
R is F.
24. The method of claim 18, wherein the phosphoramidite is selected from:
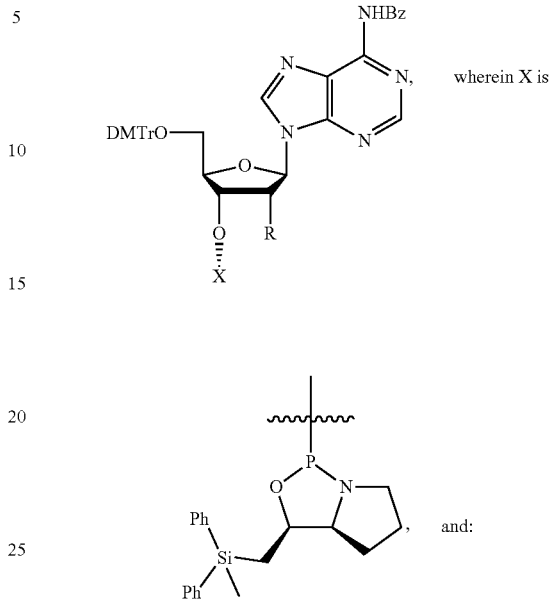
R is H,
R is OMe,
R is OCH$_2$CH$_2$OMe, or
R is F;
R is H,
R is OMe,
R is OCH$_2$CH$_2$OMe, or
R is F;

123
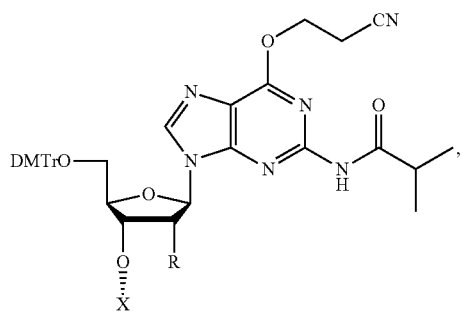
wherein X is 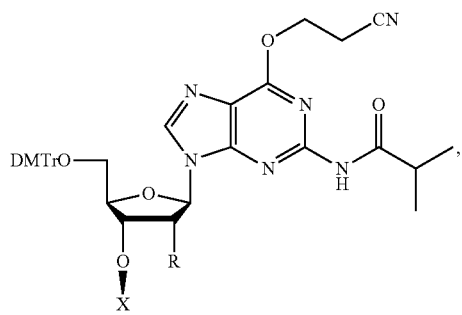, and:
R is H,
R is OMe,
R is OCH$_2$CH$_2$OMe, or
R is F;
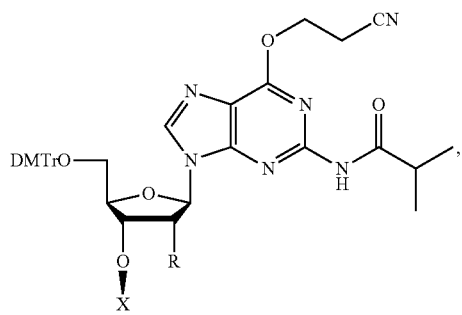
wherein X is [structure], and:
R is H,
R is OMe,
R is OCH$_2$CH$_2$OMe, or
R is F;
124
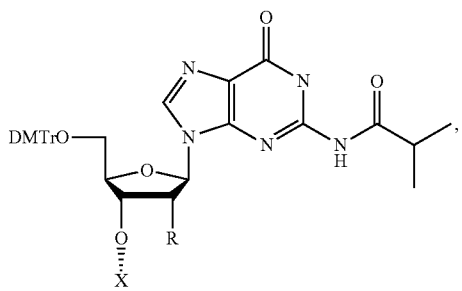
wherein X is [structure], and:
R is H,
R is OMe,
R is OCH$_2$CH$_2$OMe, or
R is F; and
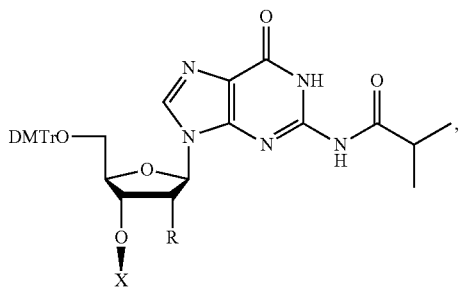
wherein X is [structure], and:
R is H,
R is OMe,
R is OCH$_2$CH$_2$OMe, or
R is F.

25. The method of claim 1, wherein
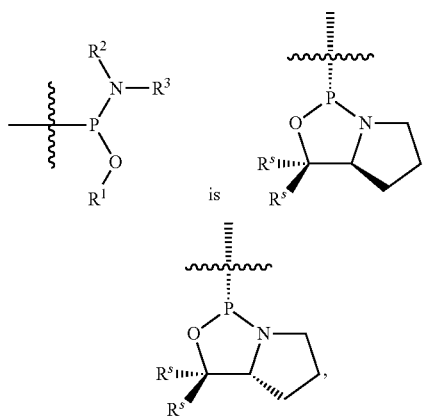 is
wherein one $R^s$ is hydrogen, and the other $R^s$ is -L-R', wherein R' is —SO$_2$R and L is a bivalent, optionally substituted $C_{1-30}$ aliphatic group.
26. The method of claim 18, wherein
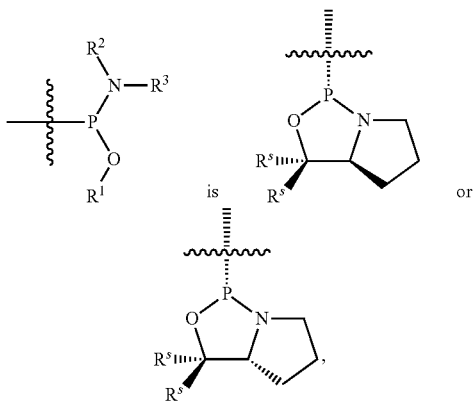 is
wherein one $R^s$ is hydrogen, and the other $R^s$ is -L-R', wherein R' is —SO$_2$R and L is a bivalent, optionally substituted $C_{1-30}$ aliphatic group.
* * * * *